US011278357B2

(12) United States Patent
Ummalaneni

(10) Patent No.: US 11,278,357 B2
(45) Date of Patent: *Mar. 22, 2022

(54) ROBOTIC SYSTEMS FOR DETERMINING AN ANGULAR DEGREE OF FREEDOM OF A MEDICAL DEVICE IN LUMINAL NETWORKS

(71) Applicant: Auris Health, Inc., Redwood City, CA (US)

(72) Inventor: Ritwik Ummalaneni, San Mateo, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/228,542

(22) Filed: Dec. 20, 2018

(65) Prior Publication Data

US 2019/0216548 A1    Jul. 18, 2019

Related U.S. Application Data

(63) Continuation of application No. 16/023,877, filed on Jun. 29, 2018, now Pat. No. 10,159,532, which is a
(Continued)

(51) Int. Cl.
*G06K 9/00* (2006.01)
*A61B 34/20* (2016.01)
(Continued)

(52) U.S. Cl.
CPC ............... *A61B 34/20* (2016.02); *A61B 5/06* (2013.01); *A61B 5/062* (2013.01); *A61B 6/0487* (2020.08);
(Continued)

(58) Field of Classification Search
CPC ......... A61B 34/20; A61B 34/30; A61B 34/70; A61B 5/06; A61B 6/12; A61B 2034/105;
(Continued)

(56) References Cited

U.S. PATENT DOCUMENTS 4,745,908 A    5/1988   Wardle
5,273,025 A    12/1993  Sakiyam et al.
(Continued)

FOREIGN PATENT DOCUMENTS

CN    101147676    3/2008
CN    101222882    7/2008
(Continued)

OTHER PUBLICATIONS

Bell, Charreau S., et al. "Six DOF motion estimation for teleoperated flexible endoscopes using optical flow: A comparative study." 2014 IEEE International Conference on Robotics and Automation (ICRA). IEEE, 2014. (Year: 2014).*
(Continued)

*Primary Examiner* — Jonathan S Lee
(74) *Attorney, Agent, or Firm* — Chang & Hale LLP

(57) ABSTRACT

Certain aspects relate to systems and techniques for navigation-assisted medical devices. Some aspects relate to correlating features of depth information generated based on captured images of an anatomical luminal network with virtual features of depth information generated based on virtual images of a virtual representation of the anatomical luminal network in order to automatically determine aspects of a roll of a medical device within the luminal network.

28 Claims, 23 Drawing Sheets

Related U.S. Application Data continuation of application No. 15/631,691, filed on Jun. 23, 2017, now Pat. No. 10,022,192.

(51) Int. Cl.

| | | |
|---|---|---|
| *A61B 5/06* | (2006.01) | |
| *A61B 34/30* | (2016.01) | |
| *A61B 34/00* | (2016.01) | |
| *A61B 6/04* | (2006.01) | |
| *B25J 9/16* | (2006.01) | |
| *A61B 6/12* | (2006.01) | |
| *A61B 34/10* | (2016.01) | |
| *A61B 90/30* | (2016.01) | |
| *A61B 90/00* | (2016.01) | |
| *A61B 6/03* | (2006.01) | |
| *A61B 6/10* | (2006.01) | |
| *A61B 6/00* | (2006.01) | |
| *A61B 17/00* | (2006.01) | |

(52) U.S. Cl.
CPC ............... *A61B 6/12* (2013.01); *A61B 34/30* (2016.02); *A61B 34/70* (2016.02); *B25J 9/1694* (2013.01); *A61B 6/032* (2013.01); *A61B 6/102* (2013.01); *A61B 6/4441* (2013.01); *A61B 6/463* (2013.01); *A61B 6/466* (2013.01); *A61B 6/487* (2013.01); *A61B 6/488* (2013.01); *A61B 2017/00477* (2013.01); *A61B 2017/00809* (2013.01); *A61B 2034/105* (2016.02); *A61B 2034/2051* (2016.02); *A61B 2034/2065* (2016.02); *A61B 2034/301* (2016.02); *A61B 2090/306* (2016.02); *A61B 2090/309* (2016.02); *A61B 2090/3614* (2016.02)

(58) Field of Classification Search
CPC ...... A61B 2034/2051; A61B 2034/301; A61B 2090/306; A61B 2090/309; A61B 2090/3615; A61B 6/032; A61B 6/102; A61B 6/4441; A61B 6/463; A61B 6/466; A61B 6/487; A61B 6/488; A61B 2017/00477; A61B 17/00809; B25J 9/1694
USPC .......................................... 382/128; 606/130
See application file for complete search history.

(56) References Cited

U.S. PATENT DOCUMENTS

| | | |
|---|---|---|
| 5,526,812 A | 6/1996 | Dumoulin et al. |
| 5,550,953 A | 8/1996 | Seraji |
| 5,831,614 A | 11/1998 | Tognazzini et al. |
| 5,935,075 A | 8/1999 | Casscells |
| 6,038,467 A | 3/2000 | De Bliek et al. |
| 6,047,080 A | 4/2000 | Chen |
| 6,059,718 A | 5/2000 | Taniguchi et al. |
| 6,063,095 A | 5/2000 | Wang et al. |
| 6,167,292 A | 12/2000 | Badano |
| 6,203,493 B1 | 3/2001 | Ben-Haim |
| 6,246,784 B1 | 6/2001 | Summers |
| 6,246,898 B1 | 6/2001 | Vesely |
| 6,332,089 B1 | 12/2001 | Acker |
| 6,425,865 B1 | 7/2002 | Salcudean et al. |
| 6,466,198 B1 | 10/2002 | Feinstein |
| 6,490,467 B1 | 12/2002 | Bucholz |
| 6,553,251 B1 | 4/2003 | Landesmaki |
| 6,665,554 B1 | 12/2003 | Charles |
| 6,690,963 B2 | 2/2004 | Ben-Haim |
| 6,690,964 B2 | 2/2004 | Beiger et al. |
| 6,755,797 B1 | 6/2004 | Stouffer |
| 6,812,842 B2 | 11/2004 | Dimmer |
| 6,899,672 B2 | 5/2005 | Chin |
| 6,926,709 B2 | 8/2005 | Beiger et al. |
| 7,180,976 B2 | 2/2007 | Wink |
| 7,206,627 B2 | 4/2007 | Abovitz |
| 7,233,820 B2 | 6/2007 | Gilboa |
| 7,386,339 B2 | 6/2008 | Strommer et al. |
| 7,697,972 B2 | 4/2010 | Verard |
| 7,756,563 B2 | 7/2010 | Higgins |
| 7,850,642 B2 | 12/2010 | Moll et al. |
| 7,901,348 B2 | 3/2011 | Soper |
| 8,155,403 B2 | 4/2012 | Tschirren |
| 8,190,238 B2 | 5/2012 | Moll et al. |
| 8,290,571 B2 | 10/2012 | Younge et al. |
| 8,298,135 B2 | 10/2012 | Ito et al. |
| 8,317,746 B2 | 11/2012 | Sewell et al. |
| 8,394,054 B2 | 3/2013 | Wallace et al. |
| 8,460,236 B2 | 6/2013 | Roelle et al. |
| 8,821,376 B2 | 9/2014 | Tolkowsky |
| 8,858,424 B2 | 10/2014 | Hasegawa |
| 8,929,631 B2 | 1/2015 | Pfister et al. |
| 9,014,851 B2 | 4/2015 | Wong et al. |
| 9,084,623 B2 | 7/2015 | Gomez et al. |
| 9,125,639 B2 | 9/2015 | Mathis |
| 9,138,129 B2 | 9/2015 | Diolaiti |
| 9,183,354 B2 | 11/2015 | Baker et al. |
| 9,186,046 B2 | 11/2015 | Ramamurthy et al. |
| 9,272,416 B2 | 3/2016 | Hourtash et al. |
| 9,289,578 B2 | 3/2016 | Walker et al. |
| 9,459,087 B2 | 10/2016 | Dunbar |
| 9,504,604 B2 | 11/2016 | Alvarez |
| 9,561,083 B2 | 2/2017 | Yu et al. |
| 9,603,668 B2 | 3/2017 | Weingarten et al. |
| 9,622,827 B2 | 4/2017 | Yu et al. |
| 9,629,682 B2 | 4/2017 | Wallace et al. |
| 9,636,184 B2 | 5/2017 | Lee et al. |
| 9,710,921 B2 | 7/2017 | Wong et al. |
| 9,713,509 B2 | 7/2017 | Schuh et al. |
| 9,717,563 B2 | 8/2017 | Tognaccini |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,080,576 B2 | 9/2018 | Romo et al. |
| 10,123,755 B2 | 11/2018 | Walker et al. |
| 10,130,345 B2 | 11/2018 | Wong et al. |
| 10,136,950 B2 | 11/2018 | Schoenefeld |
| 10,136,959 B2 | 11/2018 | Mintz et al. |
| 10,143,360 B2 | 12/2018 | Roelle et al. |
| 10,143,526 B2 | 12/2018 | Walker et al. |
| 10,145,747 B1 | 12/2018 | Lin et al. |
| 10,149,720 B2 | 12/2018 | Romo |
| 10,159,532 B1 | 12/2018 | Ummalaneni |
| 10,159,533 B2 | 12/2018 | Moll et al. |
| 10,169,875 B2 | 1/2019 | Mintz et al. |
| 10,278,778 B2 * | 5/2019 | State ..................... A61B 90/10 |
| 10,434,660 B2 | 10/2019 | Meyer |
| 10,464,209 B2 | 11/2019 | Ho et al. |
| 10,470,830 B2 | 11/2019 | Hill et al. |
| 10,482,599 B2 | 11/2019 | Mintz et al. |
| 10,492,741 B2 | 12/2019 | Walker et al. |
| 10,517,692 B2 | 12/2019 | Eyre et al. |
| 10,524,866 B2 | 1/2020 | Srinivasan et al. |
| 10,531,864 B2 | 1/2020 | Wong et al. |
| 10,539,478 B2 | 1/2020 | Lin et al. |
| 10,555,778 B2 | 2/2020 | Ummalaneni et al. |

(56) References Cited

U.S. PATENT DOCUMENTS

| | | |
|---|---|---|
| 10,702,348 B2 | 7/2020 | Moll et al. |
| 10,820,954 B2 | 11/2020 | Marsot et al. |
| 2001/0021843 A1 | 9/2001 | Bosselmann et al. |
| 2001/0039421 A1 | 11/2001 | Heilbrun |
| 2002/0065455 A1 | 5/2002 | Ben-Haim et al. |
| 2002/0077533 A1 | 6/2002 | Bieger et al. |
| 2002/0120188 A1 | 8/2002 | Brock et al. |
| 2003/0105603 A1 | 6/2003 | Hardesty |
| 2003/0125622 A1 | 7/2003 | Schweikard |
| 2003/0181809 A1 | 9/2003 | Hall et al. |
| 2003/0195664 A1 | 10/2003 | Nowlin et al. |
| 2004/0047044 A1 | 3/2004 | Dalton |
| 2004/0072066 A1 | 4/2004 | Cho et al. |
| 2004/0097806 A1 | 5/2004 | Hunter et al. |
| 2004/0186349 A1 | 9/2004 | Ewers |
| 2004/0249267 A1 | 12/2004 | Gilboa |
| 2004/0263535 A1 | 12/2004 | Birkenbach et al. |
| 2005/0027397 A1 | 2/2005 | Niemeyer |
| 2005/0060006 A1 | 3/2005 | Pflueger |
| 2005/0085714 A1 | 4/2005 | Foley et al. |
| 2005/0107679 A1 | 5/2005 | Geiger |
| 2005/0143649 A1 | 6/2005 | Minai et al. |
| 2005/0143655 A1 | 6/2005 | Satoh |
| 2005/0182295 A1 | 8/2005 | Soper et al. |
| 2005/0182319 A1 | 8/2005 | Glossop |
| 2005/0193451 A1 | 9/2005 | Quistgaard et al. |
| 2005/0197557 A1 | 9/2005 | Strommer et al. |
| 2005/0256398 A1 | 11/2005 | Hastings et al. |
| 2005/0272975 A1 | 12/2005 | McWeeney et al. |
| 2006/0004286 A1 | 1/2006 | Chang |
| 2006/0015096 A1 | 1/2006 | Hauck et al. |
| 2006/0025668 A1 | 2/2006 | Peterson |
| 2006/0058643 A1 | 3/2006 | Florent |
| 2006/0084860 A1 | 4/2006 | Geiger |
| 2006/0095066 A1 | 5/2006 | Chang |
| 2006/0098851 A1 | 5/2006 | Shoham |
| 2006/0149134 A1 | 7/2006 | Soper et al. |
| 2006/0173290 A1 | 8/2006 | Lavallee et al. |
| 2006/0184016 A1 | 8/2006 | Glossop |
| 2006/0209019 A1 | 9/2006 | Hu |
| 2006/0258935 A1 | 11/2006 | Pile-Spellman et al. |
| 2006/0258938 A1 | 11/2006 | Hoffman et al. |
| 2007/0032826 A1 | 2/2007 | Schwartz |
| 2007/0055128 A1 | 3/2007 | Glossop |
| 2007/0055144 A1 | 3/2007 | Neustadter |
| 2007/0073136 A1 | 3/2007 | Metzger |
| 2007/0083193 A1 | 4/2007 | Werneth |
| 2007/0123748 A1 | 5/2007 | Meglan |
| 2007/0135803 A1 | 6/2007 | Belson |
| 2007/0135886 A1 | 6/2007 | Maschke |
| 2007/0156019 A1 | 7/2007 | Larkin et al. |
| 2007/0161857 A1 | 7/2007 | Durant et al. |
| 2007/0167743 A1 | 7/2007 | Honda |
| 2007/0167801 A1 | 7/2007 | Webler et al. |
| 2007/0208252 A1 | 9/2007 | Makower |
| 2007/0253599 A1 | 11/2007 | White et al. |
| 2007/0269001 A1 | 11/2007 | Maschke |
| 2007/0293721 A1 | 12/2007 | Gilboa |
| 2007/0299353 A1 | 12/2007 | Harlev et al. |
| 2008/0071140 A1 | 3/2008 | Gattani |
| 2008/0079421 A1 | 4/2008 | Jensen |
| 2008/0103389 A1 | 5/2008 | Begelman et al. |
| 2008/0118118 A1 | 5/2008 | Berger |
| 2008/0118135 A1 | 5/2008 | Averbach |
| 2008/0123921 A1 | 5/2008 | Gielen et al. |
| 2008/0147089 A1 | 6/2008 | Loh |
| 2008/0161681 A1 | 7/2008 | Hauck |
| 2008/0183064 A1 | 7/2008 | Chandonnet |
| 2008/0183068 A1 | 7/2008 | Carls et al. |
| 2008/0183073 A1 | 7/2008 | Higgins et al. |
| 2008/0183188 A1 | 7/2008 | Carls et al. |
| 2008/0201016 A1 | 8/2008 | Finlay |
| 2008/0207997 A1 | 8/2008 | Higgins et al. |
| 2008/0212082 A1 | 9/2008 | Froggatt et al. |
| 2008/0218770 A1 | 9/2008 | Moll et al. |
| 2008/0221425 A1 | 9/2008 | Olson et al. |
| 2008/0243142 A1 | 10/2008 | Gildenberg |
| 2008/0262297 A1 | 10/2008 | Gilboa |
| 2008/0275349 A1 | 11/2008 | Halperin |
| 2008/0287963 A1 | 11/2008 | Rogers et al. |
| 2008/0300478 A1 | 12/2008 | Zuhars et al. |
| 2008/0306490 A1 | 12/2008 | Lakin et al. |
| 2008/0312501 A1 | 12/2008 | Hasegawa et al. |
| 2009/0030307 A1 | 1/2009 | Govari |
| 2009/0054729 A1 | 2/2009 | Mori |
| 2009/0076476 A1 | 3/2009 | Barbagli et al. |
| 2009/0149867 A1 | 6/2009 | Glozman |
| 2009/0209817 A1 | 8/2009 | Averbuch |
| 2009/0227861 A1 | 9/2009 | Ganatra |
| 2009/0228020 A1 | 9/2009 | Wallace et al. |
| 2009/0248036 A1 | 10/2009 | Hoffman et al. |
| 2009/0259230 A1 | 10/2009 | Khadem |
| 2009/0262109 A1 | 10/2009 | Markowitz et al. |
| 2009/0292166 A1 | 11/2009 | Ito |
| 2009/0295797 A1 | 12/2009 | Sakaguchi |
| 2010/0008555 A1 | 1/2010 | Trumer |
| 2010/0030061 A1 | 2/2010 | Canfield |
| 2010/0039506 A1 | 2/2010 | Sarvestani et al. |
| 2010/0041949 A1 | 2/2010 | Tolkowsky |
| 2010/0054536 A1 | 3/2010 | Huang |
| 2010/0113852 A1 | 5/2010 | Sydora |
| 2010/0121139 A1 | 5/2010 | OuYang |
| 2010/0160733 A1 | 6/2010 | Gilboa |
| 2010/0161022 A1 | 6/2010 | Tolkowsky |
| 2010/0161129 A1 | 6/2010 | Costa et al. |
| 2010/0225209 A1 | 9/2010 | Goldberg |
| 2010/0240989 A1 | 9/2010 | Stoianovici |
| 2010/0290530 A1 | 11/2010 | Huang et al. |
| 2010/0292565 A1 | 11/2010 | Meyer |
| 2010/0298641 A1 | 11/2010 | Tanaka |
| 2010/0328455 A1 | 12/2010 | Nam et al. |
| 2011/0054303 A1 | 3/2011 | Barrick |
| 2011/0092808 A1 | 4/2011 | Shachar |
| 2011/0184238 A1 | 7/2011 | Higgins |
| 2011/0234780 A1 | 9/2011 | Ito |
| 2011/0238082 A1 | 9/2011 | Wenderow |
| 2011/0245665 A1 | 10/2011 | Nentwick |
| 2011/0248987 A1 | 10/2011 | Mitchell |
| 2011/0249016 A1 | 10/2011 | Zhang |
| 2011/0257480 A1 | 10/2011 | Takahashi |
| 2011/0276179 A1 | 11/2011 | Banks et al. |
| 2011/0319910 A1 | 12/2011 | Roelle et al. |
| 2012/0046521 A1 | 2/2012 | Hunter et al. |
| 2012/0056986 A1 | 3/2012 | Popovic |
| 2012/0059248 A1 | 3/2012 | Holsing' |
| 2012/0062714 A1 | 3/2012 | Liu |
| 2012/0065481 A1 | 3/2012 | Hunter |
| 2012/0069167 A1 | 3/2012 | Liu et al. |
| 2012/0071782 A1 | 3/2012 | Patil et al. |
| 2012/0082351 A1 | 4/2012 | Higgins et al. |
| 2012/0120305 A1 | 5/2012 | Takahashi |
| 2012/0165656 A1 | 6/2012 | Montag |
| 2012/0172712 A1 | 7/2012 | Bar-Tai |
| 2012/0191079 A1 | 7/2012 | Moll et al. |
| 2012/0209069 A1 | 8/2012 | Popovic |
| 2012/0215094 A1 | 8/2012 | Rahimian et al. |
| 2012/0219185 A1 | 8/2012 | Hu |
| 2012/0289777 A1 | 11/2012 | Chopra |
| 2012/0289783 A1 | 11/2012 | Duindam et al. |
| 2012/0302869 A1 | 11/2012 | Koyrakh |
| 2013/0060146 A1 | 3/2013 | Yang et al. |
| 2013/0144116 A1 | 6/2013 | Cooper et al. |
| 2013/0165945 A9 | 6/2013 | Roelle |
| 2013/0204124 A1 | 8/2013 | Duindam |
| 2013/0225942 A1 | 8/2013 | Holsing |
| 2013/0243153 A1 | 9/2013 | Sra |
| 2013/0246334 A1 | 9/2013 | Ahuja |
| 2013/0259315 A1 | 10/2013 | Angot et al. |
| 2013/0303892 A1 | 11/2013 | Zhao |
| 2013/0345718 A1 | 12/2013 | Crawford |
| 2014/0058406 A1 | 2/2014 | Tsekos |
| 2014/0072192 A1 | 3/2014 | Reiner |
| 2014/0107390 A1 | 4/2014 | Brown |
| 2014/0114180 A1 | 4/2014 | Jain |

(56) References Cited

U.S. PATENT DOCUMENTS

| | | |
|---|---|---|
| 2014/0148808 A1 | 4/2014 | Inkpen et al. |
| 2014/0142591 A1 | 5/2014 | Alvarez et al. |
| 2014/0180063 A1 | 6/2014 | Zhao |
| 2014/0235943 A1 | 8/2014 | Paris |
| 2014/0243849 A1 | 8/2014 | Saglam |
| 2014/0257746 A1 | 9/2014 | Dunbar et al. |
| 2014/0264081 A1 | 9/2014 | Walker et al. |
| 2014/0275988 A1 | 9/2014 | Walker et al. |
| 2014/0276033 A1 | 9/2014 | Brannan |
| 2014/0276937 A1 | 9/2014 | Wong et al. |
| 2014/0296655 A1 | 10/2014 | Akhbardeh et al. |
| 2014/0296657 A1 | 10/2014 | Izmirli |
| 2014/0309527 A1 | 10/2014 | Namati et al. |
| 2014/0309649 A1 | 10/2014 | Alvarez et al. |
| 2014/0343416 A1 | 11/2014 | Panescu |
| 2014/0350391 A1 | 11/2014 | Prisco et al. |
| 2014/0357984 A1 | 12/2014 | Wallace et al. |
| 2014/0364739 A1 | 12/2014 | Liu |
| 2014/0364870 A1 | 12/2014 | Alvarez et al. |
| 2015/0051482 A1 | 2/2015 | Liu et al. |
| 2015/0051592 A1 | 2/2015 | Kintz |
| 2015/0054929 A1 | 2/2015 | Ito et al. |
| 2015/0057498 A1 | 2/2015 | Akimoto |
| 2015/0073266 A1 | 3/2015 | Brannan |
| 2015/0119638 A1 | 4/2015 | Yu et al. |
| 2015/0141808 A1 | 5/2015 | Elhawary |
| 2015/0141858 A1 | 5/2015 | Razavi |
| 2015/0142013 A1 | 5/2015 | Tanner et al. |
| 2015/0164594 A1 | 6/2015 | Romo et al. |
| 2015/0164596 A1 | 6/2015 | Romo |
| 2015/0223725 A1 | 8/2015 | Engel |
| 2015/0223897 A1 | 8/2015 | Kostrzewski et al. |
| 2015/0223902 A1 | 8/2015 | Walker et al. |
| 2015/0255782 A1 | 9/2015 | Kim et al. |
| 2015/0265368 A1 | 9/2015 | Chopra |
| 2015/0265807 A1* | 9/2015 | Park .................. A61B 5/06 600/424 |
| 2015/0275986 A1 | 10/2015 | Cooper |
| 2015/0287192 A1 | 10/2015 | Sasaki |
| 2015/0297133 A1 | 10/2015 | Jouanique-Dubuis et al. |
| 2015/0305650 A1 | 10/2015 | Hunter |
| 2015/0313503 A1 | 11/2015 | Seibel et al. |
| 2015/0335480 A1 | 11/2015 | Alvarez et al. |
| 2016/0000302 A1 | 1/2016 | Brown |
| 2016/0000414 A1 | 1/2016 | Brown |
| 2016/0000520 A1 | 1/2016 | Lachmanovich |
| 2016/0001038 A1 | 1/2016 | Romo et al. |
| 2016/0008033 A1 | 1/2016 | Hawkins et al. |
| 2016/0111192 A1 | 4/2016 | Suzara |
| 2016/0128992 A1 | 5/2016 | Hudson |
| 2016/0183841 A1 | 6/2016 | Duindam et al. |
| 2016/0199134 A1 | 7/2016 | Brown et al. |
| 2016/0206389 A1 | 7/2016 | Miller |
| 2016/0213432 A1 | 7/2016 | Flexman |
| 2016/0228032 A1 | 8/2016 | Walker et al. |
| 2016/0270865 A1 | 9/2016 | Landey et al. |
| 2016/0287279 A1 | 10/2016 | Bovay et al. |
| 2016/0287346 A1 | 10/2016 | Hyodo et al. |
| 2016/0314710 A1 | 10/2016 | Jarc |
| 2016/0331469 A1 | 11/2016 | Hall et al. |
| 2016/0360947 A1 | 12/2016 | Iida |
| 2016/0372743 A1 | 12/2016 | Cho et al. |
| 2016/0374541 A1 | 12/2016 | Agrawal et al. |
| 2017/0007337 A1 | 1/2017 | Dan |
| 2017/0023423 A1 | 1/2017 | Jackson |
| 2017/0055851 A1 | 3/2017 | Al-Ali |
| 2017/0079725 A1 | 3/2017 | Hoffman |
| 2017/0079726 A1 | 3/2017 | Hoffman |
| 2017/0084027 A1* | 3/2017 | Mintz .................. G06T 7/0012 |
| 2017/0100199 A1 | 4/2017 | Yu et al. |
| 2017/0119413 A1 | 5/2017 | Romo |
| 2017/0119481 A1 | 5/2017 | Romo et al. |
| 2017/0165011 A1 | 6/2017 | Bovay et al. |
| 2017/0172673 A1 | 6/2017 | Yu et al. |
| 2017/0189118 A1 | 7/2017 | Chopra |
| 2017/0202627 A1 | 7/2017 | Sramek et al. |
| 2017/0209073 A1 | 7/2017 | Sramek et al. |
| 2017/0215808 A1 | 8/2017 | Shimol et al. |
| 2017/0215969 A1 | 8/2017 | Zhai et al. |
| 2017/0215978 A1 | 8/2017 | Wallace et al. |
| 2017/0238807 A9 | 8/2017 | Veritkov et al. |
| 2017/0258366 A1 | 9/2017 | Tupin |
| 2017/0290631 A1 | 10/2017 | Lee et al. |
| 2017/0296032 A1 | 10/2017 | Li |
| 2017/0296202 A1 | 10/2017 | Brown |
| 2017/0303941 A1 | 10/2017 | Eisner |
| 2017/0325896 A1 | 11/2017 | Donhowe |
| 2017/0333679 A1 | 11/2017 | Jiang |
| 2017/0340241 A1 | 11/2017 | Yamada |
| 2017/0340396 A1 | 11/2017 | Romo et al. |
| 2017/0348067 A1 | 12/2017 | Krimsky |
| 2017/0360508 A1 | 12/2017 | Germain et al. |
| 2017/0367782 A1 | 12/2017 | Schuh et al. |
| 2018/0025666 A1 | 1/2018 | Ho et al. |
| 2018/0055576 A1 | 3/2018 | Koyrakh |
| 2018/0055582 A1 | 3/2018 | Krimsky |
| 2018/0098690 A1 | 4/2018 | Iwaki |
| 2018/0177383 A1 | 6/2018 | Noonan et al. |
| 2018/0177556 A1 | 6/2018 | Noonan et al. |
| 2018/0214011 A1 | 8/2018 | Graetzel et al. |
| 2018/0217734 A1 | 8/2018 | Koenig et al. |
| 2018/0221038 A1 | 8/2018 | Noonan et al. |
| 2018/0221039 A1 | 8/2018 | Shah |
| 2018/0240237 A1 | 8/2018 | Donhowe et al. |
| 2018/0250083 A1 | 9/2018 | Schuh et al. |
| 2018/0263714 A1 | 9/2018 | Kostrzewski |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0286108 A1 | 10/2018 | Hirakawa |
| 2018/0289243 A1 | 10/2018 | Landey et al. |
| 2018/0289431 A1 | 10/2018 | Draper et al. |
| 2018/0308232 A1 | 10/2018 | Gliner |
| 2018/0308247 A1 | 10/2018 | Gupta |
| 2018/0325499 A1 | 11/2018 | Landey et al. |
| 2018/0333044 A1 | 11/2018 | Jenkins |
| 2018/0360435 A1 | 12/2018 | Romo |
| 2018/0368920 A1 | 12/2018 | Ummalaneni |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0046814 A1 | 2/2019 | Senden et al. |
| 2019/0066314 A1 | 2/2019 | Abhari |
| 2019/0083183 A1 | 3/2019 | Moll et al. |
| 2019/0086349 A1 | 3/2019 | Nelson |
| 2019/0110839 A1 | 4/2019 | Rafii-Tari et al. |
| 2019/0151148 A1 | 4/2019 | Alvarez et al. |
| 2019/0125164 A1 | 5/2019 | Roelle et al. |
| 2019/0142519 A1 | 5/2019 | Siemionow et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0287673 A1 | 9/2019 | Michihata |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tari |

(56) References Cited

U.S. PATENT DOCUMENTS

| | | |
|---|---|---|
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0022767 A1 | 1/2020 | Hill |
| 2020/0038123 A1 | 2/2020 | Graetzel |
| 2020/0039086 A1 | 2/2020 | Meyer |
| 2020/0046434 A1 | 2/2020 | Graetzel |
| 2020/0054405 A1 | 2/2020 | Schuh |
| 2020/0054408 A1 | 2/2020 | Schuh et al. |
| 2020/0060516 A1 | 2/2020 | Baez |
| 2020/0078103 A1 | 3/2020 | Duindam |
| 2020/0085516 A1 | 3/2020 | DeFonzo |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0155084 A1 | 5/2020 | Walker |
| 2020/0170630 A1 | 6/2020 | Wong |
| 2020/0170720 A1 | 6/2020 | Ummalaneni |
| 2020/0171660 A1 | 6/2020 | Ho |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |
| 2020/0281787 A1 | 9/2020 | Ruiz |
| 2020/0297437 A1 | 9/2020 | Schuh |
| 2020/0297444 A1 | 9/2020 | Camarillo |
| 2020/0305983 A1 | 10/2020 | Yampolsky |
| 2020/0305989 A1 | 10/2020 | Schuh |
| 2020/0305992 A1 | 10/2020 | Schuh |
| 2020/0315717 A1 | 10/2020 | Bovay |
| 2020/0315723 A1 | 10/2020 | Hassan |
| 2020/0323596 A1 | 10/2020 | Moll |
| 2020/0330167 A1 | 10/2020 | Romo |
| 2020/0345216 A1 | 11/2020 | Jenkins |
| 2020/0352420 A1 | 11/2020 | Graetzel |
| 2020/0360183 A1 | 11/2020 | Alvarez |
| 2020/0367726 A1 | 11/2020 | Landey et al. |
| 2020/0367981 A1 | 11/2020 | Ho et al. |
| 2020/0375678 A1 | 12/2020 | Wallace |

FOREIGN PATENT DOCUMENTS

| | | |
|---|---|---|
| CN | 102316817 | 1/2012 |
| CN | 102458295 | 5/2012 |
| CN | 102946801 | 2/2013 |
| CN | 102973317 | 3/2013 |
| CN | 103705307 | 4/2014 |
| CN | 103735313 | 4/2014 |
| CN | 103813748 | 5/2014 |
| CN | 104758066 | 7/2015 |
| CN | 105559850 | 5/2016 |
| CN | 105559886 | 5/2016 |
| CN | 105611881 | 5/2016 |
| CN | 106455908 | 2/2017 |
| CN | 106821498 | 6/2017 |
| CN | 104931059 | 9/2018 |
| EP | 3 025 630 | 6/2016 |
| JP | 2003265409 A | 9/2003 |
| JP | 200489484 | 3/2004 |
| KR | 10-2014-0009359 | 1/2014 |
| KR | 10-1713676 B1 | 3/2017 |
| RU | 2569699 C2 | 11/2015 |
| WO | WO 05/087128 | 9/2005 |
| WO | WO 06/051523 | 5/2006 |
| WO | WO 09/097461 | 6/2007 |
| WO | WO 15/089013 | 6/2015 |
| WO | WO 16/077419 | 5/2016 |
| WO | WO 16/203727 | 12/2016 |
| WO | WO 17/030916 | 2/2017 |
| WO | WO 17/036774 | 3/2017 |
| WO | WO 17/048194 | 3/2017 |
| WO | WO 17/066108 | 4/2017 |
| WO | WO 17/146890 | 8/2017 |
| WO | WO 17/167754 | 10/2017 |

OTHER PUBLICATIONS

Ren, Hongliang, et al. "Multisensor data fusion in an integrated tracking system for endoscopic surgery." IEEE Transactions on Information Technology in Biomedicine 16.1 (2011): 106-111. (Year: 2011).*

Bellemare, Marc-Emmanuel, et al. "Depth-map-based scene analysis for active navigation." Medical Imaging 1999: Physiology and Function from Multidimensional Imags. vol. 3660. International Socity for Optics and Photonics, 1999. (Year: 1999).*

Ciuti et al., 2012, Intra-operative monocular 30 reconstruction for image-guided navigation in active locomotion capsule endoscopy. Biomedical Robotics and Biomechatronics (Biorob), 4th IEEE Ras & Embs International Conference on IEEE.

Fallavollita et al., 2010, Acquiring multiview C-arm images to assist cardiac ablation procedures, EURASIP Journal on Image and Video Processing, vol. 2010, Article ID 871408, pp. 1-10.

Haigron et al., 2004, Depth-map-based scene analysis for active navigation in virtual angioscopy, IEEE Transactions on Medical Imaging, 23(11):1380-1390.

Kumar et al., 2014, Stereoscopic visualization of laparoscope image using depth information from 3D model, Computer methods and programs in biomedicine 113(3):862-868.

Livatino et al., 2015, Stereoscopic visualization and 3-D technologies in medical endoscopic teleoperation, IEEE.

Luo et al., 2010, Modified hybrid bronchoscope tracking based on sequential monte carlo sampler: Dynamic phantom validation, Asian Conference on Computer Vision. Springer, Berlin, Heidelberg.

Mourgues et al., 2002, Flexible calibration of actuated stereoscopic endoscope for overlay inrobot assisted surgery, International Conference on Medical Image Computing and Computer-Assisted Intervention. Springer, Berlin, Heidelberg.

Nadeem et al., 2016, Depth Reconstruction and Computer-Aided Polyp Detection in Optical Colonoscopy Video Frames, arXiv preprint arXiv:1609.01329.

Point Cloud, Sep. 10, 2010, Wikipedia, 2 pp.

Racadio et al., Dec. 2007, Live 3D guidance in the interventional radiology suite, AJR, 189:W357-W364.

Sato et al., 2016, Techniques of stapler-based navigational thoracoscopic segmentectomy using virtual assisted lung mapping (VAL-MAP), Journal of Thoracic Disease, 8(Suppl 9):S716.

Shen et al., 2015, Robust camera localisation with depth reconstruction for bronchoscopic navigation. International Journal of Computer Assisted Radiology and Surgery, 10(6):801-813.

Solheim et al., May 14, 2009, Navigated resection of giant intracranial meningiomas based on intraoperative 3D ultrasound, Acta Neurochir, 151:1143-1151.

Song et al., 2012, Autonomous and stable tracking of endoscope instrument tools with monocular camera, Advanced Intelligent Mechatronics (AIM), 2012 IEEE-ASME International Conference on. IEEE.

Verdaasdonk et al., Jan. 23, 2012, Effect of microsecond pulse length and tip shape on explosive bubble formation of 2.78 μm Er,Cr;YSGG and 2.94 μm Er:YAG laser, Proceedings of SPIE, vol. 8221, 12.

Yip et al., 2012, Tissue tracking and registration for image-guided surgery, IEEE transactions on medical imaging 31(11):2169-2182.

(56) References Cited

OTHER PUBLICATIONS

Zhou et al., 2010, Synthesis of stereoscopic views from monocular endoscopic videos, Computer Vision and Pattern Recognition Workshops (CVPRW), 2010 IEEE Computer Society Conference on IEEE.
International Search Report and Written Opinion dated Sep. 12, 2018 in application No. PCT/US18/36329.
Mayo Clinic, Robotic Surgery, https://www.mayoclinic.org/tests-procedures/robotic-surgery/about/pac-20394974?p=1, downloaded from the internet on Jul. 12, 2018, 2 pp.
Kiraly et al, 2002, Three-dimensional Human Airway Segmentation Methods for Clinical Virtual Bronchoscopy, Acad Radiol, 9:1153-1168.
Kiraly et al., Sep. 2004, Three-dimensional path planning for virtual bronchoscopy, IEEE Transactions on Medical Imaging, 23(9):1365-1379.
Konen et al., 1998, The VN-project: endoscopic image processing for neurosurgery, Computer Aided Surgery, 3:1-6.
Shi et al., Sep. 14-18, 2014, Simultaneous catheter and environment modeling for trans-catheter aortic valve implantation, IEEE/RSJ International Conference on Intelligent Robots and Systems, pp. 2024-2029.
Solomon et al., Dec. 2000, Three-dimensional CT-Guided Bronchoscopy With a Real-Time Electromagnetic Position Sensor A Comparison of Two Image Registration Methods, Chest, 118(6):1783-1787.
Vemuri et al., Dec. 2015, Inter-operative biopsy site relocations in endoluminal surgery, IEEE Transactions on Biomedical Engineering, Institute of Electrical and Electronics Engineers, <10.1109/TBME.2015.2503981>. <hal-01230752>.
Wilson et al., 2008, a buyer's guide to electromagnetic tracking systems for clinical applications, Proc. of SPCI, 6918:69182B-1 p. 6918B-11.
Al-Ahmad et al., dated 2005, Early experience with a computerized robotically controlled catheter system, Journal of Interventional Cardiac Electrophysiology, 12:199-202.
Gutierrez et al., Mar. 2008, A practical global distortion correction method for an image intensifier based x-ray fluoroscopy system, Med. Phys, 35(3):997-1007.
Hansen Medical, Inc. 2005, System Overview, product brochure, 2 pp., dated as available at http://hansenmedical.com/system.aspx on Jul. 14, 2006 (accessed Jun. 25, 2019 using the internet archive way back machine).
Hansen Medical, Inc. Bibliography, product brochure, 1 p., dated as available at http://hansenmedical.com/bibliography.aspx on Jul. 14, 2006 (accessed Jun. 25, 2019 using the internet archive way back machine).
Hansen Medical, Inc. dated 2007, Introducing the Sensei Robotic Catheter System, product brochure, 10 pp.
Hansen Medical, Inc. dated 2009, Sensei X Robotic Catheter System, product brochure, 5 pp.
Hansen Medical, Inc. Technology Advantages, product brochure, 1 p., dated as available at http://hansenmedical.com/advantages.aspx on Jul. 13, 2006 (accessed Jun. 25, 2019 using the internet archive way back machine).
Marrouche et al., dated May 6, 2005, AB32-1, Preliminary human experience using a novel robotic catheter remote control, Heart Rhythm, 2(5):S63.
Oh et al., dated May 2005, P5-75, Novel robotic catheter remote control system: safety and accuracy in delivering RF Lesions in all 4 cardiac chambers, Heart Rhythm, 2(5):S277-S278.
Reddy et al., May 2005, P1-53. Porcine pulmonary vein ablation using a novel robotic catheter control system and real-time integration of CT imaging with electroanatomical mapping, Hearth Rhythm, 2(5):S121.
Slepian, dated 2010, Robotic Catheter Intervention: the Hansen Medical Sensei Robot Catheter System, PowerPoint presentation, 28 pp.
JP Office Action for appl No. 2019571226, dated Aug. 25, 2021, 11 pages.

\* cited by examiner

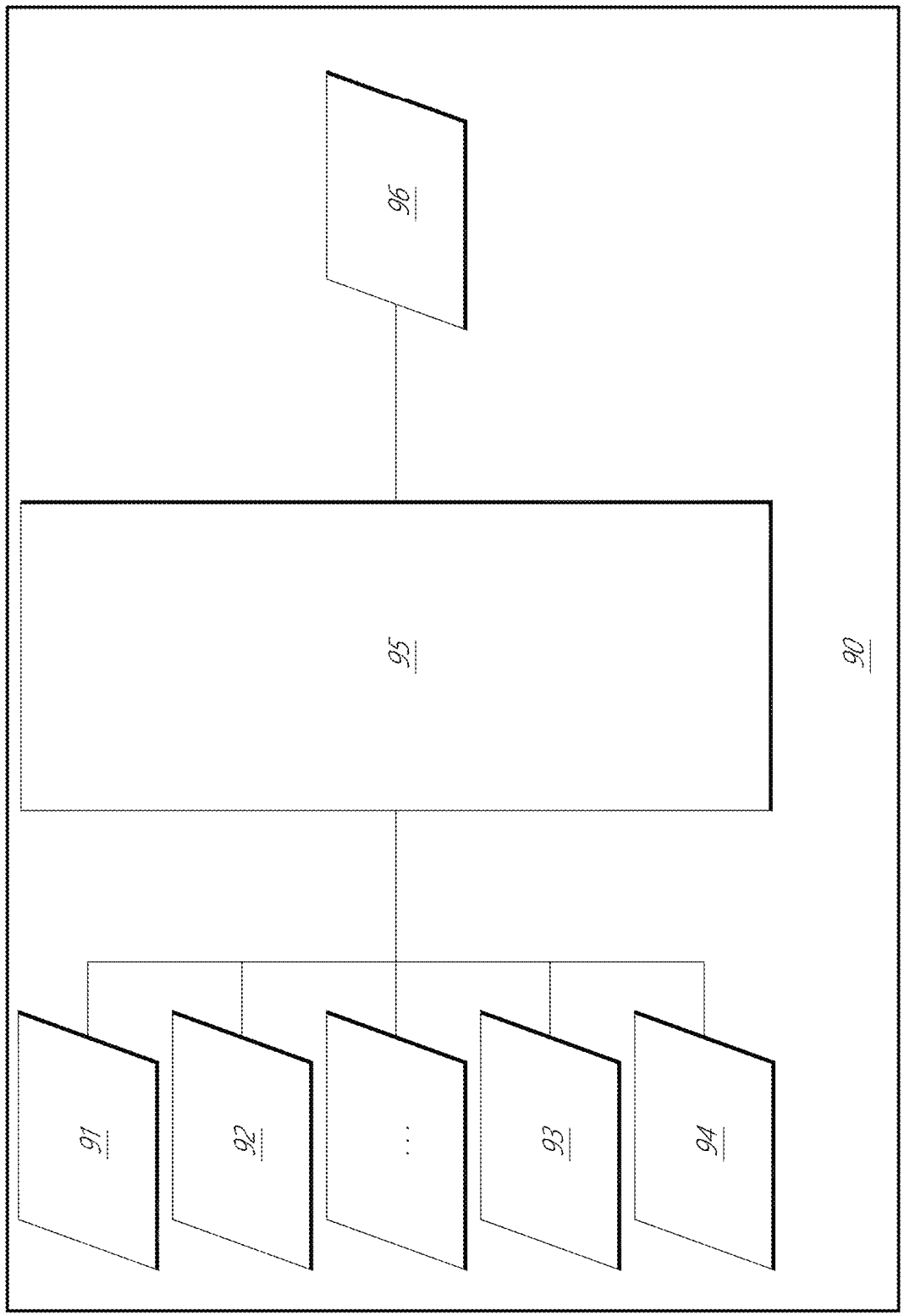

US 11,278,357 B2

ROBOTIC SYSTEMS FOR DETERMINING AN ANGULAR DEGREE OF FREEDOM OF A MEDICAL DEVICE IN LUMINAL NETWORKS

CROSS-REFERENCE TO RELATED APPLICATION(S)

The present application is a continuation of U.S. patent application Ser. No. 16/023,877, filed on Jun. 29, 2018, entitled "ROBOTIC SYSTEMS FOR DETERMINING A ROLL OF A MEDICAL DEVICE IN LUMINAL NETWORKS", which is a continuation of U.S. patent application Ser. No. 15/631,691, filed on Jun. 23, 2017, entitled "AUTOMATICALLY-INITIALIZED ROBOTIC SYSTEMS FOR NAVIGATION OF LUMINAL NETWORKS," the content of each of these applications of which is hereby incorporated by reference herein in its entirety.

TECHNICAL FIELD

The systems and methods disclosed herein are directed to medical procedures, and more particularly to navigation-assisted medical devices.

BACKGROUND

Medical procedures such as endoscopy (e.g., bronchoscopy) may involve accessing and visualizing the inside of a patient's lumen (e.g., airways) for diagnostic and/or therapeutic purposes. During a procedure, a flexible tubular tool such as, for example, an endoscope, may be inserted into the patient's body and an instrument can be passed through the endoscope to a tissue site identified for diagnosis and/or treatment.

Bronchoscopy is a medical procedure that allows a physician to examine the inside conditions of a patient's lung airways, such as bronchi and bronchioles. During the medical procedure, a thin, flexible tubular tool, known as a bronchoscope, may be inserted into the patient's mouth and passed down the patient's throat into his/her lung airways towards a tissue site identified for subsequent diagnosis and treatment. The bronchoscope can have an interior lumen (a "working channel") providing a pathway to the tissue site, and catheters and various medical tools can be inserted through the working channel to the tissue site.

SUMMARY

An endoscopy navigation system can use a fusion of different sensing modalities (e.g., scope imaging data, electromagnetic (EM) position data, robotic position data, etc.) modeled, for example, through adaptively-adjusted probabilities. A probabilistic navigation approach or other navigation approach may depend on an initial estimate of "where" the tip of the endoscope is—for example, an estimate of which airway, how deep into this airway, and how much roll in this airway—in order to begin tracking the tip of the endoscope. Some endoscopy techniques can involve a three-dimensional (3D) model of a patient's anatomy, and can guide navigation using an EM field and position sensors. At the outset of a procedure, the precise alignment (e.g., registration) between the virtual space of the 3D model, the physical space of the patient's anatomy represented by the 3D model, and the EM field may be unknown. As such, prior to generating a registration or in situations where the accuracy of an existing registration is in question, endoscope positions within the patient's anatomy cannot be mapped with precision to corresponding locations within the 3D model.

Typically, a navigation system requires the physician to undergo a series of initialization steps in order to generate this initial estimate. This can involve, for example, instructing the physician to position a bronchoscope at a number of specific positions and orientations relative to landmark(s) within the bronchial tree (e.g., by touching the main carina, the left carina, and the right carina). Another option requires the physician to perform an initial airway survey, for example, starting in the mid-trachea and entering each lobe while attempting to maintain a centered position of the bronchoscope tip within each airway.

Such initialization steps can provide an initial estimate of the endoscope position; however, such an approach may have several potential drawbacks including adding additional time requirements to the beginning of the procedure. Another potential drawback relates to the fact that, after the initialization has been completed and tracking is occurring, an adverse event (e.g., patient coughing, dynamic airway collapse) can create uncertainty about the actual position of the endoscope. This can necessitate determination of a new "initial" position, and accordingly the navigation system may require the physician to navigate back to the trachea to re-perform the initialization steps. Such backtracking adds additional time requirements that can be particularly burdensome if the adverse event occurs after the endoscope has been navigated through the smaller peripheral airways toward a target site.

The aforementioned issues, among others, are addressed by the luminal network navigation systems and techniques described herein. The disclosed techniques can generate a 3D model of a virtual luminal network representing the patient's anatomical luminal network and can determine a number of locations within the virtual luminal network at which to position a virtual camera. The disclosed techniques can generate a virtual depth map representing distances between the internal surfaces of the virtual luminal network and the virtual camera positioned at a determined location. Features can be extracted from these virtual depth maps, for example, peak-to-peak distance in the case of a virtual depth map representing an airway bifurcation, and the extracted features can be stored in association with the location of the virtual camera. During the medical procedure, the distal end of an endoscope can be provided with an imaging device, and the disclosed navigation techniques can generate a depth map based on image data received from the imaging devices. The disclosed techniques can derive features from the generated depth map, calculate correspondence between the extracted features with the stored features extracted from one of the virtual depth maps, and then use the associated virtual camera location as the initial position of the distal end of the instrument. Beneficially, such techniques allow a probabilistic navigation system (or other navigation systems) to obtain an initial estimate of scope position without requiring the manual initialization steps described above. In addition, the disclosed techniques can be used throughout a procedure to refine registration and, in some embodiments, can provide an additional "initial estimate" after an adverse event without requiring navigation back through the luminal network to a landmark anatomical feature.

Accordingly, one aspect relates to a method of facilitating navigation of an anatomical luminal network of a patient, the method, executed by a set of one or more computing devices, comprising receiving imaging data captured by an imaging device at a distal end of an instrument positioned within the anatomical luminal network; accessing a virtual feature derived from a virtual image simulated from a viewpoint of a virtual imaging device positioned at a virtual location within a virtual luminal network representative of the anatomical luminal network; calculating a correspondence between a feature derived from the imaging data and the virtual feature derived from the virtual image; and determining a pose of the distal end of the instrument within the anatomical luminal network based on the virtual location associated with the virtual feature.

In some embodiments, the method further comprises generating a depth map based on the imaging data, wherein the virtual feature is derived from a virtual depth map associated with the virtual image, and wherein calculating the correspondence is based at least partly on correlating one or more features of the depth map and one or more features of the virtual depth map.

In some embodiments, the method further comprises generating the depth map by calculating, for each pixel of a plurality of pixels of the imaging data, a depth value representing an estimated distance between the imaging device and a tissue surface within the anatomical luminal network corresponding to the pixel; identifying a first pixel of the plurality of pixels corresponding to a first depth criterion in the depth map and a second pixel of the plurality of pixels corresponding to a second depth criterion in the depth map; calculating a first value representing a distance between the first and second pixels; wherein the virtual depth map comprises, for each virtual pixel of a plurality of virtual pixels, a virtual depth value representing a virtual distance between the virtual imaging device and a portion of the virtual luminal network represented by the virtual pixel, and wherein accessing the virtual feature derived from the virtual image comprises accessing a second value representing a distance between first and second depth criteria in the virtual depth map; and calculating the correspondence based on comparing the first value to the second value.

In some embodiments, the method further comprises accessing a plurality of values representing distances between first and second depth criteria in a plurality of virtual depth maps each representing a different one of a plurality of virtual locations within the virtual luminal network; and calculating the correspondence based on the second value corresponding more closely to the first value than other values of the plurality of values. In some embodiments the anatomical luminal network comprises airways and the imaging data depicts a bifurcation of the airways, and the method further comprises identifying one of the first and second depth criteria as a right bronchus in each of the depth map and the virtual depth map; and determining a roll of the instrument based on an angular distance between a first position of the right bronchus in the depth map and a second position of the right bronchus in the virtual depth map, wherein the pose of the distal end of the instrument within the anatomical luminal network comprises the determined roll.

In some embodiments, the method further comprises identifying three or more depth criteria in each of the depth map and the virtual depth map; determining a shape and location of a polygon connecting the depth criteria in each of the depth map and the virtual depth map; and calculating the correspondence based on comparing the shape and location of the polygon of the depth map to the shape and location of the polygon of the virtual depth map. In some embodiments, generating the depth map is based on photoclinometry.

In some embodiments, the method further comprises calculating a probabilistic state of the instrument within the anatomical luminal network based on a plurality of inputs comprising the position; and guiding navigation of the instrument through the anatomical luminal network based at least partly on the probabilistic state. In some embodiments, the method further comprises initializing a navigation system configured to calculate the probabilistic state and guide the navigation of the anatomical luminal network based on the probabilistic state, wherein the initializing of the navigation system comprises setting a prior of a probability calculator based on the position. In some embodiments, the method further comprises receiving additional data representing an updated pose of the distal end of the instrument; setting a likelihood function of the probability calculator based on the additional data; and determining the probabilistic state using the probability calculator based on the prior and the likelihood function.

In some embodiments, the method further comprises providing the plurality of inputs to a navigation system configured to calculate the probabilistic state, a first input comprising the pose of the distal end of the instrument and at least one additional input comprising one or both of robotic position data from a robotic system actuating movement of the instrument and data received from a position sensor at the distal end of the instrument; and calculating the probabilistic state of the instrument based on the first input and the at least one additional input.

In some embodiments, the method further comprises determining a registration between a coordinate frame of the virtual luminal network and a coordinate frame of an electromagnetic field generated around the anatomical luminal network based at least partly on the pose of the distal end of the instrument within the anatomical luminal network determined based on the calculated correspondence. In some embodiments, determining the position comprises determining a distance that the distal end of the instrument is advanced within a segment of the anatomical luminal network.

Another aspect relates to a system configured to facilitate navigation of an anatomical luminal network of a patient, the system comprising an imaging device at a distal end of an instrument; at least one computer-readable memory having stored thereon executable instructions; and one or more processors in communication with the at least one computer-readable memory and configured to execute the instructions to cause the system to at least receive imaging data captured by the imaging device with the distal end of the instrument positioned within the anatomical luminal network; access a virtual feature derived from a virtual image simulated from a viewpoint of a virtual imaging device positioned at a virtual location within a virtual luminal network representative of the anatomical luminal network; calculate a correspondence between a feature derived from the imaging data and the virtual feature derived from the virtual image; and determine a pose of the distal end of the instrument relative within the anatomical luminal network based on the virtual location associated with the virtual feature.

In some embodiments, the one or more processors are configured to execute the instructions to cause the system to at least generate a depth map based on the imaging data, wherein the virtual image represents a virtual depth map; and determine the correspondence based at least partly on correlating one or more features of the depth map and one or more features of the virtual depth map. In some embodiments, the one or more processors are configured to execute the instructions to cause the system to at least generate the depth map by calculating, for each pixel of a plurality of pixels of the imaging data, a depth value representing an estimated distance between the imaging device and a tissue surface within the anatomical luminal network corresponding to the pixel; identify a first pixel of the plurality of pixels corresponding to a first depth criterion in the depth map and a second pixel of the plurality of pixels corresponding to a second depth criterion in the depth map; calculate a first value representing a distance between the first and second pixels; wherein the virtual depth map comprises, for each virtual pixel of a plurality of virtual pixels, a virtual depth value representing a virtual distance between the virtual imaging device and a portion of the virtual luminal network represented by the virtual pixel, and wherein the feature derived from the virtual image comprises a second value representing a distance between first and second depth criteria in the virtual depth map; and determine the correspondence based on comparing the first value to the second value.

In some embodiments, the one or more processors are configured to execute the instructions to cause the system to at least access a plurality of values representing distances between first and second depth criteria in a plurality of virtual depth maps each representing a different one of a plurality of virtual locations within the virtual luminal network; and calculate the correspondence based on the second value corresponding more closely to the first value than other values of the plurality of values identify the second value as a closest match to the first value among the plurality of values. In some embodiments, the anatomical luminal network comprises airways and the imaging data depicts a bifurcation of the airways, and the one or more processors are configured to execute the instructions to cause the system to at least identify one of the first and second depth criteria as a right bronchus in each of the depth map and the virtual depth map; and determine a roll of the instrument based on an angular distance between a first position of the right bronchus in the depth map and a second position of the right bronchus in the virtual depth map, wherein the pose of the distal end of the instrument within the anatomical luminal network comprises the determined roll.

In some embodiments, the one or more processors are configured to execute the instructions to cause the system to at least identify three or more depth criteria in each of the depth map and the virtual depth map; determine a shape and location of a polygon connecting the three or more depth criteria in each of the depth map and the virtual depth map; and calculate the correspondence based on comparing the shape and location of the polygon of the depth map to the shape and location of the polygon of the virtual depth map. In some embodiments, the one or more processors are configured to execute the instructions to cause the system to at least generate the depth map based on photoclinometry.

In some embodiments, the one or more processors are configured to communicate with a navigation system, and wherein the one or more processors are configured to execute the instructions to cause the system to at least calculate a probabilistic state of the instrument within the anatomical luminal network using the navigation system based at least partly on a plurality of inputs comprising the position; and guide navigation of the instrument through the anatomical luminal network based at least partly on the probabilistic state calculated by the navigation system. Some embodiments of the system further comprise a robotic system configured to guide movements of the instrument during the navigation. In some embodiments, the plurality of inputs comprise robotic position data received from the robotic system, and wherein the one or more processors are configured to execute the instructions to cause the system to at least calculate the probabilistic state of the instrument using the navigation system based at least partly on the position and on the robotic position data. Some embodiments of the system further compirse a position sensor at the distal end of an instrument, the plurality of inputs comprise data received from the position sensor, and wherein the one or more processors are configured to execute the instructions to cause the system to at least calculate the probabilistic state of the instrument using the navigation system based at least partly on the position and on the data received from the position sensor. In some embodiments, the one or more processors are configured to execute the instructions to cause the system to at least determine a registration between a coordinate frame of the virtual luminal network and a coordinate frame of an electromagnetic field generated around the anatomical luminal network based at least partly on the position.

Another aspect relates to a non-transitory computer readable storage medium having stored thereon instructions that, when executed, cause at least one computing device to at least access a virtual three-dimensional model of internal surfaces of an anatomical luminal network of a patient; identify a plurality of virtual locations within the virtual three-dimensional model; for each virtual location of the plurality of virtual locations within the virtual three-dimensional model generate a virtual depth map representing virtual distances between a virtual imaging device positioned at the virtual location and a portion of the internal surfaces within a field of view of the virtual imaging device when positioned at the virtual location, and derive at least one virtual feature from the virtual depth map; and generate a database associating the plurality of virtual locations with the at least one virtual feature derived from the corresponding virtual depth map.

In some embodiments the instructions, when executed, cause the at least one computing device to at least provide the database to a navigation system configured to guide navigation of an instrument through the anatomical luminal network during a medical procedure. In some embodiments the instructions, when executed, cause the at least one computing device to at least access data representing an imaging device positioned at a distal end of the instrument; identify image capture parameters of the imaging device; and set virtual image capture parameters of the virtual imaging device to correspond to the image capture parameters of the imaging device.

In some embodiments the instructions, when executed, cause the at least one computing device to at least generate the virtual depth maps based on the virtual image capture parameters. In some embodiments the image capture parameters comprise one or more of field of view, lens distortion, focal length, and brightness shading.

In some embodiments the instructions, when executed, cause the at least one computing device to at least for each virtual location of the plurality of virtual locations identify first and second depth criteria in the virtual depth map, and calculate a value representing a distance between the first and second depth criteria; and create the database by associating the plurality of virtual locations with the corresponding value.

In some embodiments the instructions, when executed, cause the at least one computing device to at least for each virtual location of the plurality of virtual locations identify three or more depth criteria in the virtual depth map, and determine a shape and location of a polygon connecting the three or more depth criteria; and create the database by associating the plurality of virtual locations with the shape and location of the corresponding polygon. In some embodiments the instructions, when executed, cause the at least one computing device to at least generate a three-dimensional volume of data from a series of two-dimensional images representing the anatomical luminal network of the patient; and form the virtual three-dimensional model of the internal surfaces of the anatomical luminal network from the three-dimensional volume of data. In some embodiments the instructions, when executed, cause the at least one computing device to at least control a computed tomography imaging system to capture the series of two-dimensional images. In some embodiments the instructions, when executed, cause the at least one computing device to at least form the virtual three-dimensional model by applying volume segmentation to the three-dimensional volume of data.

Another aspect relates to a method of facilitating navigation of an anatomical luminal network of a patient, the method, executed by a set of one or more computing devices, comprising receiving a stereoscopic image set representing an interior of the anatomical luminal network; generating a depth map based on the stereoscopic image set; accessing a virtual feature derived from a virtual image simulated from a viewpoint of a virtual imaging device positioned at a location within a virtual luminal network; calculating a correspondence between a feature derived from the depth map and the virtual feature derived from the virtual image; and determining a pose of the distal end of the instrument within the anatomical luminal network based on the virtual location of associated with the virtual feature.

In some embodiments, generating the stereoscopic image set comprises positioning an imaging device at a distal end of an instrument at a first location within the anatomical luminal network; capturing a first image of an interior of the anatomical luminal network with the imaging device positioned at the first location; robotically controlling the imaging device to move a known distance to a second location within the anatomical luminal network; and capturing a second image of the interior of the anatomical luminal network with the imaging device positioned at the second location. In some embodiments, robotically controlling the imaging device to move the known distance comprises one or both of retracting the imaging device and angularly rolling the imaging device.

BRIEF DESCRIPTION OF THE DRAWINGS

The disclosed aspects will hereinafter be described in conjunction with the appended drawings and appendices, provided to illustrate and not to limit the disclosed aspects, wherein like designations denote like elements.

FIG. 15 depicts a block diagram illustrating a localization system that estimates a location of one or more elements of the robotic systems of FIGS. 1-10, such as the location of the instrument of FIGS. 13-14, in accordance to an example embodiment.

DETAILED DESCRIPTION

1. Overview

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroenterology, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
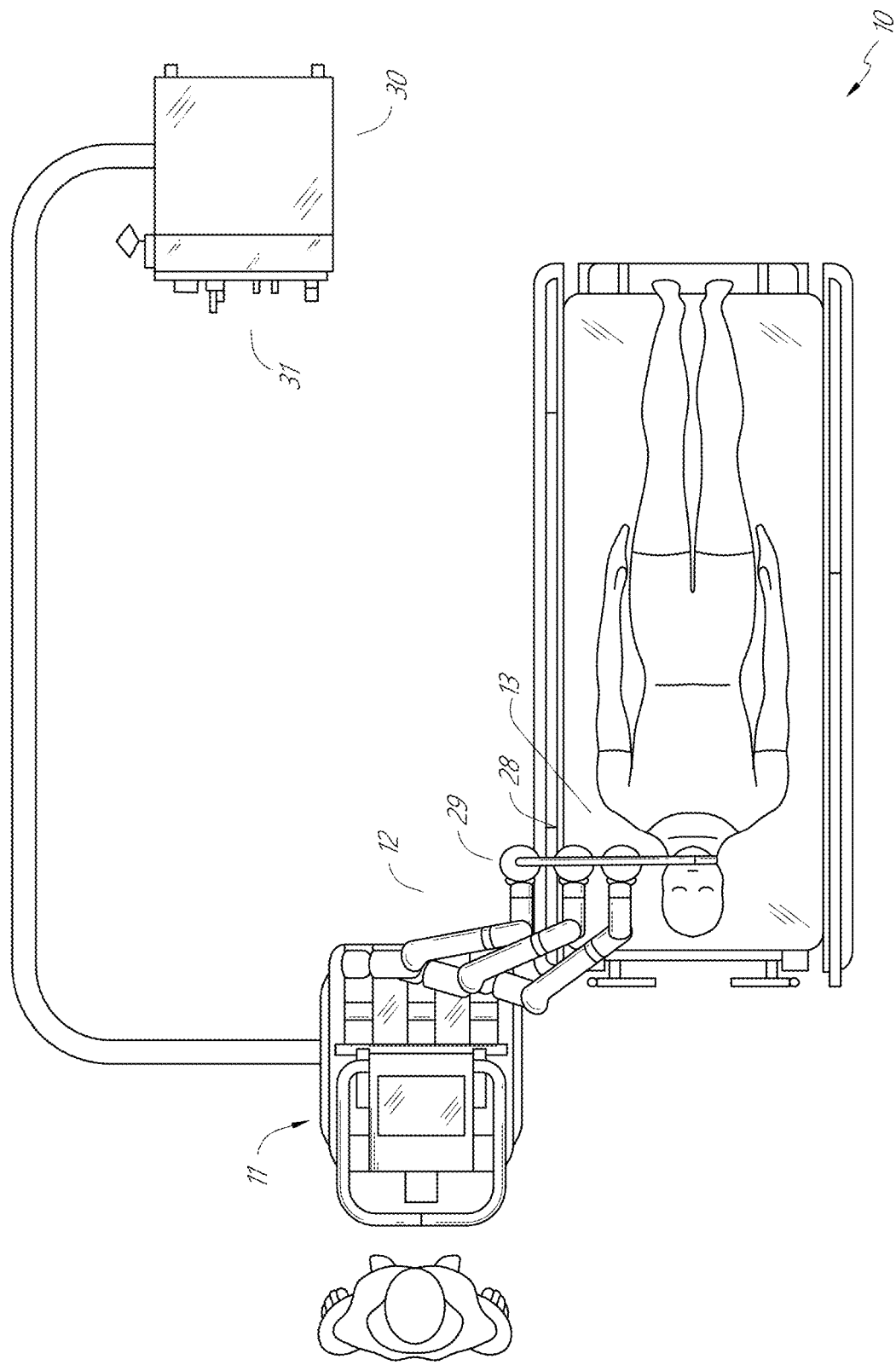
FIG. 1 illustrates an embodiment of a cart-based robotic system arranged for diagnostic and/or therapeutic bronchoscopy procedure(s).
Figure 2:
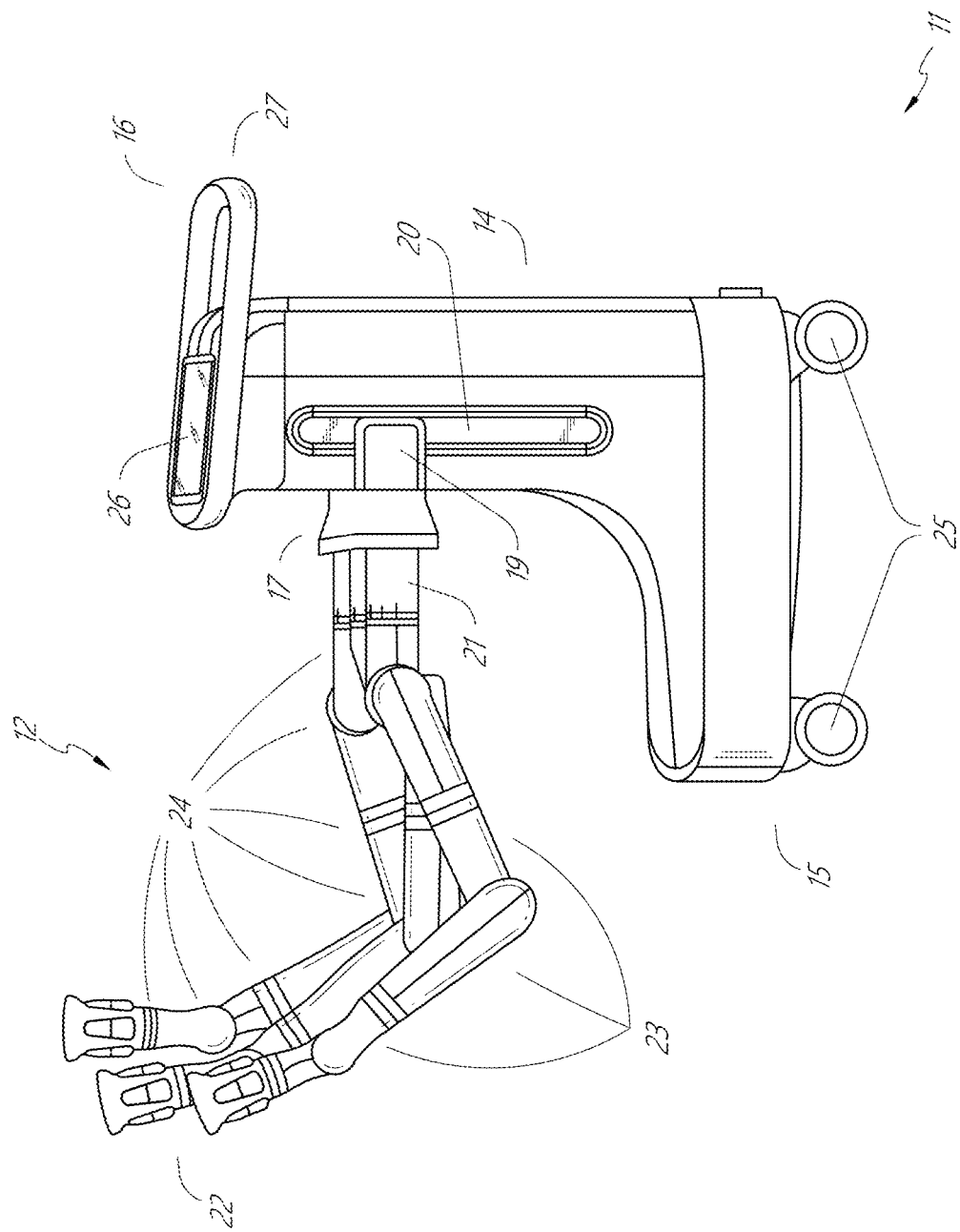
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments may need to be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position the physician may view the console 16, robotic arms 12, and patient while operating the console 16 from behind the cart 11. As shown, the console 16 also includes a handle 27 to assist with maneuvering and stabilizing cart 11.

Figure 3:
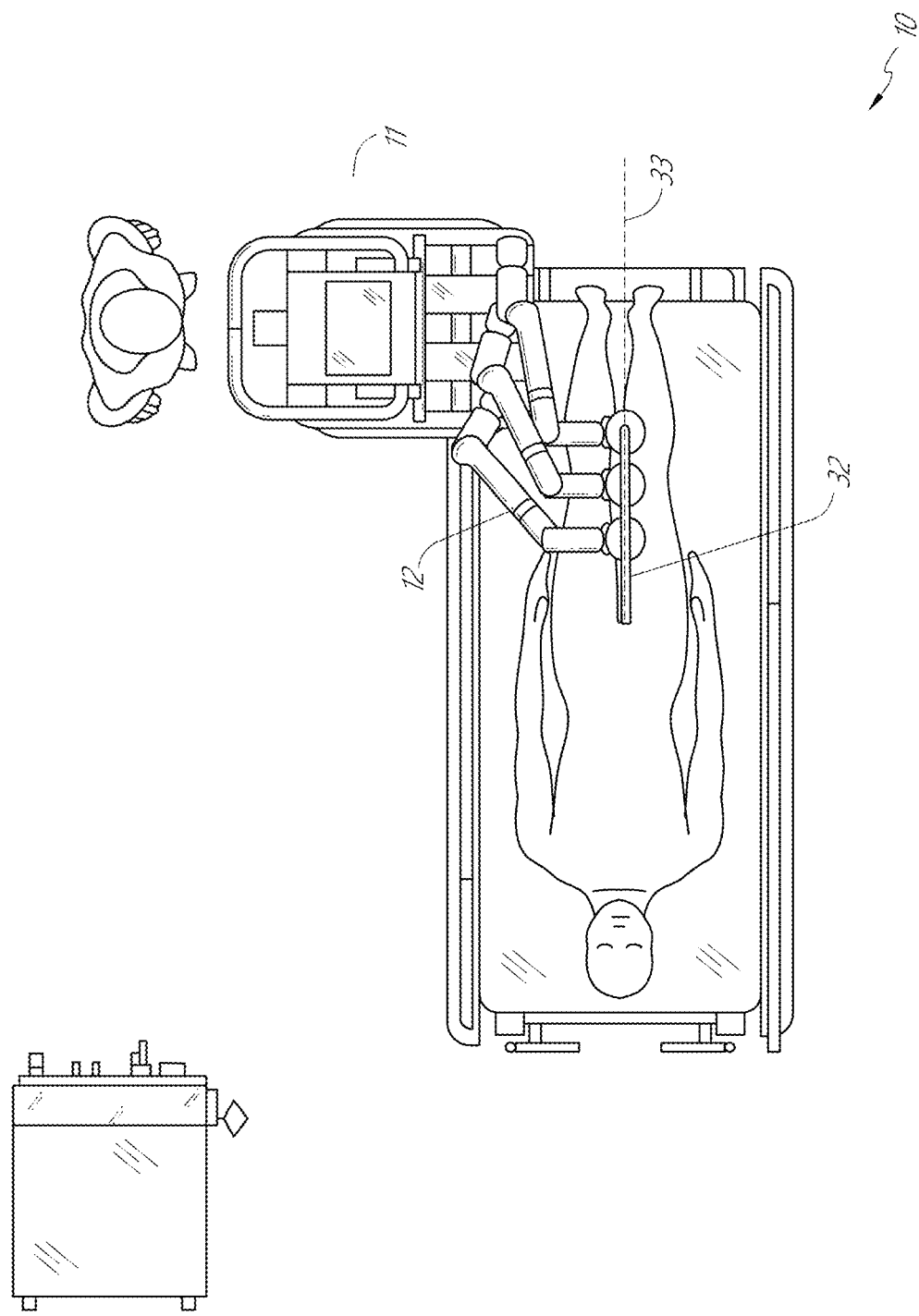
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using laser or ultrasonic lithotripsy device deployed down the working channel of the ureteroscope 32. After lithotripsy is complete, the resulting stone fragments may be removed using baskets deployed down the ureteroscope 32.

Figure 4:
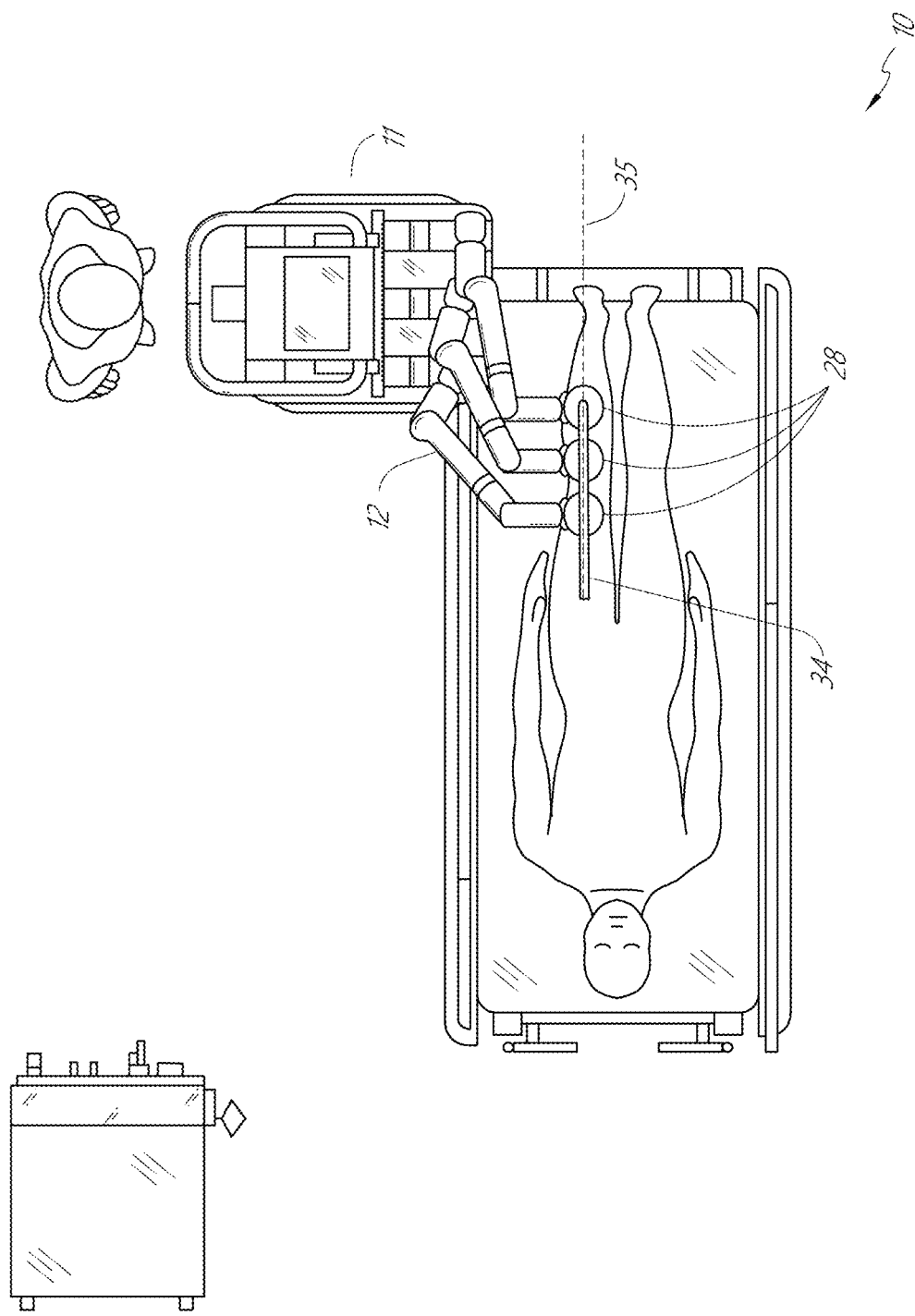
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such the cart 11 may deliver a medical instrument 34, such as a steerable catheter, to an access point in the femoral artery in the patient's leg. The femoral artery presents both a larger diameter for navigation as well as relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
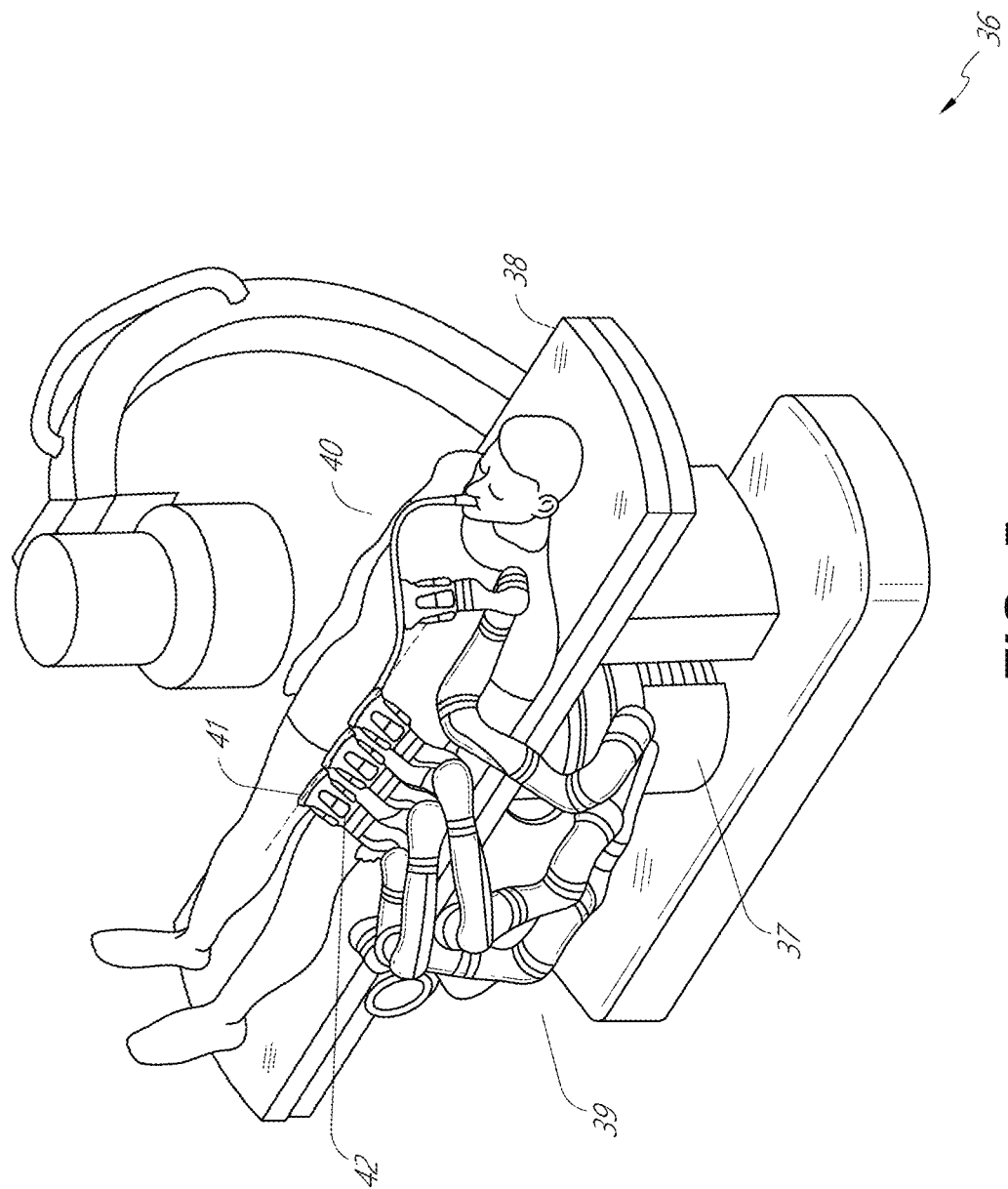
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
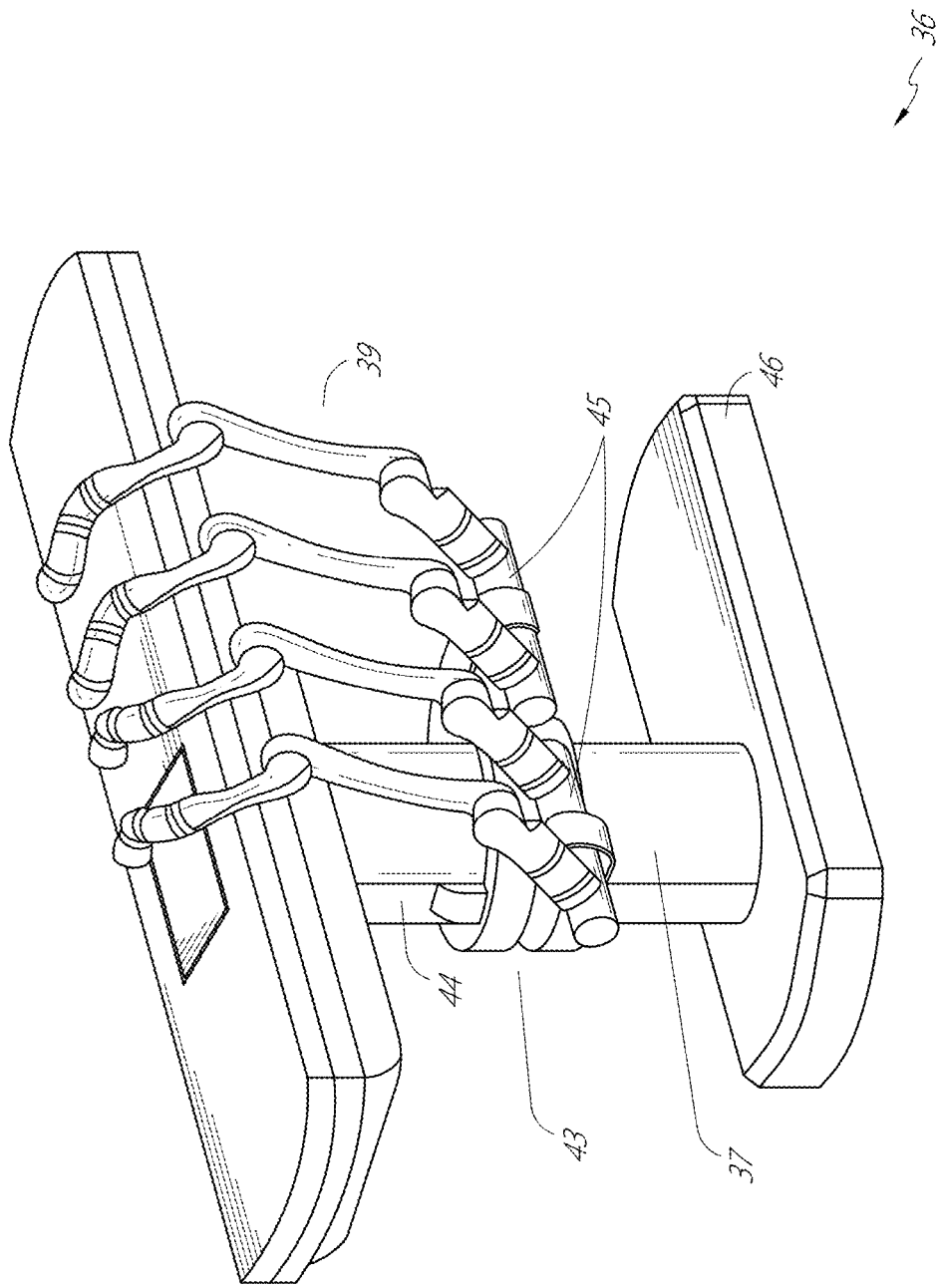
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient.

Figure 9:
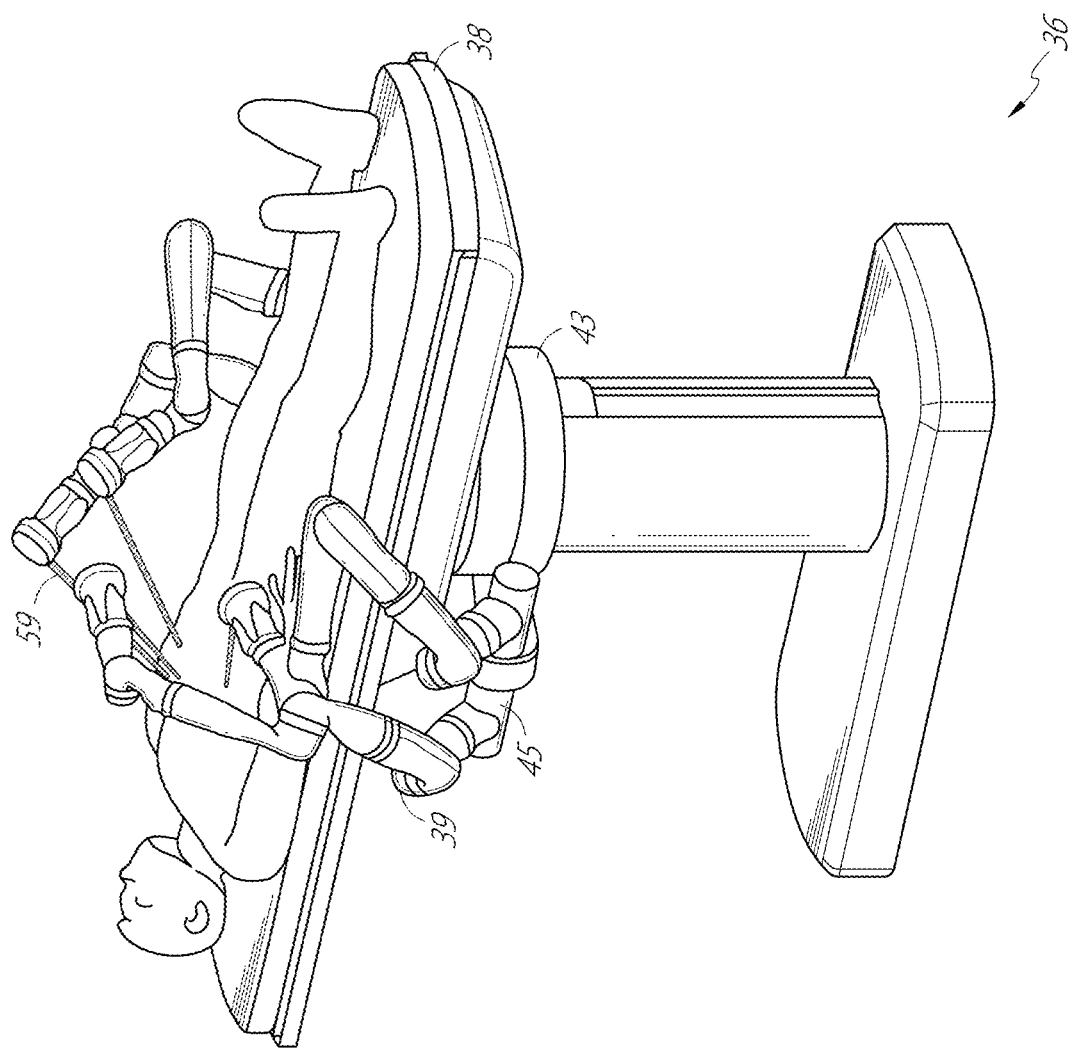
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may be provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a console that provides both a user interface for user input, such as keyboard and/or pendant, as well as a display screen (or touchscreen) for pre-operative and intra-operative information, such as real-time imaging, navigation, and tracking information.

Figure 7:
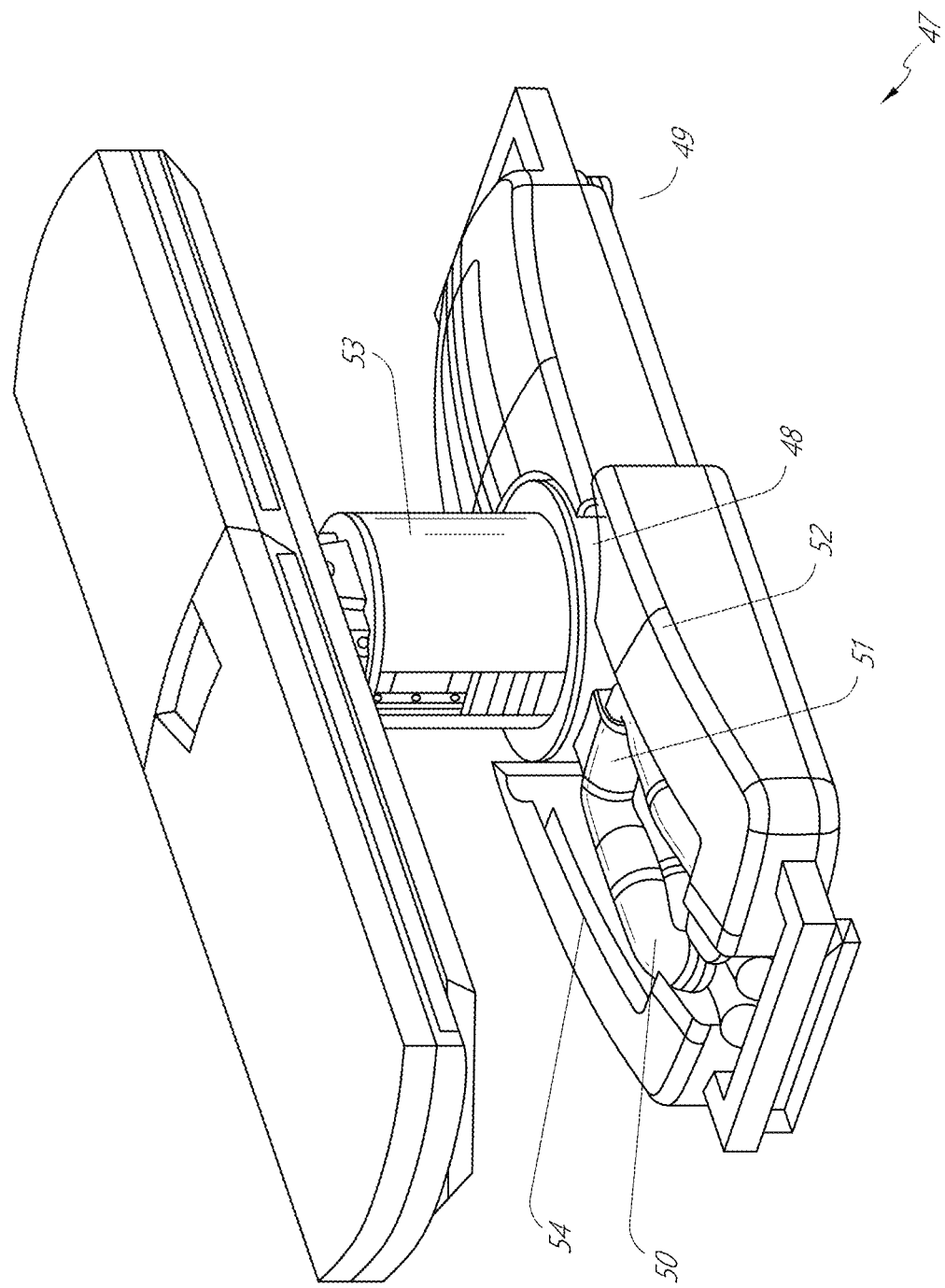
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
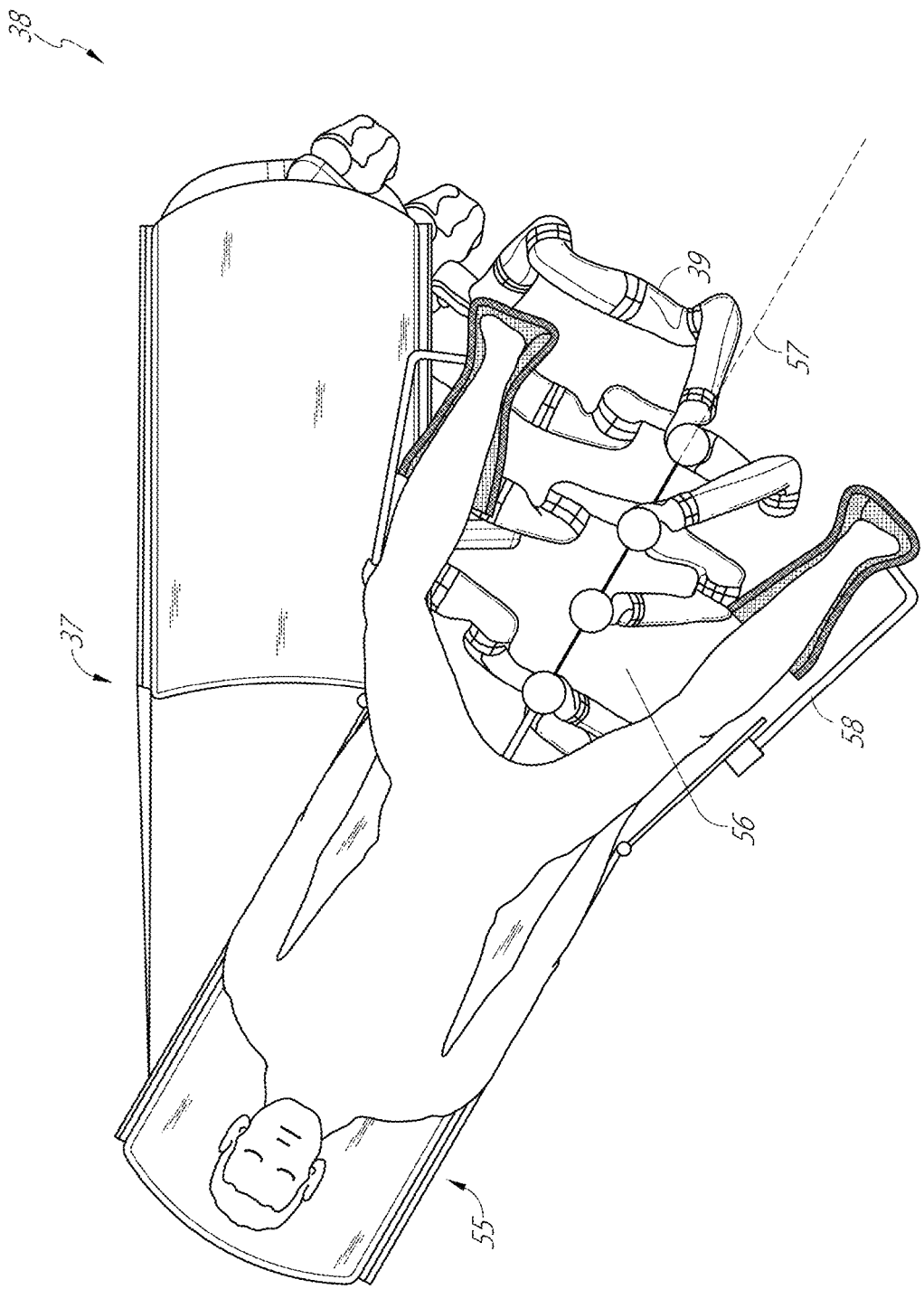
FIG. 8 illustrates an embodiment of a table-based robotic system configured for a ureteroscopy procedure.

FIG. 8 illustrates an embodiment of a robotically-enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments (elongated in shape to accommodate the size of the one or more incisions) may be inserted into the patient's anatomy. After inflation of the patient's abdominal cavity, the instruments, often referred to as laparoscopes, may be directed to perform surgical tasks, such as grasping, cutting, ablating, suturing, etc. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that laparoscopes 59 may be positioned using the arm mounts 45 to be passed through minimal incisions on both sides of the patient to reach his/her abdominal cavity.

Figure 10:
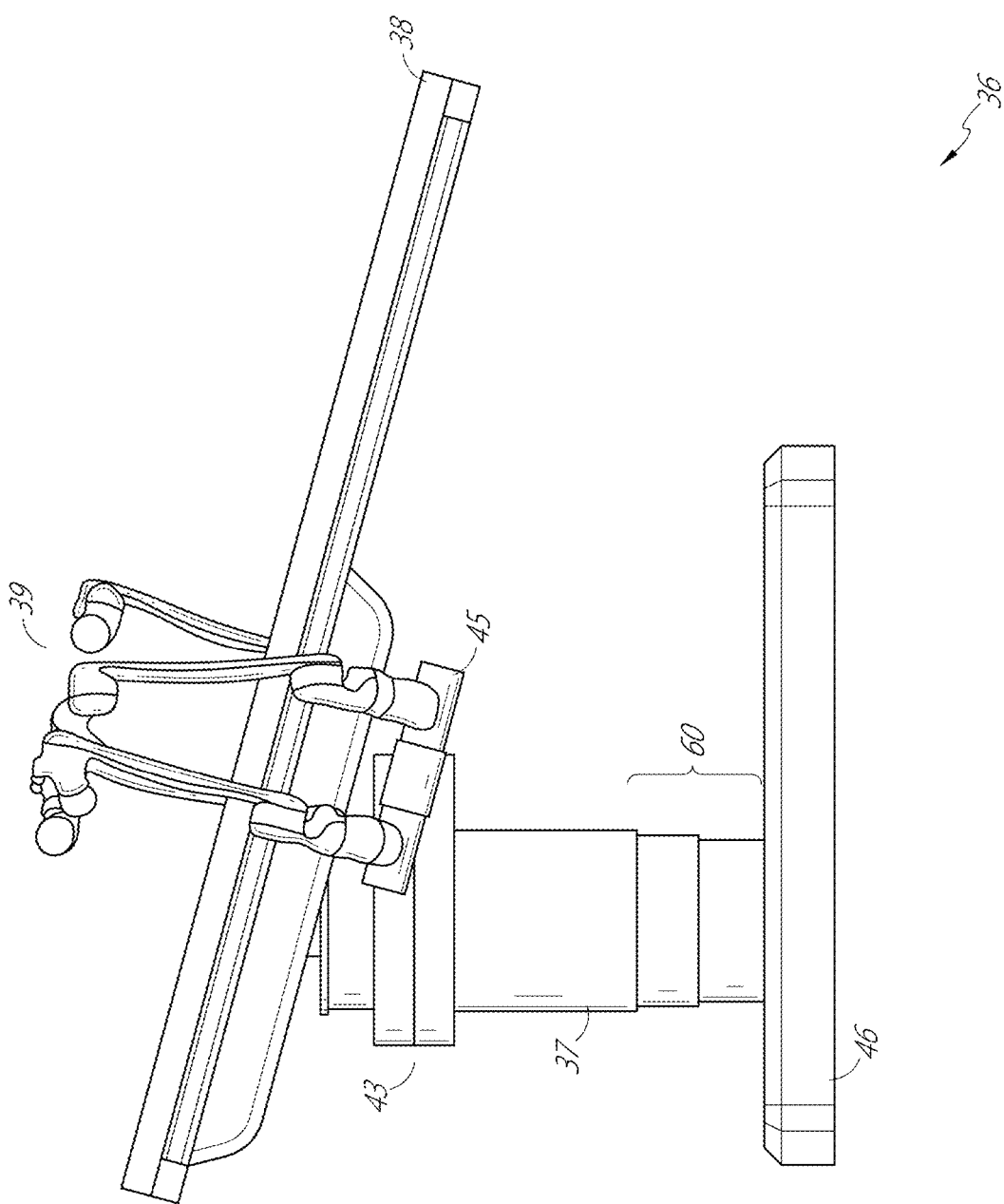
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
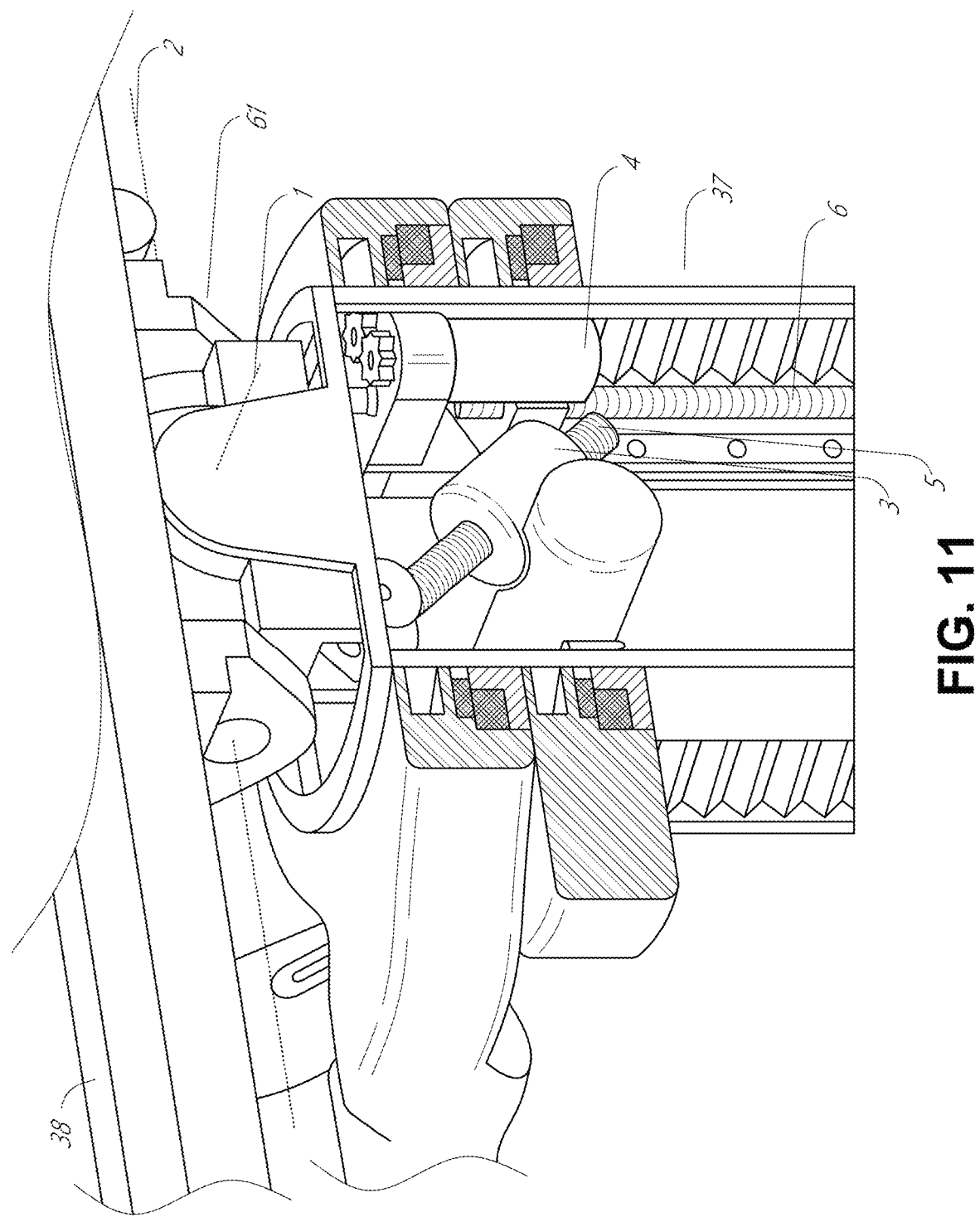
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 2, 4 responsive to an electrical pitch angle command. Rotation along one screw 5 would enable tilt adjustments in one axis 1, while rotation along the other screw 6 would enable tilt adjustments along the other axis 2.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical procedures, such as laparoscopic prostatectomy.

C. Instrument Driver & Interface.

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 12:
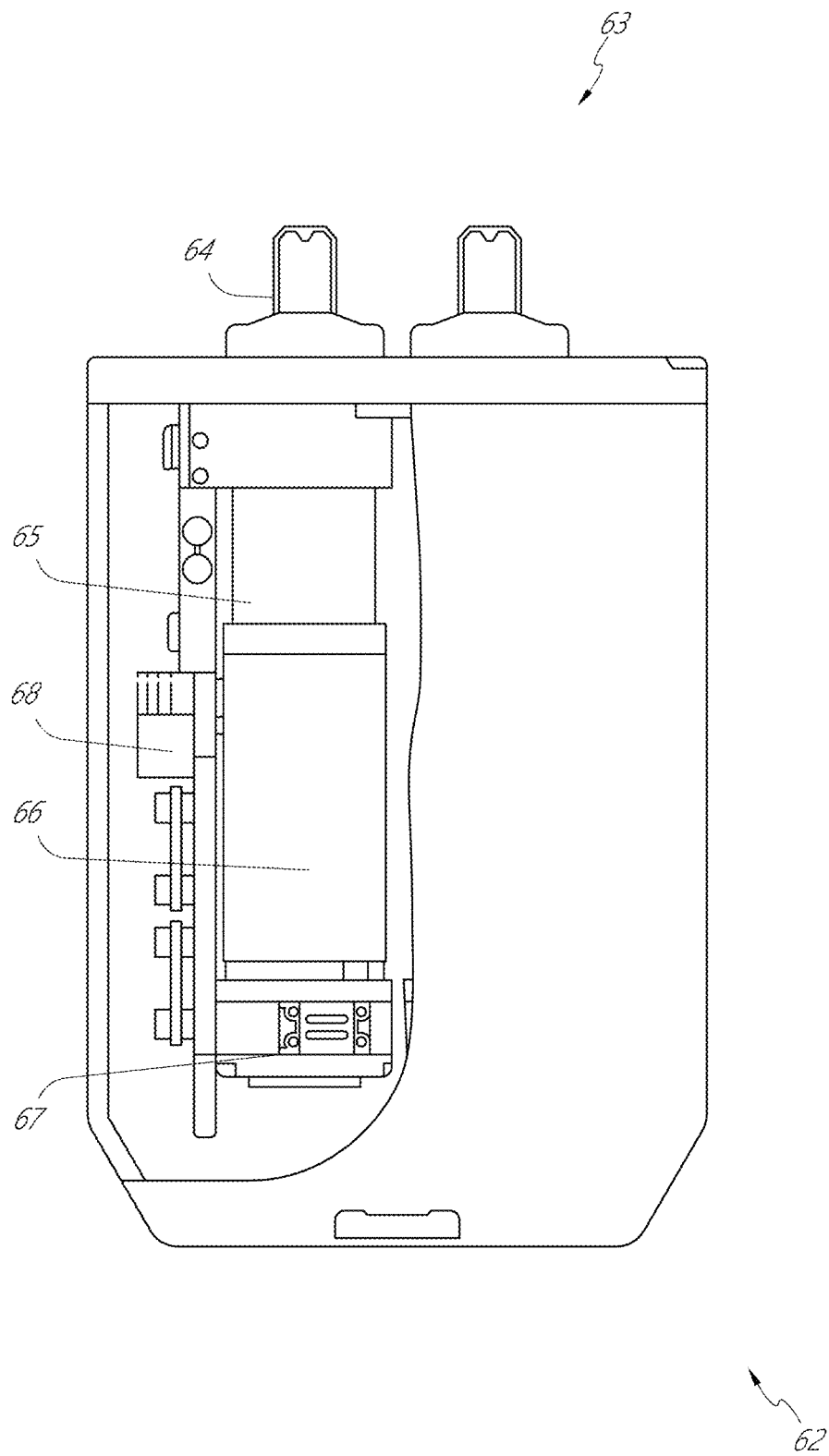
FIG. 12 illustrates an exemplary instrument driver.

FIG. 12 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independent controlled and motorized, the instrument driver 62 may provide multiple (four as shown in FIG. 12) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 13:
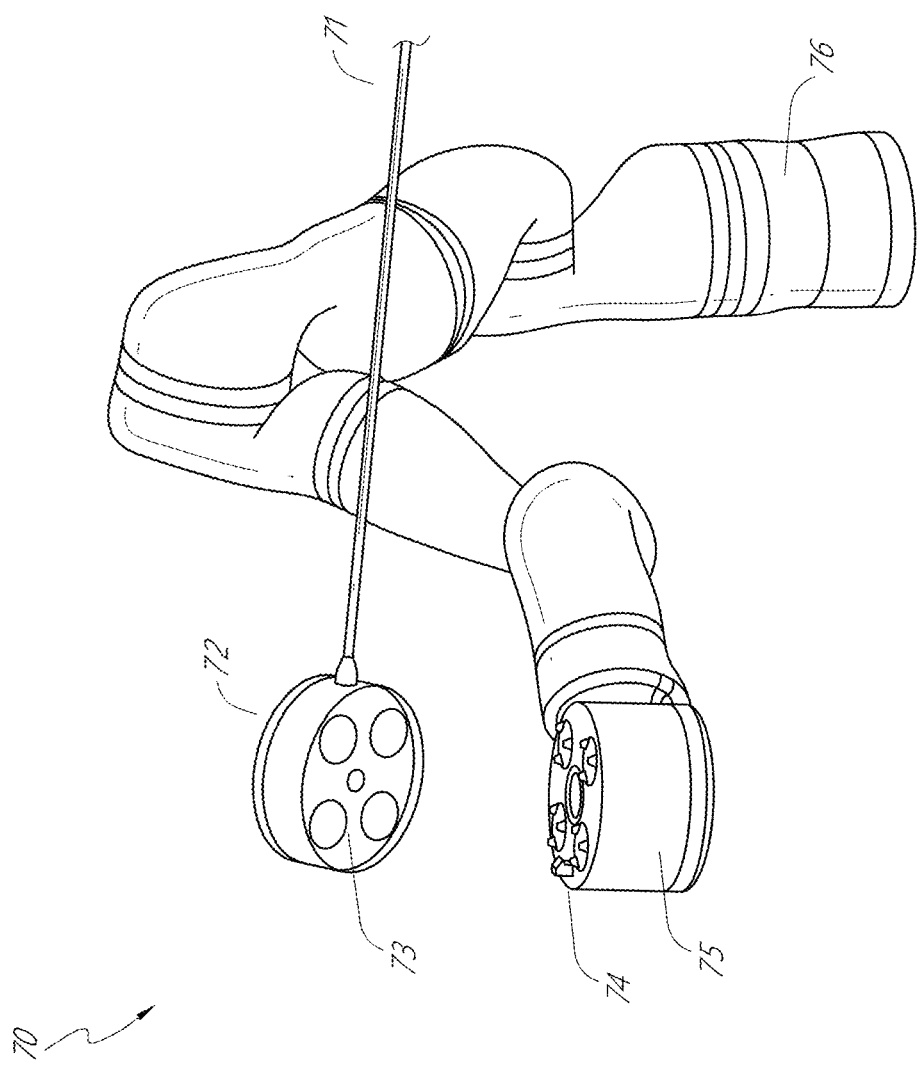
FIG. 13 illustrates an exemplary medical instrument with a paired instrument driver.

FIG. 13 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 66 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector comprising a jointed wrist formed from a clevis with an axis of rotation and a surgical tool, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons within the shaft 71. These individual tendons, such as pull wires, may be individually anchored to individual drive inputs 73 within the instrument handle 72. From the handle 72, the tendons are directed down one or more pull lumens within the elongated shaft 71 and anchored at the distal portion of the elongated shaft 71. In laparoscopy, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In laparoscopy, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools, irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally-located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 13, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongate shaft 71. The resulting entanglement of such tendons may disrupt any control algorithms intended to predict movement of the flexible elongate shaft during an endoscopic procedure.

Figure 14:
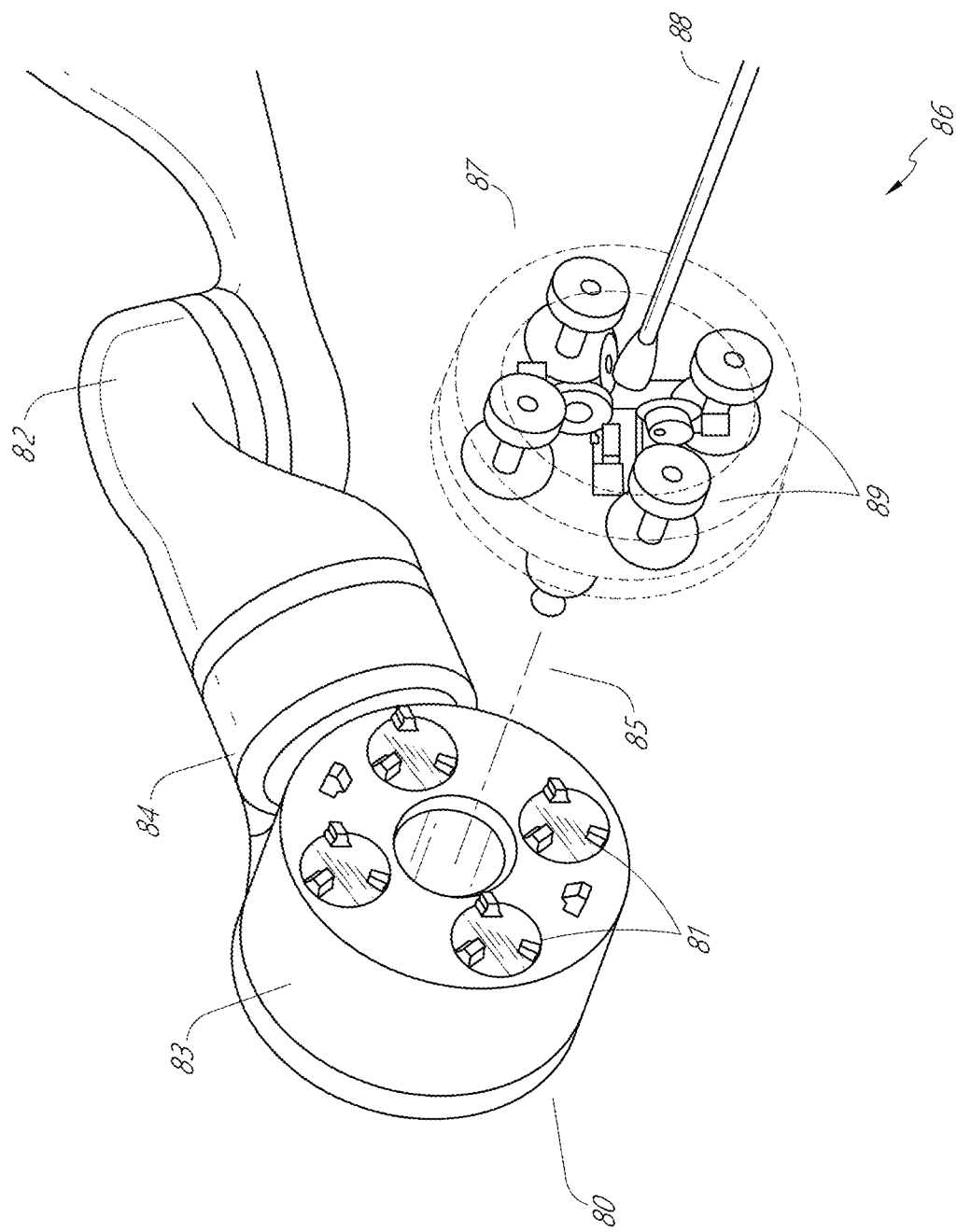
FIG. 14 illustrates an alternative design for an instrument driver and instrument where the axes of the drive units are parallel to the axis of the elongated shaft of the instrument.

FIG. 14 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise of an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 13.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

E. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

FIG. 15 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-10, etc.

As shown in FIG. 15, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans generate two-dimensional images, each representing a "slice" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as preoperative model data 91. The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some feature of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 95. For example, although not shown in FIG. 15, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Introduction to Automatically-Initialized Navigation Systems

Embodiments of the disclosure relate to systems and techniques that facilitate navigation of a medical instrument through luminal networks, for example, lung airways or other anatomical structures having interior open space, by generating and using depth information from endoscope images to determine an initial endoscope position, by analyzing multiple navigation-related data sources to increase accuracy in estimation of location and orientation of a medical instrument within the luminal network, and by generating and using additional depth information to re-initialize the navigation system after an adverse event.

A bronchoscope can include a light source and a small camera that allows a physician to inspect a patient's windpipe and airways. Patient trauma can occur if the precise location of the bronchoscope within the patient airways is not known. To ascertain the location of the bronchoscope, image-based bronchoscopy guidance systems can use data from the bronchoscope camera to perform local registrations (e.g., registrations at a particular location within a luminal network) at bifurcations of patient airways and so beneficially can be less susceptible to position errors due to patient breathing motion. However, as image-based guidance methods rely on the bronchoscope video, they can be affected by artifacts in bronchoscope video caused by patient coughing or mucous obstruction, etc.

Electromagnetic navigation-guided bronchoscopy (EMN bronchoscopy) is a type of bronchoscopic procedure that implements EM technology to localize and guide endoscopic tools or catheters through the bronchial pathways of the lung. EMN bronchoscopy systems can use an EM field generator that emits a low-intensity, varying EM field and establishes the position of the tracking volume around the luminal network of the patient. The EM field is a physical field produced by electrically charged objects that affects the behavior of charged objects in the vicinity of the field. EM sensors attached to objects positioned within the generated field can be used to track locations and orientations of these objects within the EM field. Small currents are induced in the EM sensors by the varying electromagnetic field. The characteristics of these electrical signals are dependent on the distance and angle between a sensor and the EM field generator. Accordingly, an EMN bronchoscopy system can include an EM field generator, a steerable medical instrument having an EM sensor at or near its distal tip, and a guidance computing system. The EM field generator generates an EM field around the luminal network of the patient to be navigated, for example, airways, gastrointestinal tract, or a circulatory pathway. The steerable channel is inserted through the working channel of the bronchoscope and tracked in the EM field via the EM sensor.

Prior to the start of an EMN bronchoscopy procedure, a virtual, three-dimensional (3D) bronchial map can be obtained for the patient's specific airway structure, for example, from a preoperative CT chest scan. Using the map and an EMN bronchoscopy system, physicians can navigate to a desired location within the lung to biopsy lesions, stage lymph nodes, insert markers to guide radiotherapy or guide brachytherapy catheters. For example, a registration can be performed at the beginning of a procedure to generate a mapping between the coordinate system of the EM field and the model coordinate system. Thus, as the steerable channel is tracked during bronchoscopy, the steerable channel's position in the model coordinate system becomes nominally known based on position data from the EM sensor.

As used herein, a coordinate frame is the frame of reference of a particular sensing modality. For example, for EM data the EM coordinate frame is the frame of reference defined by the source of the EM field (e.g., the field generator). For CT images and for a segmented 3D model, this frame of reference is based on the frame defined by the scanner. The present navigation systems address the problem of navigation of representing (register) these different sources of data (which are in their own frames of reference) to the 3D model (i.e. the CT frame), for example, in order to display the location of the instrument inside the model.

Accordingly, as described in more detail below, the disclosed luminal network navigation systems and techniques can combine input from both image-based navigation systems, robotic systems, and EM navigation systems, as well as input from other patient sensors, in order to mitigate navigational problems and enable more effective endoscopy procedures. For example, a navigation fusion system can analyze image information received from an instrument camera, position information from an EM sensor on the instrument tip, and robotic position information from a robotic system guiding movement of the instrument. Based on the analysis, the navigation fusion framework can base instrument position estimates and/or navigation decisions on one or more of these types of navigation data. Some implementations of the navigation fusion framework can further determine instrument position relative to a 3D model of the luminal network. In some embodiments, the initial instrument position used to initialize tracking via the navigation fusion system can be generated based on depth information as described herein.

The disclosed systems and techniques can provide advantages for bronchoscopy guidance systems and other applications, including other types of endoscopic procedures for navigation of luminal networks. In anatomy, a "lumen" may refer to the inner open space or cavity of an organ, as of an airway, a blood vessel, a kidney, a heart, an intestine, or any other suitable organ in which a medical procedure is being performed. As used herein, a "luminal network" refers to an anatomical structure having at least one lumen leading towards a target tissue site, for example, the airways of the lungs, the circulatory system, calyx, and the gastrointestinal system. Thus, although the present disclosure provides examples of navigation systems relating to bronchoscopy, it will be appreciated that the disclosed position estimation aspects are applicable to other medical systems for navigation of a luminal network of a patient. As such, the disclosed systems and techniques can be used with bronchoscopes, ureteroscopes, gastrointestinal endoscopes, and other suitable medical instruments.

3. Overview of Example Navigation Systems

Figure 16A:
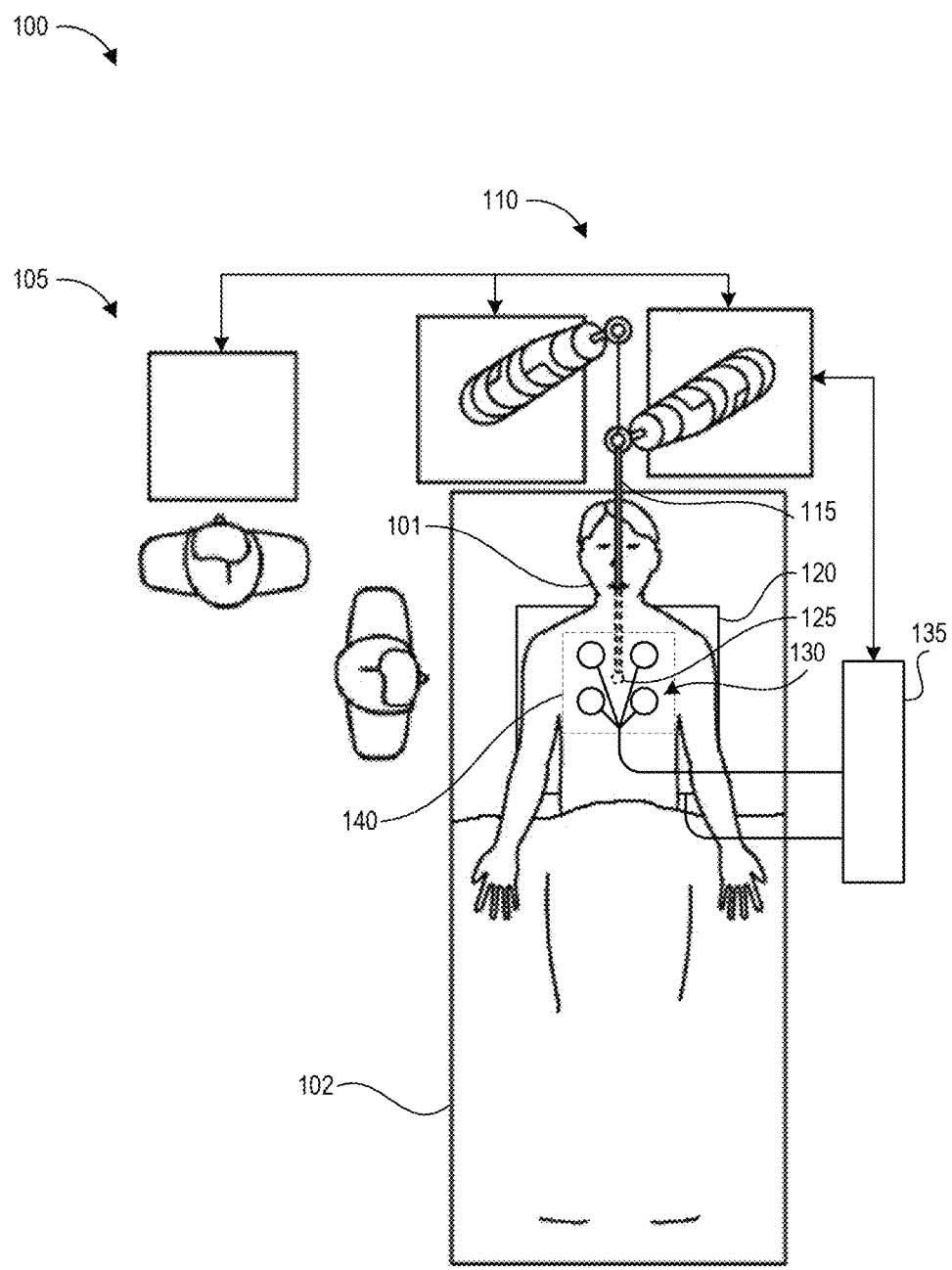
FIG. 16A illustrates an example operating environment implementing the disclosed navigation systems and techniques.

FIG. 16A illustrates an example operating environment 100 implementing one or more aspects of the disclosed navigation systems and techniques. The operating environment 100 includes patient 101, a platform 102 supporting the patient 101, a medical robotic system 110 guiding movement of endoscope 115, command center 105 for controlling operations of the medical robotic system 110, EM controller 135, EM field generator 120, and EM sensors 125, 130. FIG. 16A also illustrates an outline of a region of a luminal network 140 within the patient 101, shown in more detail in FIG. 16B.

The medical robotic system 110 can include one or more robotic arms for positioning and guiding movement of endoscope 115 through the luminal network 140 of the patient 101. Command center 105 can be communicatively coupled to the medical robotic system 110 for receiving position data and/or providing control signals from a user. As used herein, "communicatively coupled" refers to any wired and/or wireless data transfer mediums, including but not limited to a wireless wide area network (WWAN) (e.g., one or more cellular networks), a wireless local area network (WLAN) (e.g., configured for one or more standards, such as the IEEE 802.11 (Wi-Fi)), Bluetooth, data transfer cables, and/or the like. The medical robotic system 110 can be any of the systems described above with respect to FIGS. 1-15. An embodiment of the medical robotic system 110 is discussed in more detail with respect to FIG. 16C, and the command center 105 is discussed in more detail with respect to FIG. 17.

The endoscope 115 may be a tubular and flexible surgical instrument that is inserted into the anatomy of a patient to capture images of the anatomy (e.g., body tissue) and provide a working channel for insertion of other medical instruments to a target tissue site. As described above, the endoscope 115 can be a procedure-specific endo scope, for example a bronchoscope, gastroscope, or ureteroscope, or may be a laparoscope or vascular steerable catheter. The endoscope 115 can include one or more imaging devices (e.g., cameras or other types of optical sensors) at its distal end. The imaging devices may include one or more optical components such as an optical fiber, fiber array, photosensitive substrate, and/or lens(es). The optical components move along with the tip of the endoscope 115 such that movement of the tip of the endoscope 115 results in corresponding changes to the field of view of the images captured by the imaging devices. The distal end of the endoscope 115 can be provided with one or more EM sensors 125 for tracking the position of the distal end within an EM field generated around the luminal network 140. The distal end of the endo scope 115 is further described with reference to FIG. 18 below.

EM controller 135 can control EM field generator 120 to produce a varying EM field. The EM field can be time-varying and/or spatially varying, depending upon the embodiment. The EM field generator 120 can be an EM field generating board in some embodiments. Some embodiments of the disclosed patient navigation systems can use an EM field generator board positioned between the patient and the platform 102 supporting the patient, and the EM field generator board can incorporate a thin barrier that minimizes any tracking distortions caused by conductive or magnetic materials located below it. In other embodiments, an EM field generator board can be mounted on a robotic arm, for example, similar to those shown in medical robotic system 110, which can offer flexible setup options around the patient.

An EM spatial measurement system incorporated into the command center 105, medical robotic system 110, and/or EM controller 135 can determine the location of objects within the EM field that are embedded or provided with EM sensor coils, for example, EM sensors 125, 130. When an EM sensor is placed inside a controlled, varying EM field as described herein, voltages are induced in the sensor coils. These induced voltages can be used by the EM spatial measurement system to calculate the position and orientation of the EM sensor and thus the object having the EM sensor. As the magnetic fields are of a low field strength and can safely pass through human tissue, location measurement of an object is possible without the line-of-sight constraints of an optical spatial measurement system.

EM sensor 125 can be coupled to a distal end of the endoscope 115 in order to track its location within the EM field. The EM field is stationary relative to the EM field generator, and a coordinate frame of a 3D model of the luminal network can be mapped to a coordinate frame of the EM field. A number of additional EM sensors 130 can be provided on the body surface of the patient (e.g., in the region of the luminal network 140) in order to aid in tracking the location of the EM sensor 125, for example, by enabling compensation for patient movement including displacement caused by respiration. A number of different EM sensors 130 can be spaced apart on the body surface.

Figure 16B:
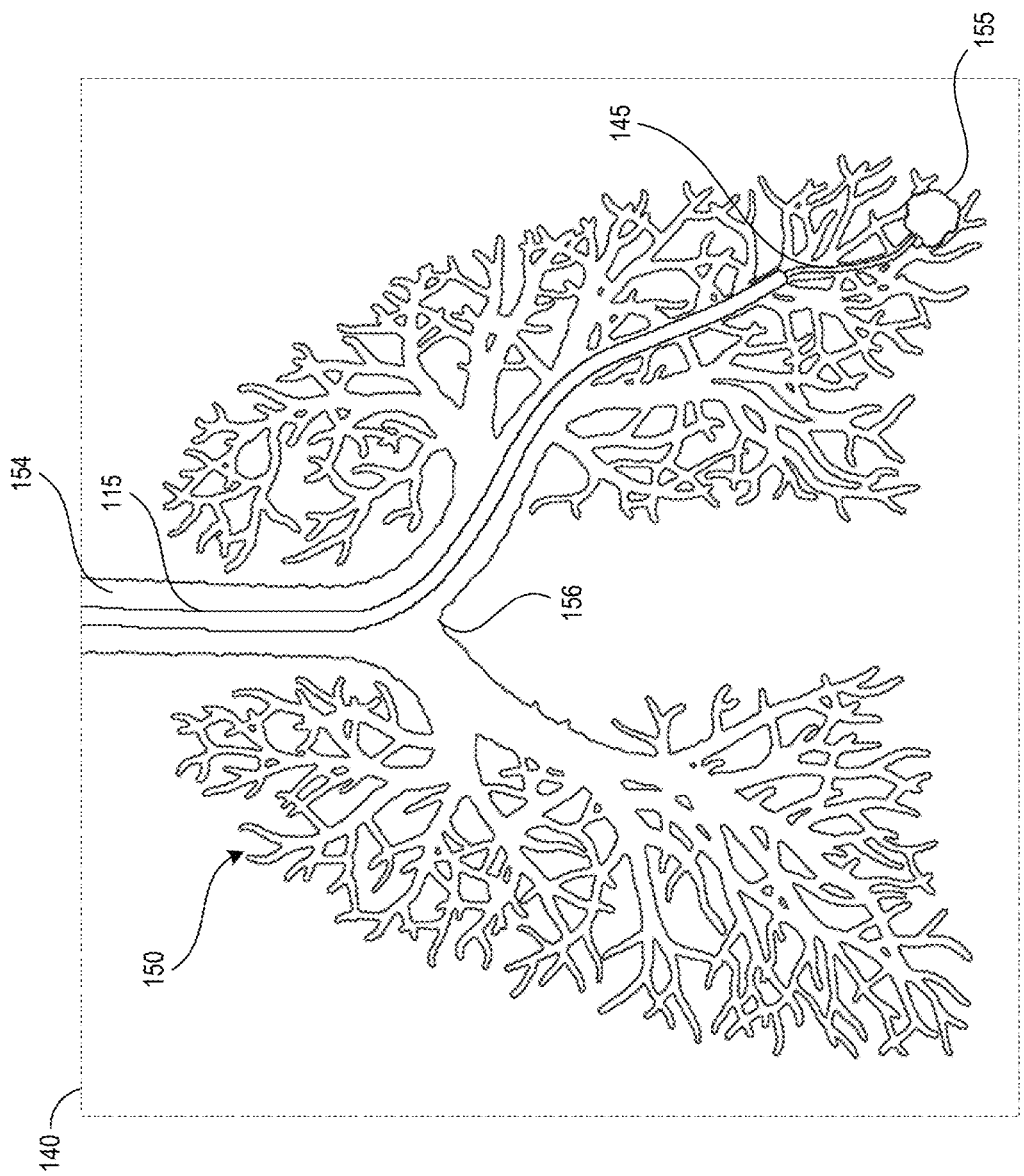
FIG. 16B illustrates an example luminal network navigated in the environment of FIG. 16A.

FIG. 16B illustrates an example luminal network 140 that can be navigated in the operating environment 100 of FIG. 16A. The luminal network 140 includes the branched structure of the airways 150 of the patient, the trachea 154 leading to the main carina 156 (the first bifurcation encountered during bronchoscopy navigation), and a nodule (or lesion) 155 that can be accessed as described herein for diagnosis and/or treatment. As illustrated, the nodule 155 is located at the periphery of the airways 150. The endoscope 115 has a first diameter and thus its distal end is not able to be positioned through the smaller-diameter airways around the nodule 155. Accordingly, a steerable catheter 155 extends from the working channel of the endoscope 115 the remaining distance to the nodule 155. The steerable catheter 145 may have a lumen through which instruments, for example, biopsy needles, cytology brushes, and/or tissue sampling forceps, can be passed to the target tissue site of nodule 155. In such implementations, both the distal end of the endoscope 115 and the distal end of the steerable catheter 145 can be provided with EM sensors for tracking their position within the airways 150. In other embodiments, the overall diameter of the endoscope 115 may be small enough to reach the periphery without the steerable catheter 155, or may be small enough to get close to the periphery (e.g., within 2.5-3 cm) to deploy medical instruments through a non-steerable catheter. The medical instruments deployed through the endoscope 115 may be equipped with EM sensors, and the position estimation techniques described below can be applied to such medical instruments when they are deployed beyond the distal tip of the endoscope 115.

In some embodiments, a 2D display of a 3D luminal network model as described herein, or a cross-section of a 3D model, can resemble FIG. 16B. Estimated position information can be overlaid onto such a representation.

Figure 16C:
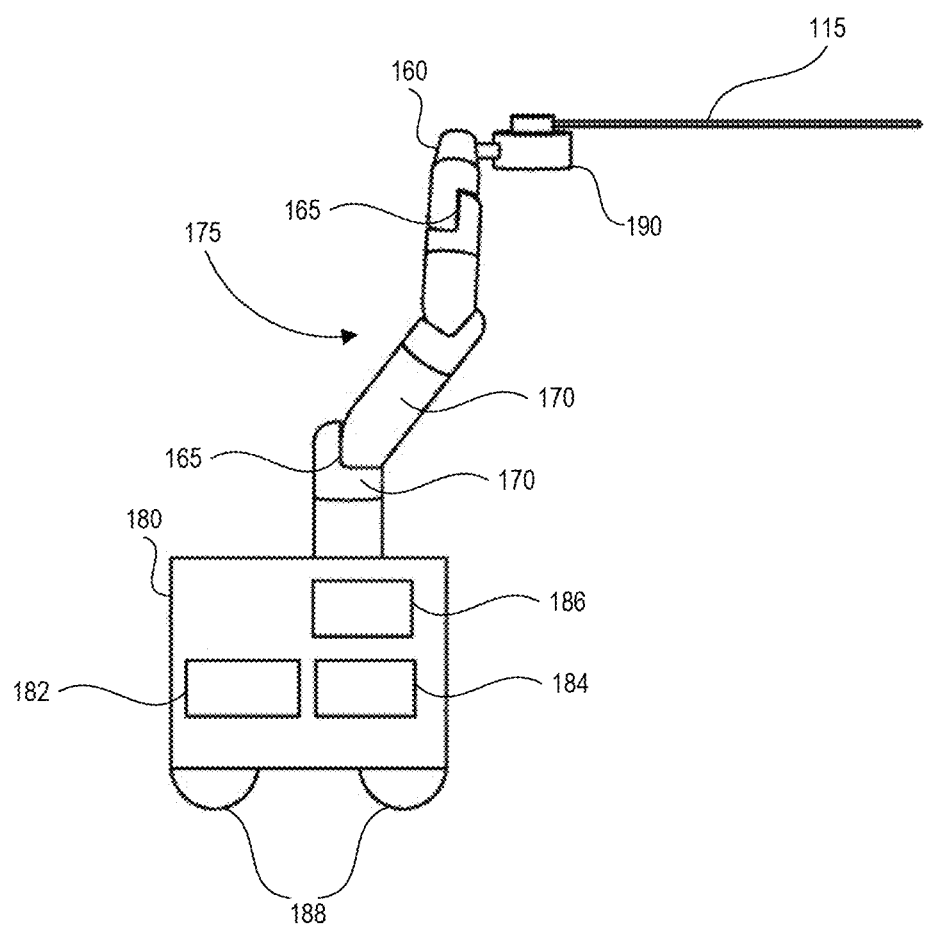
FIG. 16C illustrates an example robotic arm for guiding instrument movement in through the luminal network of FIG. 16B.

FIG. 16C illustrates an example robotic arm 175 of a medical robotic system 110 for guiding instrument movement in through the luminal network 140 of FIG. 16B. The robotic arm 175 can be robotic arms 12, 39 described above in some embodiments, and is coupled to base 180, which can be cart base 15, column 37 of patient platform 38, or a ceiling-based mount in various embodiments. As described above, the robotic arm 175 includes multiple arm segments 170 coupled at joints 165, which provides the robotic arm 175 multiple degrees of freedom.

The robotic arm 175 may be coupled to an instrument driver 190, for example instrument driver 62 described above, using a mechanism changer interface (MCI) 160. The instrument driver 190 can be removed and replaced with a different type of instrument driver, for example, a first type of instrument driver configured to manipulate an endoscope or a second type of instrument driver configured to manipulate a laparoscope. The MCI 160 includes connectors to transfer pneumatic pressure, electrical power, electrical signals, and optical signals from the robotic arm 175 to the instrument driver 190. The MCI 160 can be a set screw or base plate connector. The instrument driver 190 manipulates surgical instruments, for example, the endoscope 115 using techniques including direct drive, harmonic drive, geared drives, belts and pulleys, magnetic drives, and the like. The MCI 160 is interchangeable based on the type of instrument driver 190 and can be customized for a certain type of surgical procedure. The robotic 175 arm can include a joint level torque sensing and a wrist at a distal end.

Robotic arm 175 of the medical robotic system 110 can manipulate the endoscope 115 using tendons as described above to deflect the tip of the endoscope 115. The endoscope 115 may exhibit nonlinear behavior in response to forces applied by the elongate movement members. The nonlinear behavior may be based on stiffness and compressibility of the endoscope 115, as well as variability in slack or stiffness between different elongate movement members.

The base 180 can be positioned such that the robotic arm 175 has access to perform or assist with a surgical procedure on a patient, while a user such as a physician may control the medical robotic system 110 from the comfort of the command console. The base 180 can be communicatively coupled to the command console 105 shown in FIG. 16A.

The base 180 can include a source of power 182, pneumatic pressure 186, and control and sensor electronics 184—including components such as a central processing unit, data bus, control circuitry, and memory—and related actuators such as motors to move the robotic arm 175. The electronics 184 can implement the navigation control techniques described herein. The electronics 184 in the base 180 may also process and transmit control signals communicated from the command console. In some embodiments, the base 180 includes wheels 188 to transport the medical robotic system 110 and wheel locks/brakes (not shown) for the wheels 188. Mobility of the medical robotic system 110 helps accommodate space constraints in a surgical operating room as well as facilitate appropriate positioning and movement of surgical equipment. Further, the mobility allows the robotic arm 175 to be configured such that the robotic arm 175 does not interfere with the patient, physician, anesthesiologist, or any other equipment. During procedures, a user may control the robotic arm 175 using control devices, for example, the command console.

Figure 17:
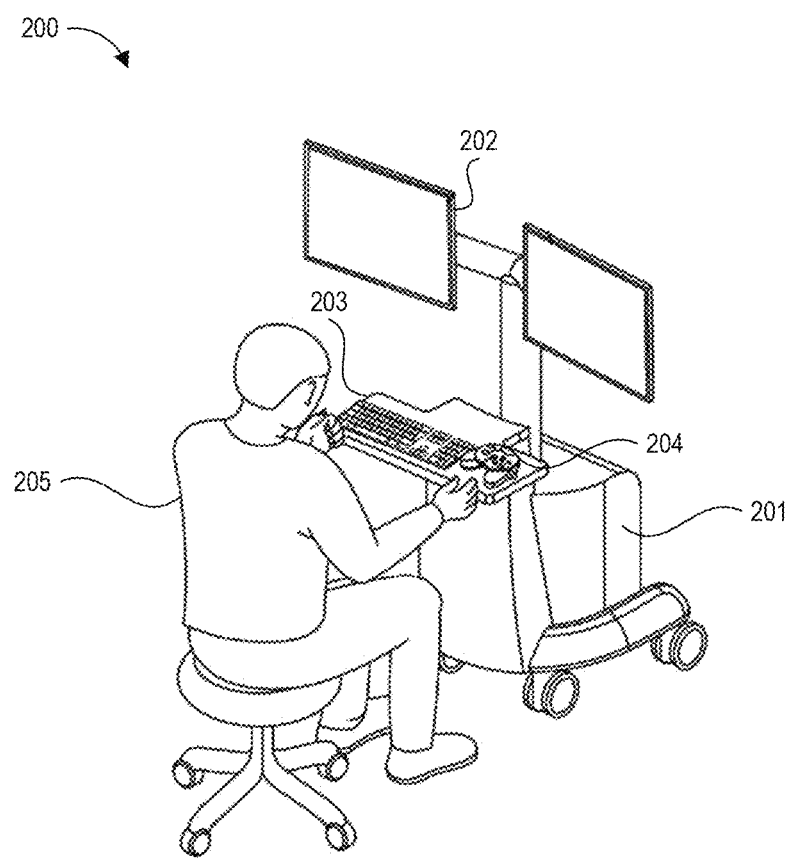
FIG. 17 illustrates an example command console for the example medical robotic system, according to one embodiment.

FIG. 17 illustrates an example command console 200 that can be used, for example, as the command console 105 in the example operating environment 100. The command console 200 includes a console base 201, display modules 202, e.g., monitors, and control modules, e.g., a keyboard 203 and joystick 204. In some embodiments, one or more of the command console 200 functionality may be integrated into a base 180 of the medical robotic system 110 or another system communicatively coupled to the medical robotic system 110. A user 205, e.g., a physician, remotely controls the medical robotic system 110 from an ergonomic position using the command console 200.

The console base 201 may include a central processing unit, a memory unit, a data bus, and associated data communication ports that are responsible for interpreting and processing signals such as camera imagery and tracking sensor data, e.g., from the endoscope 115 shown in FIGS. 16A-16C. In some embodiments, both the console base 201 and the base 180 perform signal processing for load-balancing. The console base 201 may also process commands and instructions provided by the user 205 through the control modules 203 and 204. In addition to the keyboard 203 and joystick 204 shown in FIG. 17, the control modules may include other devices, for example, computer mice, trackpads, trackballs, control pads, controllers such as handheld remote controllers, and sensors (e.g., motion sensors or cameras) that capture hand gestures and finger gestures. A controller can include a set of user inputs (e.g., buttons, joysticks, directional pads, etc.) mapped to an operation of the instrument (e.g., articulation, driving, water irrigation, etc.).

The user 205 can control a surgical instrument such as the endoscope 115 using the command console 200 in a velocity mode or position control mode. In velocity mode, the user 205 directly controls pitch and yaw motion of a distal end of the endoscope 115 based on direct manual control using the control modules. For example, movement on the joystick 204 may be mapped to yaw and pitch movement in the distal end of the endoscope 115. The joystick 204 can provide haptic feedback to the user 205. For example, the joystick 204 may vibrate to indicate that the endoscope 115 cannot further translate or rotate in a certain direction. The command console 200 can also provide visual feedback (e.g., pop-up messages) and/or audio feedback (e.g., beeping) to indicate that the endoscope 115 has reached maximum translation or rotation.

In position control mode, the command console 200 uses a 3D map of a patient luminal network and input from navigational sensors as described herein to control a surgical instrument, e.g., the endoscope 115. The command console 200 provides control signals to robotic arms 175 of the medical robotic system 110 to manipulate the endoscope 115 to a target location. Due to the reliance on the 3D map, position control mode may require accurate mapping of the anatomy of the patient.

In some embodiments, users 205 can manually manipulate robotic arms 175 of the medical robotic system 110 without using the command console 200. During setup in a surgical operating room, the users 205 may move the robotic arms 175, endoscope 115 (or endoscopes), and other surgical equipment to access a patient. The medical robotic system 110 may rely on force feedback and inertia control from the users 205 to determine appropriate configuration of the robotic arms 175 and equipment.

The displays 202 may include electronic monitors (e.g., LCD displays, LED displays, touch-sensitive displays), virtual reality viewing devices, e.g., goggles or glasses, and/or other display devices. In some embodiments, the display modules 202 are integrated with the control modules, for example, as a tablet device with a touchscreen. In some embodiments, one of the displays 202 can display a 3D model of the patient's luminal network and virtual navigation information (e.g., a virtual representation of the end of the endoscope within the model based on EM sensor position) while the other of the displays 202 can display image information received from the camera or another sensing device at the end of the endoscope 115. In some implementations, the user 205 can both view data and input commands to the medical robotic system 110 using the integrated displays 202 and control modules. The displays 202 can display 2D renderings of 3D images and/or 3D images using a stereoscopic device, e.g., a visor or goggles. The 3D images provide an "endo view" (i.e., endoscopic view), which is a computer 3D model illustrating the anatomy of a patient. The "endo view" provides a virtual environment of the patient's interior and an expected location of an endoscope 115 inside the patient. A user 205 compares the "endo view" model to actual images captured by a camera to help mentally orient and confirm that the endoscope 115 is in the correct—or approximately correct—location within the patient. The "endo view" provides information about anatomical structures, e.g., the shape of airways, circulatory vessels, or an intestine or colon of the patient, around the distal end of the endoscope 115. The display modules 202 can simultaneously display the 3D model and CT scans of the anatomy the around distal end of the endoscope 115. Further, the display modules 202 may overlay the already determined navigation paths of the endoscope 115 on the 3D model and CT scans.

In some embodiments, a model of the endoscope 115 is displayed with the 3D models to help indicate a status of a surgical procedure. For example, the CT scans identify a lesion in the anatomy where a biopsy may be necessary. During operation, the display modules 202 may show a reference image captured by the endoscope 115 corresponding to the current location of the endoscope 115. The display modules 202 may automatically display different views of the model of the endoscope 115 depending on user settings and a particular surgical procedure. For example, the display modules 202 show an overhead fluoroscopic view of the endoscope 115 during a navigation step as the endoscope 115 approaches an operative region of a patient.

Figure 18:
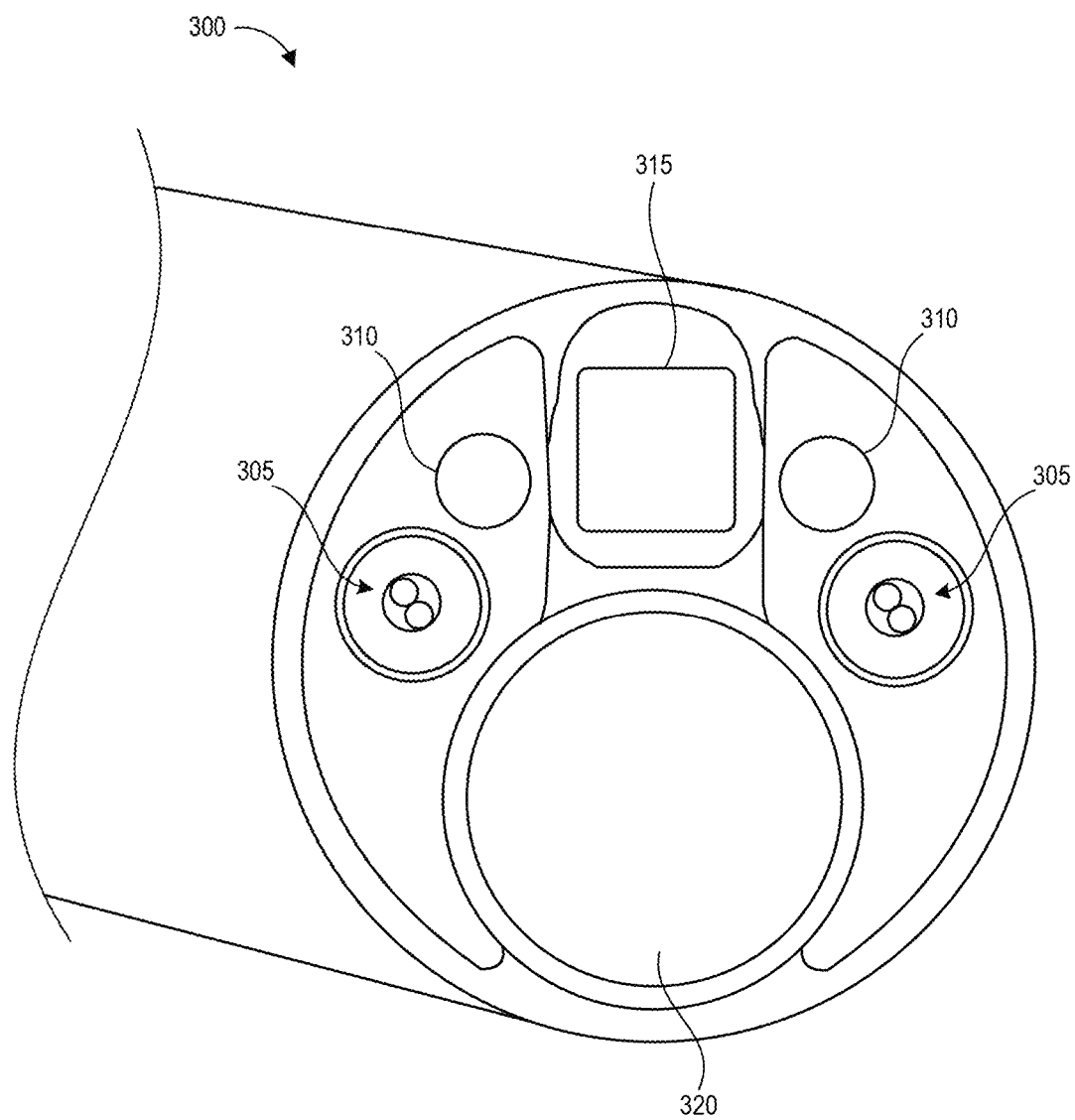
FIG. 18 illustrates an example endoscope having imaging and EM sensing capabilities as described herein.

FIG. 18 illustrates the distal end 300 of an example endoscope having imaging and EM sensing capabilities as described herein, for example, the endoscope 115 of FIGS. 16A-16C. In FIG. 18, the distal end 300 of the endoscope includes an imaging device 315, illumination sources 310, and ends of EM sensor coils 305. The distal end 300 further includes an opening to a working channel 320 of the endoscope through which surgical instruments, such as biopsy needles, cytology brushes, and forceps, may be inserted along the endoscope shaft, allowing access to the area near the endoscope tip.

The illumination sources 310 provide light to illuminate a portion of an anatomical space. The illumination sources can each be one or more light-emitting devices configured to emit light at a selected wavelength or range of wavelengths. The wavelengths can be any suitable wavelength, for example, visible spectrum light, infrared light, x-ray (e.g., for fluoroscopy), to name a few examples. In some embodiments, illumination sources 310 can include light-emitting diodes (LEDs) located at the distal end 300. In some embodiments, illumination sources 310 can include one or more fiber optic fibers extending through a length of the endoscope to transmit light through the distal end 300 from a remote light source, for example, an x-ray generator. Where the distal end 300 includes multiple illumination sources 310 these can each be configured to emit the same or different wavelengths of light as one another.

The imaging device 315 can include any photosensitive substrate or structure configured to convert energy representing received light into electric signals, for example, a charge-coupled device (CCD) or complementary metal-oxide semiconductor (CMOS) image sensor. Some examples of imaging device 315 can include one or more optical fibers, for example, a fiber optic bundle, configured to transmit light representing an image from the distal end 300 of the endoscope to an eyepiece and/or image sensor near the proximal end of the endoscope. Imaging device 315 can additionally include one or more lenses and/or wavelength pass or cutoff filters as required for various optical designs. The light emitted from the illumination sources 310 allows the imaging device 315 to capture images of the interior of a patient's luminal network. These images can then be transmitted as individual frames or series of successive frames (e.g., a video) to a computer system such as command console 200 for processing as described herein.

Electromagnetic coils 305 located on the distal end 300 may be used with an electromagnetic tracking system to detect the position and orientation of the distal end 300 of the endoscope while it is disposed within an anatomical system. In some embodiments, the coils 305 may be angled to provide sensitivity to electromagnetic fields along different axes, giving the disclosed navigational systems the ability to measure a full 6 degrees of freedom: three positional and three angular. In other embodiments, only a single coil may be disposed on or within the distal end 300 with its axis oriented along the endoscope shaft of the endoscope. Due to the rotational symmetry of such a system, it is insensitive to roll about its axis, so only 5 degrees of freedom may be detected in such an implementation.

Figure 19:
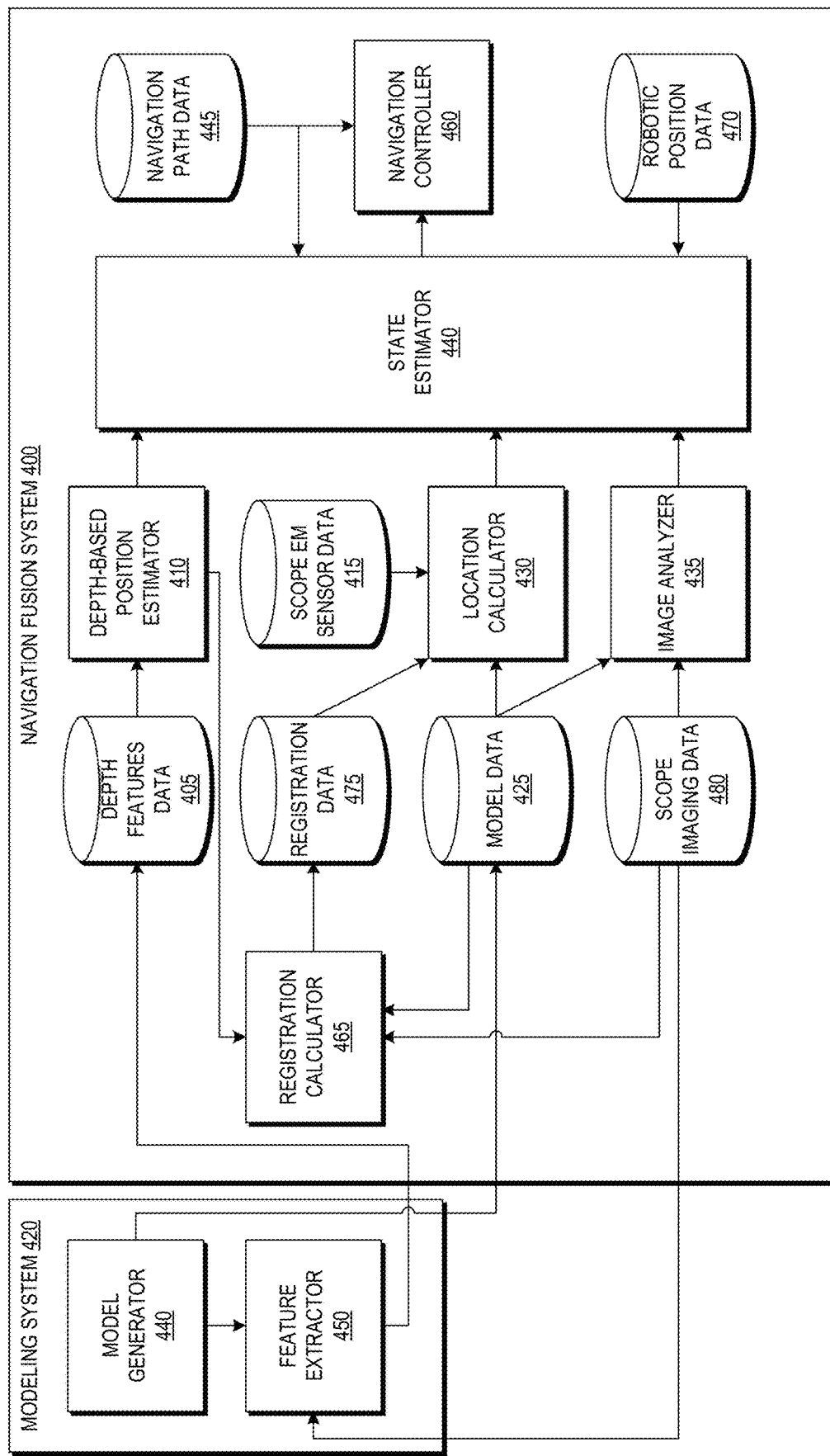
FIG. 19 depicts a schematic block diagram of a navigation system as described herein.

FIG. 19 illustrates a schematic block diagram of an example navigation fusion system 400 as described herein. As described in more detail below, using the system 400, data from a number of different sources is combined and repeatedly analyzed during a surgical procedure to provide an estimation of the real-time movement information and location/orientation information of a surgical instrument (e.g., the endoscope) within the luminal network of the patient and to make navigation decisions.

The navigation fusion system 400 includes a number of data repositories including depth features data repository 405, endoscope EM sensor data repository 415, registration data repository 475, model data repository 425, endoscope imaging data repository 480, navigation path data repository 445, and robotic position data repository 470. Though shown separately in FIG. 19 for purposes of clarity in the discussion below, it will be appreciated that some or all of the data repositories can be stored together in a single memory or set of memories. The system 400 also includes a number of processing modules including a registration calculator 465, depth-based position estimator 410, location calculator 430, image analyzer 435, state estimator 440, and navigation controller 460. Each module can represent a set of computer-readable instructions, stored in a memory, and one or more processors configured by the instructions for performing the features described below together. The navigation fusion system 400 can be implemented as one or more data storage devices and one or more hardware processors, for example, in the control and sensor electronics 184 and/or console base 201 described above. The navigation fusion system 400 can be an embodiment of the localization system 90 in some implementations.

FIG. 19 also illustrates modeling system 420 in communication with the navigation fusion system 400. As described in more detail below, using the modeling system 420, data representing a number of images of a patient's anatomical luminal network can be analyzed to build a three-dimensional model of a virtual representation of the anatomical luminal network, and this virtual anatomical luminal network can be used to build the depth features data repository 405. Though illustrated separately, in some embodiments the modeling system 420 and navigation fusion system 400 can be combined into a single system. The modeling system 420 includes a number of processing modules including model generator 440 and feature extractor 450. Although the model data repository 425 and depth features data repository 405 are illustrated within the navigation fusion system 400, these data repositories can in some implementations be located alternatively or additionally within the modeling system 420.

The model generator 440 is a module configured to receive data from a medical imaging system (not illustrated), for example, a CT imaging system or magnetic resonance imaging system. The received data can include a series of two-dimensional images representing the anatomical luminal network of the patient. The model generator 440 can generate a three-dimensional volume of data from the series of two-dimensional images, and can form the virtual three-dimensional model of the internal surfaces of the anatomical luminal network from the three-dimensional volume of data. For example, the model generator can apply segmentation to identify portions of the data corresponding to the tissue of the anatomical luminal network. As such, the resulting model can represent the interior surfaces of the tissue of the anatomical luminal network.

The model data repository 425 is a data storage device that stores data representing a model of the luminal network of the patient, for example, the model generated by the model generator 440. Such a model can provide 3D information about the structure and connectivity of the luminal network, including the topography and/or diameters of patient airways in some examples. Some CT scans of patient lungs are performed at breath-hold so that the patient's airways are expanded to their full diameter in the model.

The endoscope imaging data repository 480 is a data storage device that stores image data received from a camera at a distal end of an endoscope, for example, the imaging device 315. The image data can be discrete images or series of image frames in a video sequence in various embodiments.

The feature extractor 450 is a module configured to receive the model from the model generator 440 and build a database of depth features corresponding to a number of different location within the model. For example, the feature extractor 450 can identify a number of different locations within the model, computationally position a virtual imaging device at each of the locations, generate a virtual image at each location, and then derive specified features from the virtual image. A "virtual imaging device" as described herein is not a physical imaging device, but rather a computational simulation of an image capture device. The simulation can generate virtual images based on virtual imaging device parameters including field of view, lens distortion, focal length, and brightness shading, which can in turn be based on parameters of an actual imaging device.

Each generated virtual image can correspond to a virtual depth map representing the distance between the location of the virtual imaging device and tissue of the virtual luminal network within the virtual field of view of the virtual imaging device. The feature extractor 450 can match the virtual imaging device parameters to the parameters of an actual imaging device that has been identified for use in a medical procedure involving the patient's luminal network. An example process for building the database is described in more detail below with respect to FIG. 20.

The feature extractor 450 can also receive data from the endoscope imaging data repository 480, generate a depth map representing the distance between the endoscope imaging device and the imaged tissue represented by pixels of the image, and derive features from the generated depth map. In some embodiments, the feature extractor 450 can use photoclinometry (e.g., shape by shading) processing to generate a depth map based on a single image. In some embodiments, the feature extractor 450 can use a stereoscopic image set depicting the imaged region to generate a depth map.

Depth features data repository 405 is a data storage device that stores a database of features derived from depth maps and/or virtual depth maps, as generated by the feature extractor 450. The features can vary based on the nature of the luminal network and/or the use of the features during the navigation procedure. The features can include, for example, positions of local maxima within the depth map (e.g., representing the farthest virtual tissue visible down a branch of an airway), positions along a curve peak surrounding a local maxima, a value representing the distance (e.g., number of pixels between) separating two local maxima, and/or the size, shape, and orientation of a line or polygon connecting a number of local maxima. A curve peak represents a region in the depth map at which depth values of pixels on one side of the curve peak are increasing while depth values on the other side of the curve peak are decreasing. The curve peak can include a local maximum where the depth associated with a pixel is greater than depths associated with pixels on either side of the pixel. The depth features data repository 405 can store the features and associated locations within the virtual luminal network as a tuple, for example, in the following form—{location$_n$, feature value}—for each identified location. As an example, when the location relates to position within an airway and the feature relates to the distance between two identified local maxima, the tuple can be generated as {locations (airway segment, depth within airway segment), feature value (distance)}. As such, the extracted features in the database can be quickly programmatically evaluated in comparison to features extracted in real-time from images of a navigated anatomical luminal network, and a location corresponding to an identified best or close feature match can be quickly ascertained.

The depth-based position estimator 410 is a module configured to compare the feature(s) extracted in real-time from images of the anatomical luminal network to the pre-computed feature(s) extracted from virtual images. The depth-based position estimator 410 can scan the depth features data repository 405 for a match of a virtual feature to the feature extracted from an actual image, and can use the location corresponding to the match as the position of the instrument (e.g., an endoscope) within the anatomical luminal network. The match can be an exact match, the best match among the available features in the depth features data repository 405, a match within a threshold difference from the extracted feature. The depth-based position estimator 410 can output the position to the state estimator 440, for example, for use as an initial position (a "prior") in a probabilistic evaluation of the position of the instrument, or for use as a prior after occurrence of an adverse event (e.g., coughing) in which the precise location of the instrument becomes unknown. The depth-based position estimator 410 can output the position to the registration calculator 465 for use in generating an initial registration between the model and an EM field disposed around the patient and/or an updated registration.

The endoscope EM sensor data repository 415 is a data storage device that stores data derived from an EM sensor at the distal end of an endoscope. As described above, such a sensor could include EM sensor 125, and EM sensor coils 305 and the resulting data can be used to identify position and orientation of the sensor within the EM field. Similar to the data from EM respiration sensors, data for an endoscope EM sensor can be stored as a tuple in the form of $\{x, y, z, t_n\}$ where x, y, and z represent the coordinates of the sensor in the EM field at time $t_n$. Some embodiments may further include roll, pitch, and yaw of the instrument in the EM sensor tuple. The endoscope EM sensor data repository 415 can store a number of such tuples for each endoscope-based sensor corresponding to a number of different times.

The registration calculator 465 is a module that can identify a registration or mapping between the coordinate frame of the 3D model (e.g., a coordinate frame of the CT scanner used to generate the model) and the coordinate frame of the EM field (e.g., of the EM field generator 120). In order to track a sensor through the patient's anatomy, the navigation fusion system 400 may require a process known as "registration," by which the registration calculator 465 finds the geometric transformation that aligns a single object between different coordinate systems. For instance, a specific anatomical site on a patient may have a representation in the 3D model coordinates and also in the EM sensor coordinates. In order to calculate an initial registration, one implementation of the registration calculator 465 can perform registration as described in U.S. application Ser. No. 15/268,238, filed Sep. 17, 2016, titled "Navigation of Tubular Networks," the disclosure of which is hereby incorporated by reference. As an example of one possible registration technique, the registration calculator 465 can receive data from the endoscope imaging data repository 480 and the EM sensor data repository 415 at a number of different points as the endoscope is inserted into the airways of the patient, for example, as the endoscope reaches various bifurcations. The image data can be used to identify when the distal end of the endoscope has reached a bifurcation, for example, via automated feature analysis. The registration calculator 465 can receive data from the endoscope EM sensor data repository 415 and identify a location of the EM sensor at the distal end of the endoscope as the endoscope is positioned at the bifurcation. Some examples can use not only bifurcations but other points in the patient's airway, and may map such points to corresponding points in a "skeleton" model of the airway. The registration calculator 465 can use data linking at least three of EM positions to points in the model in order to identify the geometric transformation between the EM field and the model. Another embodiment can involve manual registration, for example, by taking at least 3 from a first bifurcation of the patient's airway and from two more bifurcations in the left and right lungs, and can use the corresponding points to calculate the registration. This data to perform the geometric transformation (also referred to as registration data) can be stored in the registration data repository 475 as registration data.

After the initial registration is determined, the registration calculator 465 may update its estimate of the registration transform based on received data so as to increase transform accuracy as well as to compensate for changes to the navigation system, e.g., changes due to movement of the patient. In some aspects, the registration calculator 465 may update the estimate of the registration transform continually, at defined intervals, and/or based on the position of the endoscope (or component(s) thereof) in the luminal network.

Registration data repository 475 is a data storage device that stores the registration data that, as just discussed, is usable to perform a geometric transformation from the coordinate frame of the EM field to the coordinate frame of the model. Also discussed above, the registration data may be generated by the registration calculator 465 and may be updated continually or periodically in some implementations.

The location calculator 430 is a module that receives data from the model data repository 425, registration data repository 475, and the scope position estimator 420 to translate EM sensor coordinates into 3D model coordinates. The scope position estimator 420 calculates an initial position of the EM sensor relative to the position of the EM field generator, as described above. This position also corresponds to a location within the 3D model. In order to translate the initial position of the EM sensor from the EM coordinate frame into the model coordinate frame, the location calculator 430 can access the mapping between the EM coordinate frame and the model coordinate frame (e.g., registration data) as stored in the registration data repository 475. In order to translate the scope position into the 3D model coordinate frame, the location calculator 430 receives, as input, data representing the topography of the 3D model from the model data repository 425, data representing the registration between the EM field and the coordinate frame of the 3D model from the registration data repository 475, and the position of the scope in the EM field from the scope position estimator 420. Some embodiments can also receive prior estimated state data from the state estimator 440. Based on the received data, the location calculator 430 may perform, e.g., on-the-fly transformation of the EM sensor position data to a position in the 3D model. This can represent a preliminary estimate of the position of the distal end of the scope within the topography of the 3D model and can be provided as one input to the state estimator 440 for generating a final estimate of the scope position, as described in more detail below.

The image analyzer 435 is a module that receives data from the endoscope imaging data repository 480 and model data repository 425 and can compare this data to determine endoscope positioning. For example, the image analyzer 435 can access volume-rendered or surface-rendered endoluminal images of the airway tree from the model scans and can compare the rendered images with the real-time image or video frames from the imaging device 315. For example, the images can be registered (e.g., using Powell's optimization, simplex or gradient methods, gradient descent algorithms with normalized cross correlation or mutual information as costs), and then weighted normalized sum of square difference errors and normalized mutual information can be used for comparing the registered images obtained from the two sources. Similarity between a 2D image from the scan and a 2D image received from the endoscope can indicate that the endoscope is positioned near the location of the image from the scan. Such image-based navigation can perform local registrations at bifurcations of patient airways and so can be less susceptible to noise due to patient breathing motion than EM tracking systems. However, as the image analyzer 435 relies on the endoscope video, the analysis can be affected by artifacts in the images caused by patient coughing or mucous obstruction.

The image analyzer 435 can implement object recognition techniques in some embodiments, by which the image analyzer 435 can detect objects present in the field of view of the image data, such as branch openings, lesions, or particles. Using object recognition, the image analyzer can output object data indicating information about what objects were identified, as well as positions, orientations, and/or sizes of objects represented as probabilities. As one example, object recognition can be used to detect objects that may indicate branch points in a luminal network and then determine their position, size, and/or orientation. In one embodiment, in a given image within a luminal network, each branch will typically appear as a dark, approximately elliptical region, and these regions may be detected automatically by a processor, using region-detection algorithms such as maximally stable extremal regions (MSER) as objects. The image analyzer 435 can use light reflective intensity combined with other techniques to identify airways. Further, image analyzer 435 can further track detected objects across a set of sequential image frames to detect which branch has been entered from among a set of possible branches in the luminal network.

The robotic position data repository 470 is a data storage device that stores robotic position data received from medical robotic system 110, for example, data related to physical movement of the medical instrument or part of the medical instrument (e.g., the instrument tip or distal end) by the medical robotic system 110 within the luminal network. Example robotic position data may include, e.g., command data instructing the instrument tip to reach a specific anatomical site and/or change its orientation (e.g., with a specific pitch, roll, yaw, insertion, and retraction for one or both of a leader and a sheath of an endoscopic instrument) within the luminal network, insertion data representing insertion movement of the part of the medical instrument (e.g., the instrument tip or sheath), instrument driver data, and mechanical data representing mechanical movement of an elongate member of the medical instrument, such as, for example, motion of one or more pull wires, tendons or shafts of the endoscope that drive the actual movement of the endoscope within the luminal network.

The navigation path data repository 445 is a data storage device that stores data representing a pre-planned navigation path through the luminal network to a target tissue site. Navigating to a particular point in a luminal network of a patient's body may require certain steps to be taken pre-operatively in order to generate the information needed to create the 3D model of the tubular network and to determine a navigation path within it. As described above, a 3D model may be generated of the topography and structure of the specific patient's airways. A target can be selected, for example, a lesion to biopsy or a portion of organ tissue to repair surgically. In one embodiment, the user is capable of selecting the location of the target by interfacing with a computer display that can show the 3D model, such as by clicking with a mouse or touching a touchscreen. In some embodiments, the navigation path may be identified programmatically by analysis of the model and an identified lesion site to derive a shortest navigation path to the lesion. In some embodiments the path may be identified by a physician, or an automatically-identified path may be modified by a physician. The navigation path can identify a sequence of branches within the luminal network to travel through so as to reach the identified target.

The state estimator 440 is a module that receives inputs and performs analysis of the inputs to determine a state of the medical instrument. For example, the state estimator 440 can receive, as inputs, data from the depth-based position estimator 410, location calculator 430, image analyzer 435, navigation path data repository 445, and robotic position data repository 470. The state estimator 440 can implement a probabilistic analysis to determine a state and corresponding probability of the medical instrument within the luminal network given the provided inputs. Estimated state can refer to one or more of (1) the x,y,z position of the instrument relative to a coordinate frame of a model of the luminal network, (2) whether the instrument is located in a certain region of the model, for example, a particular airway branch, (3) pitch, roll, yaw, insertion, and/or retraction of the instrument, and (4) distance to target. The state estimator 440 can provide the estimated state of the instrument (or the distal tip of the instrument) as a function of time.

In some embodiments, the state estimator 440 can implement a Bayesian framework to determine the state and corresponding probability. Bayesian statistical analysis starts with a belief, called a prior, and then update that belief with observed data. The prior represents an estimate of what the Bayesian model parameters might be and can be represented as a parameterized distribution. The observed data can be gathered to obtain evidence about actual values of the parameters. The outcome of Bayesian analysis is called a posterior, and represents a probabilistic distribution expressing events in terms of confidence. If further data is obtained the posterior can be treated as the prior and updated with the new data. This process employs the Bayes rule, which indicates a conditional probability, for example, how likely is event A if event B happens.

With respect to the disclosed navigation fusion system 400, the state estimator 440 can use previously estimated state data as the prior and can use the inputs from the respiration frequency and/or phase identifier 410, scope position estimator 420, location calculator 430, image analyzer 435, navigation path data repository 445, and/or robotic position data repository 470 as observed data. At the outset of a procedure, the described vision-based initialization techniques can be used to estimate the initial depth and roll in the trachea, and this estimate output from the depth-based position estimator 410 can be used as the prior. The state estimator 440 can perform Bayesian statistical analysis of the prior and observed data to generate a posterior distribution representing a probability and confidence value of each of a number of possible states.

The "probability" of the "probability distribution", as used herein, refers to a likelihood of an estimation of a possible location and/or orientation of the medical instrument being correct. For example, different probabilities may be calculated by one of the algorithm modules indicating the relative likelihood that the medical instrument is in one of several different possible branches within the luminal network. In one embodiment, the type of probability distribution (e.g., discrete distribution or continuous distribution) is chosen to match features of an estimated state (e.g., type of the estimated state, for example, continuous position information vs. discrete branch choice). As one example, estimated states for identifying which segment the medical instrument is in for a trifurcation may be represented by a discrete probability distribution, and may include three discrete values of 20%, 30% and 50% representing chance as being in the location inside each of the three branches as determined by one of the algorithm modules. As another example, the estimated state may include a roll angle of the medical instrument of 40±5 degrees and a segment depth of the instrument tip within a branch may be is 4±1 mm, each represented by a Gaussian distribution which is a type of continuous probability distribution.

In contrast, the "confidence value," as used herein, reflects a measure of confidence in the estimation of the state provided by one of the modules of FIG. 19 based one or more factors. For the EM-based modules, factors such as distortion to EM Field, inaccuracy in EM registration, shift or movement of the patient, and respiration of the patient may affect the confidence in estimation of the state. Particularly, the confidence value in estimation of the state provided by the EM-based modules may depend on the particular respiration cycle of the patient, movement of the patient or the EM field generators, and the location within the anatomy where the instrument tip locates. For the image analyzer 435, examples factors that may affect the confidence value in estimation of the state include illumination condition for the location within the anatomy where the images are captured, presence of fluid, tissue, or other obstructions against or in front of the optical sensor capturing the images, respiration of the patient, condition of the tubular network of the patient itself (e.g., lung) such as the general fluid inside the tubular network and occlusion of the tubular network, and specific operating techniques used in, e.g., navigating or image capturing.

For example, one factor may be that a particular algorithm has differing levels of accuracy at different depths in a patient's lungs, such that relatively close to the airway opening, a particular algorithm may have a high confidence in its estimations of medical instrument location and orientation, but the further into the bottom of the lung the medical instrument travels that confidence value may drop. Generally, the confidence value is based on one or more systemic factors relating to the process by which a result is determined, whereas probability is a relative measure that arises when trying to determine the correct result from multiple possibilities with a single algorithm based on underlying data.

As one example, a mathematical equation for calculating results of an estimated state represented by a discrete probability distribution (e.g., branch/segment identification for a trifurcation with three values of an estimated state involved) can be as follows:

$$S_1 = C_{EM} * P_{1,EM} + C_{Image} * P_{1,Image} + C_{Robot} * P_{1,Robot};$$

$$S_2 = C_{EM} * P_{2,EM} + C_{Image} * P_{2,Image} + C_{Robot} * P_{2,Robot};$$

$$S_3 = C_{EM} * P_{3,EM} + C_{Image} * P_{3,Image} + C_{Robot} * P_{3,Robot}$$

In the example mathematical equation above, $S_i (i=1, 2, 3)$ represents possible example values of an estimated state in a case where 3 possible segments are identified or present in the 3D model, $C_{EM}$, $C_{Image}$, and $C_{Robot}$ represents confidence value corresponding to EM-based algorithm, image-based algorithm, and robot-based algorithm and $P_{i,EM}$, $P_{i,Image}$, and $P_{i,Robot}$ represent the probabilities for segment i. Because of the probabilistic nature of such a fusion algorithm, respiration can be tracked over time and even predicted to overcome latency and outlier disturbances.

In some embodiments, confidence values for data from the robotic position data 470, location calculator 435, and image analyzer 435 can be adaptively determined based on the respiration phase from the respiration frequency and/or phase identifier 410. For example, robotic position data and image data can be affected differently than EM sensor data by respiration motion. In some embodiments, vision data obtained from the endoscope imaging data repository 430 can be used to detect certain kinds of respiratory motion that are not detectable via sensors external to the luminal network, for example, movement of an airway in a cranial-caudal (backward-forward) motion that can be detected through vision processing.

The navigation controller 460 is a module that receives data from the state estimator 440 and the navigation path data repository 445 and uses this data to guide further operation of the medical robotic system 110. For example, the navigation controller 460 can plot the estimated state along a predetermined navigation path and can determine a next movement (e.g., extension/retraction distance, roll, actuation of pull wires or other actuating mechanisms) for the instrument to advance along the navigation path. The navigation controller 460 can automatically control the instrument according to the determined next movement in some embodiments. In some embodiments the navigation controller 460 can output specific instrument movement instructions and/or instrument driver operation instructions for display to the user, such as by the workstation 200. The navigation controller 460 can cause display of side-by-side views of a slice of the 3D model at the estimated position and of the real-time images received from the scope imaging data repository 480 in some embodiments in order to facilitate user-guided navigation.

4. Overview of Example Navigation Techniques

Figure 20:
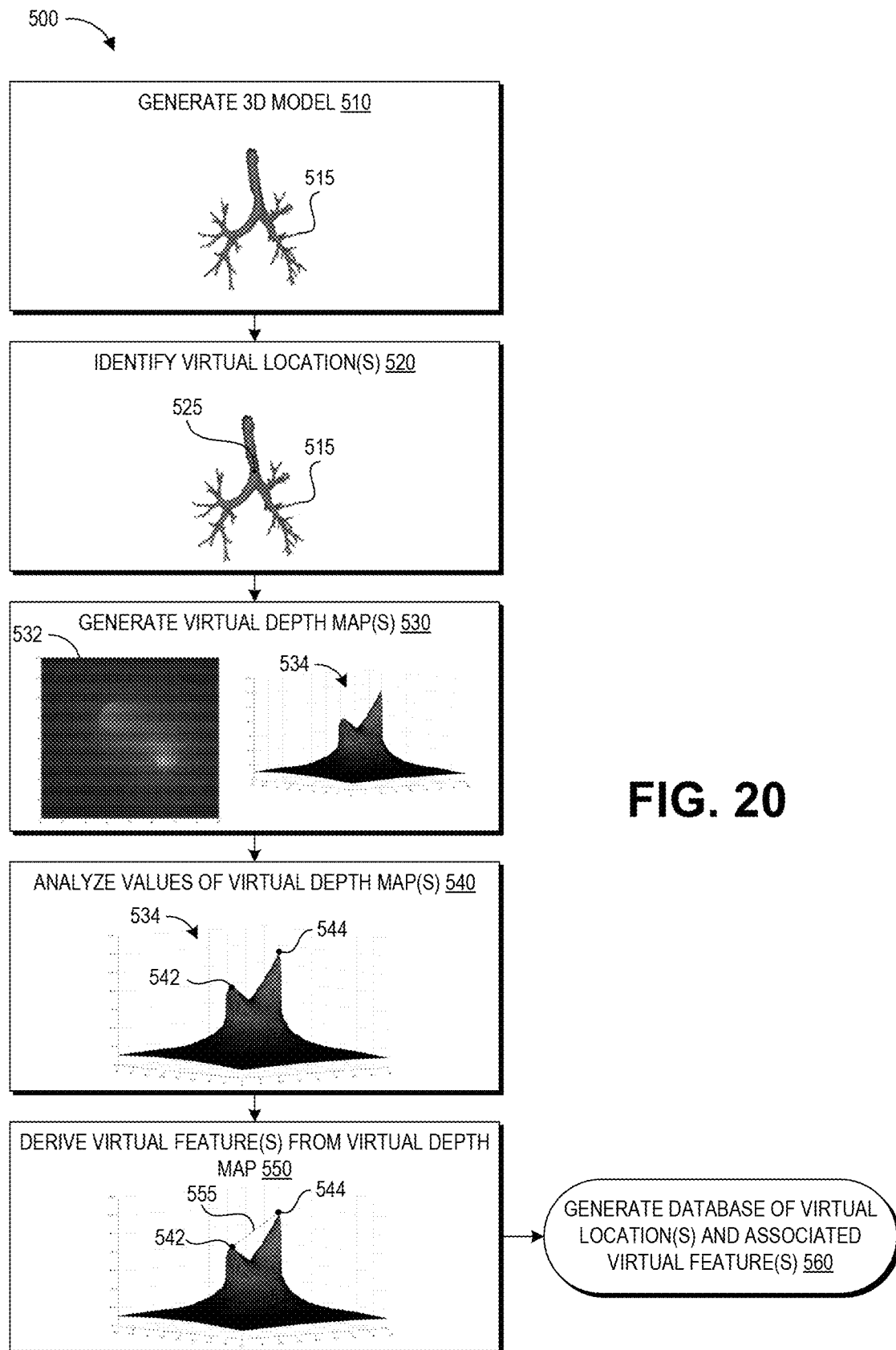
FIG. 20 depicts a flowchart of an example process for generating an extracted virtual feature data set.

In accordance with one or more aspects of the present disclosure, FIG. 20 depicts a flowchart of an example process 500 for generating an extracted virtual feature data set. In some embodiments, the process 500 can be performed pre-operatively, that is, before the start of a medical procedure that uses the models generated by, and features extracted by, the process 500. The process 500 can be implemented in the modeling system 420 FIG. 19, the control and sensor electronics 184 of FIG. 16C, and/or the console base 201 of FIG. 17, or component(s) thereof. The graphical depictions within the flowchart of FIG. 20 are provided to illustrate and not limit the described blocks, and it will be appreciated that the visual representations of the depicted model 515, depth maps 532, 534, and associated features may or may not be generated and displayed during the course of the process 500.

At block 510, model generator 440 can access image data representative of a patient's anatomical luminal network and generate a three-dimensional model 515. For example, CT scans or MRI scans can generate a number of images depicting two-dimensional cross-sections of the anatomical luminal network. The model generator 440 can segment these two-dimensional images to isolate or segment the tissue of the anatomical luminal network, and can then build a three-dimensional point cloud of data based on the isolated tissue positions in the various images and based on the spatial relationship of the cross-sections depicted in the images. The model generator 440 can generate the model based on this three-dimensional point cloud. The three-dimensional model can model the interior surfaces of the anatomical luminal network as a virtual luminal network. For example, the model 515 can be a segmented map of a patient's airways generated from CT scans in some implementations. The model can be any two or three dimensional representation of the actual luminal network (or a portion of the luminal network) of the patient.

At block 520, the feature extractor 450 can identify a number of virtual locations 525 within the model 515. As one example, the feature extractor 450 can identify a number of locations within a trachea segment of a model representing patient airways, for example, a hundred and twenty locations, or greater or fewer locations depending on the parameters of the navigation system 400. In other examples the feature extractor 450 can identify locations within other segments of an airway model, for instance locations along a planned navigation path through the airway model, along the planned navigation path and branches within a predetermined proximity to the planned navigation path, or throughout some or all of the airway segments.

At block 530, the feature extractor 450 can generate a number of virtual depth maps 532, 534 corresponding to the identified locations. For example, the feature extractor 450 can use the identified locations to set locations of a virtual imaging device within the virtual anatomical luminal network, and can generate a virtual depth map 532, 534 for each identified location. The depicted example virtual depth map 532 and virtual depth map 534 depict different representations of the same depth information relating to a virtual representation of a main carina 156 in an airway. Each virtual pixel in the two-dimensional representation of virtual depth map 532 is depicted with a color corresponding to its depth value, while the three-dimensional representation of virtual depth map 534 depicts a dual-peak shape where each virtual pixel is shown at a height along a z-axis corresponding to its depth value. The depicted virtual depth maps are provided to illustrated the concepts of block 530, however in some implementations of the process 500 no such visual representations may be generated, as the process 500 may only require the data representing such depth maps in order to derive features as described below.

In some implementations, at block 530 the feature extractor 450 can access parameters of an imaging device identified for use during a medical procedure during which the luminal network will be navigated, for example, imaging device 315 at the distal end of an endoscope. The feature extractor 450 can set virtual parameters of the virtual imaging device to match the parameters of the imaging device. Such parameters can include field of view, lens distortion, focal length, and brightness shading, and can be based on calibration data or data obtained by testing the imaging device. Brightness shading, also known as vignetting, is a position dependent variation in the amount of light transmitted by an optical system causing darkening of an image near the edges. Vignetting results in a decrease in the amount of light transmitted by an optical system near the periphery of the lens field-of-view (FOV), causing gradual darkening of an image at the edges. Vignetting can be corrected after image capture by calibrating a lens roll off distortion function of the camera. By matching the virtual parameters to the actual parameters, the resulting virtual depth maps 532, 534 may more closely correspond to actual depth maps generated based on images captured by the imaging device.

At block 540, the feature extractor 450 analyzes the values of the virtual depth maps in order to identify one or more depth criteria. A depth criterion can be, for example, the position of a local maxima within the depth map (e.g., a pixel representing the farthest virtual tissue visible down a branch of an virtual airway model) or any position within a threshold distance from the local maxima along a curve peak surrounding the local maxima. The described depth criterion positions can be virtual pixel locations within the virtual depth map.

Block 540 provides a visual illustration of example depth criterion 522 and 544 as local maxima, corresponding to the most distant virtual tissue visible by the virtual camera within the virtual left bronchus and virtual right bronchus. As a general rule, due to the typical shape of the human lungs, a camera or virtual camera positioned near the main carina will be able to see farther into the right bronchus than the left bronchus. Accordingly, the depth criterion 544 corresponds to the most distant depicted virtual tissue within the right bronchus as it has a greater value than depth criterion 542, and the depth criterion 542 corresponds to the most distant depicted virtual tissue within the left bronchus. Such information can assist in identifying roll as described herein.

At block 550, the feature extractor 450 derives a pre-identified virtual feature from the identified depth criteria. For example, as shown the feature extractor 450 can identify the value of the distance 555 separating the depth criteria 542, 544. The distance value can be represented as a number of pixels in an (x,y) space corresponding to a two-dimensional depth map 532 or an (x,y,z) vector corresponding to the three-dimensional depth map 544. The feature extractor 450 can additionally or alternatively derive the identification and positioning of the right and left bronchus as the feature(s). In other implementations, for example, involving depth maps at locations that view branchings of three or more airways, the feature can include the size, shape, and orientation of a polygon connecting three or more local maxima.

At block 560, the feature extractor 450 can generate a database of the virtual location(s) and associated extracted virtual feature(s). This database can be provided to navigation system 400 for use in calculating real-time instrument position determinations, for example, to automatically initialize a probabilistic state estimation, calculate registrations, and perform other navigation-related calculations.

Figure 21:
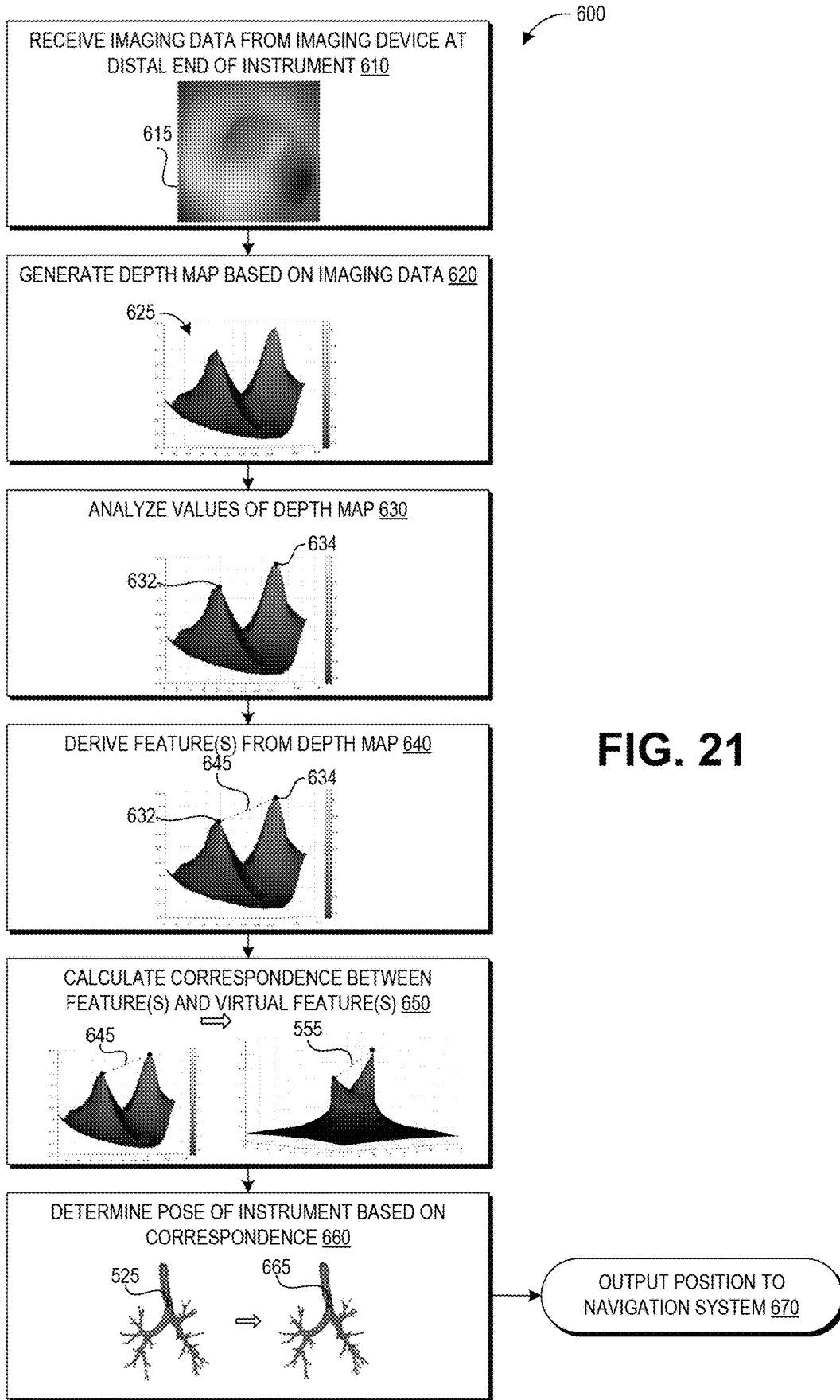
FIG. 21 depicts a flowchart of an example intra-operative process for generating depth information based on captured endoscopic images and calculated correspondence between features of the depth information with the extracted virtual feature data set of FIG. 20.

FIG. 21 depicts a flowchart of an example intra-operative process 600 for generating depth information based on captured endoscopic images and calculated correspondence between features of the depth information with the extracted virtual feature data set of FIG. 20. The process 600 can be implemented by the modeling system 420 and/or navigation fusion system 400 FIG. 19, the control and sensor electronics 184 of FIG. 16C, and/or the console base 201 of FIG. 17, or component(s) thereof.

At block 610, the feature extractor 450 receives imaging data captured by an imaging device at the distal end of an instrument positioned within a patient's anatomical luminal network. For example, the imaging device can be imaging device 315 described above. An example visual representation of the imaging data is shown by image 615 depicting the main carina of patient airways. The image 615 depicts the anatomical main carina corresponding to the virtual main carina represented by the virtual depth map 532 of FIG. 20. Image 615 depicts specific features using a specific visual representation, and image 615 is provided to illustrate and not limit the process 600. Image 615 is representative of endoluminal image data suitable for use in the process 600, and other suitable image data can represent other anatomical structures and/or be depicted as images using different visual representations. Further, some embodiments of the process 600 may operate on imaging data (e.g., values of pixels received from an image sensor of the imaging device) without generating a corresponding visible representation of the image data (e.g., image 615).

At block 620, the feature extractor 450 generates a depth map 620 corresponding to the imaging data represented by image 615. Feature extractor 450 can calculate, for each pixel of the imaging data, a depth value representing an estimated distance between the imaging device and a tissue surface within the anatomical luminal network represented that is corresponding to the pixel. Specifically, the depth value can represent an estimate of the physical distance between an entrance pupil of the imaging device's optical system and the imaged tissue depicted by the pixel. In some embodiments, the feature extractor 450 can use photoclinometry (e.g., shape by shading) processing to generate a depth map based on a single image 615. By using photoclinometry, the feature extractor 450 can be robust to outliers due to reflectance differences between portions of the tissue that may be covered in fluid (e.g. mucous). In some embodiments, the feature extractor 450 can use a stereoscopic image set depicting the imaged region to generate a depth map. For example, a robotically-controlled endoscope can capture a first image at a first location, be robotically retracted, extended, and/or turned a known distance to a second location, and can capture second image at the second location. The feature extractor 450 can use the known translation of the robotically-controlled endoscope and the disparity between the first and second images to generate the depth map.

At block 630, the feature extractor 450 identifies one or more depth criteria in the depth map. As described above with respect to the virtual depth maps, a depth criterion in a depth map generated based on real image data can be, for example, the position of a local maxima within the depth map (e.g., a pixel representing the farthest anatomical tissue visible down a branch of an airway of the patient) or any position within a threshold distance from the local maxima along a curve peak surrounding the local maxima. The described depth criterion positions can be pixel locations within the image 615. The depth criterion selected for identification at block 630 preferably corresponds to the depth criterion identified at block 540.

For example, feature extractor 450 can identify a first pixel of the plurality of pixels corresponding to a first depth criterion in the depth map and a second pixel of the plurality of pixels corresponding to a second depth criterion in the depth map, and in some embodiments each depth criterion can correspond to a local maximum in a region of depth values around the identified pixel. Block 630 provides a visual illustration of example depth criterion 632 and 634 as local maxima, corresponding to the most distant tissue within the left bronchus and right bronchus that is visible by the imaging device 315. Specifically, depth criterion 634 corresponds to a pixel representing the most distant imaged tissue within the right bronchus as it has a greater value than depth criterion 632, and the depth criterion 632 corresponds a pixel representing to the most distant imaged tissue within the left bronchus. Other airway bifurcations can have similar known depth relationships between different branches.

At block 640, the feature extractor 450 derives a pre-identified feature from the identified depth criteria. For example, as shown the feature extractor 450 can calculate the value of the distance 645 (e.g., quantity of separation) between the pixels corresponding to depth criteria 632 and 634. The distance value can be represented as a number of pixels in an (x,y) space corresponding to a two-dimensional depth map or an (x,y,z) vector corresponding to the three-dimensional depth map 625, preferably in the same format as the feature identified at block 550 of process 500. The feature extractor 450 can additionally or alternatively derive the identification and positioning of the right and left bronchus as the feature(s). In other implementations, for example, involving depth maps at locations that view branchings of three or more airways, the feature can include the size, shape, and orientation of a polygon connecting three or more local maxima.

At block 650, the depth-based position estimator 410 calculates a correspondence between the feature(s) derived from the imaging data and a number of features in depth features data repository 405. For example, the feature derived from the imaging data can be the value of distance 645 calculated based on the identified depth criteria of the depth map 625, as described with respect to block 640. The depth-based position estimator 410 can compare the value of distance 645 to distance values associated with a number of locations in the trachea to identify one of the distance values that corresponds to the value of distance 645. These distance values can be pre-computed and stored in data repository 405 as described with respect to FIG. 20 above, or can be computed in real-time as the patient's anatomy is being navigated. Values computed in real time may be stored in a working memory during correspondence calculations, or may be added to the data repository 405 and then later accessed if the location corresponding to the value is involved in additional correspondence calculations.

To determine the correspondence, the depth-based position estimator 410 can identify the value of distance 555 (discussed above with respect to block 550 of process 500) as an exact match to the value of distance 645, as the best match (e.g., closest value) to the value of distance 645 among the options in the depth features data repository 405, or as the first match within a predetermined threshold of the value of distance 645. It will be appreciated that the navigation system 400 can be preconfigured to look for an exact match, best match, or first within-threshold match, or to dynamically look for one of these options based on current navigation conditions, based on a tradeoff between computation speed and accuracy of the position output.

At block 660, the depth-based position estimator 410 determines an estimated pose of the distal end of the instrument within the anatomical luminal network based on the virtual location associated with the virtual feature that was identified in the correspondence calculations of block 650. The pose can include the position of the instrument (e.g., insertion depth within a segment of an airway or other luminal network portion), the roll, pitch, and/or yaw of the instrument, or other degrees of freedom. As described above, the depth features data repository 405 can store a database of tuples or associated values including locations and the feature(s) extracted from virtual images generated at the locations. Accordingly, at block 660 the depth-based position estimator 410 can access the location information stored in association with the feature identified at block 650 and output this location as the position of the instrument. In some embodiments, block 660 can include identifying an angular transformation between the positions of the right and left bronchus in image 615 and the virtual positions of the virtual right and left bronchus in virtual depth map 532. The angular transformation can be used to determine the roll of the instrument within the airway.

At block 670, the depth-based position estimator 410 outputs the identified pose for use in the navigation system 400. As described above, the pose can be output to the state estimator 440 and used as an automatically-determined Bayesian prior during initialization, as opposed to an initialization process that requires the user to reposition the endoscope at a number of specified locations in order to enable the initialization. In some embodiments, the pose can be output to the registration calculator 465 for use in calculating a registration between the model coordinate frame and the EM coordinate frame. Beneficially, the processes 500 and 600 enable such calculations without requiring the physician to deviate from a pre-determined navigation path through the patient's airways to the target tissue site.

5. Alternatives

Several alternatives of the subject matter described herein are provided below.

1. A method of facilitating navigation of an anatomical luminal network of a patient, the method, executed by a set of one or more computing devices, comprising:
   receiving imaging data captured by an imaging device at a distal end of an instrument positioned within the anatomical luminal network;
   accessing a virtual feature derived from a virtual image simulated from a viewpoint of a virtual imaging device positioned at a virtual location within a virtual luminal network representative of the anatomical luminal network;
   calculating a correspondence between a feature derived from the imaging data and the virtual feature derived from the virtual image; and
   determining a pose of the distal end of the instrument within the anatomical luminal network based on the virtual location associated with the virtual feature.

2. The method of alternative 1, further comprising generating a depth map based on the imaging data, wherein the virtual feature is derived from a virtual depth map associated with the virtual image, and wherein calculating the correspondence is based at least partly on correlating one or more features of the depth map and one or more features of the virtual depth map.

3. The method of alternative 2, further comprising:
   generating the depth map by calculating, for each pixel of a plurality of pixels of the imaging data, a depth value representing an estimated distance between the imaging device and a tissue surface within the anatomical luminal network corresponding to the pixel;
   identifying a first pixel of the plurality of pixels corresponding to a first depth criterion in the depth map and a second pixel of the plurality of pixels corresponding to a second depth criterion in the depth map;
   calculating a first value representing a distance between the first and second pixels;
   wherein the virtual depth map comprises, for each virtual pixel of a plurality of virtual pixels, a virtual depth value representing a virtual distance between the virtual imaging device and a portion of the virtual luminal network represented by the virtual pixel, and wherein accessing the virtual feature derived from the virtual image comprises accessing a second value representing a distance between first and second depth criteria in the virtual depth map; and
   calculating the correspondence based on comparing the first value to the second value.

4. The method of alternative 3, further comprising:
   accessing a plurality of values representing distances between first and second depth criteria in a plurality of virtual depth maps each representing a different one of a plurality of virtual locations within the virtual luminal network; and
   calculating the correspondence based on the second value corresponding more closely to the first value than other values of the plurality of values.

5. The method of any one of alternatives 3 or 4, wherein the anatomical luminal network comprises airways and the imaging data depicts a bifurcation of the airways, the method further comprising:
   identifying one of the first and second depth criteria as a right bronchus in each of the depth map and the virtual depth map; and
   determining a roll of the instrument based on an angular distance between a first position of the right bronchus in the depth map and a second position of the right bronchus in the virtual depth map, wherein the pose of the distal end of the instrument within the anatomical luminal network comprises the determined roll.

6. The method of any of alternatives 2-5, further comprising:
   identifying three or more depth criteria in each of the depth map and the virtual depth map;
   determining a shape and location of a polygon connecting the depth criteria in each of the depth map and the virtual depth map; and
   calculating the correspondence based on comparing the shape and location of the polygon of the depth map to the shape and location of the polygon of the virtual depth map.

7. The method of any of alternatives 2-6, wherein generating the depth map is based on photoclinometry.

8. The method of any of alternatives 1-7, further comprising:
   calculating a probabilistic state of the instrument within the anatomical luminal network based on a plurality of inputs comprising the position; and
   guiding navigation of the instrument through the anatomical luminal network based at least partly on the probabilistic state.

9. The method of alternative 8, further comprising initializing a navigation system configured to calculate the probabilistic state and guide the navigation of the anatomical luminal network based on the probabilistic state, wherein the initializing of the navigation system comprises setting a prior of a probability calculator based on the position.

10. The method of alternative 9, further comprising:
    receiving additional data representing an updated pose of the distal end of the instrument;
    setting a likelihood function of the probability calculator based on the additional data; and
    determining the probabilistic state using the probability calculator based on the prior and the likelihood function.

11. The method of any one of alternatives 8-10, further comprising:
    providing the plurality of inputs to a navigation system configured to calculate the probabilistic state, a first input comprising the pose of the distal end of the instrument and at least one additional input comprising one or both of robotic position data from a robotic system actuating movement of the instrument and data received from a position sensor at the distal end of the instrument; and calculating the probabilistic state of the instrument based on the first input and the at least one additional input.

12. The method of any one of alternatives 1-11, further comprising determining a registration between a coordinate frame of the virtual luminal network and a coordinate frame of an electromagnetic field generated around the anatomical luminal network based at least partly on the pose of the distal end of the instrument within the anatomical luminal network determined based on the calculated correspondence.

13. The method of any one of alternatives 1-12, wherein determining the position comprises determining a distance that the distal end of the instrument is advanced within a segment of the anatomical luminal network.

14. A system configured to facilitate navigation of an anatomical luminal network of a patient, the system comprising:
an imaging device at a distal end of an instrument;
at least one computer-readable memory having stored thereon executable instructions; and
one or more processors in communication with the at least one computer-readable memory and configured to execute the instructions to cause the system to at least:
receive imaging data captured by the imaging device with the distal end of the instrument positioned within the anatomical luminal network;
access a virtual feature derived from a virtual image simulated from a viewpoint of a virtual imaging device positioned at a virtual location within a virtual luminal network representative of the anatomical luminal network;
calculate a correspondence between a feature derived from the imaging data and the virtual feature derived from the virtual image; and
determine a pose of the distal end of the instrument relative within the anatomical luminal network based on the virtual location associated with the virtual feature.

15. The system of alternative 14, wherein the one or more processors are configured to execute the instructions to cause the system to at least:
generate a depth map based on the imaging data, wherein the virtual image represents a virtual depth map; and
determine the correspondence based at least partly on correlating one or more features of the depth map and one or more features of the virtual depth map.

16. The system of alternative 15, wherein the one or more processors are configured to execute the instructions to cause the system to at least:
generate the depth map by calculating, for each pixel of a plurality of pixels of the imaging data, a depth value representing an estimated distance between the imaging device and a tissue surface within the anatomical luminal network corresponding to the pixel;
identify a first pixel of the plurality of pixels corresponding to a first depth criterion in the depth map and a second pixel of the plurality of pixels corresponding to a second depth criterion in the depth map;
calculate a first value representing a distance between the first and second pixels;
wherein the virtual depth map comprises, for each virtual pixel of a plurality of virtual pixels, a virtual depth value representing a virtual distance between the virtual imaging device and a portion of the virtual luminal network represented by the virtual pixel, and wherein the feature derived from the virtual image comprises a second value representing a distance between first and second depth criteria in the virtual depth map; and
determine the correspondence based on comparing the first value to the second value.

17. The system of alternative 16, wherein the one or more processors are configured to execute the instructions to cause the system to at least:
access a plurality of values representing distances between first and second depth criteria in a plurality of virtual depth maps each representing a different one of a plurality of virtual locations within the virtual luminal network; and
calculate the correspondence based on the second value corresponding more closely to the first value than other values of the plurality of values identify the second value as a closest match to the first value among the plurality of values.

18. The system of any one of alternatives 16-17, wherein the anatomical luminal network comprises airways and the imaging data depicts a bifurcation of the airways, wherein the one or more processors are configured to execute the instructions to cause the system to at least:
identify one of the first and second depth criteria as a right bronchus in each of the depth map and the virtual depth map; and
determine a roll of the instrument based on an angular distance between a first position of the right bronchus in the depth map and a second position of the right bronchus in the virtual depth map, wherein the pose of the distal end of the instrument within the anatomical luminal network comprises the determined roll.

19. The system of any one of alternatives 15-18, wherein the one or more processors are configured to execute the instructions to cause the system to at least:
identify three or more depth criteria in each of the depth map and the virtual depth map;
determine a shape and location of a polygon connecting the three or more depth criteria in each of the depth map and the virtual depth map; and
calculate the correspondence based on comparing the shape and location of the polygon of the depth map to the shape and location of the polygon of the virtual depth map.

20. The system of any one of alternatives 15-19, wherein the one or more processors are configured to execute the instructions to cause the system to at least generate the depth map based on photoclinometry.

21. The system of any one of alternatives 14-20, wherein the one or more processors are configured to communicate with a navigation system, and wherein the one or more processors are configured to execute the instructions to cause the system to at least:
calculate a probabilistic state of the instrument within the anatomical luminal network using the navigation system based at least partly on a plurality of inputs comprising the position; and
guide navigation of the instrument through the anatomical luminal network based at least partly on the probabilistic state calculated by the navigation system.

22. The system of alternative 21, further comprising a robotic system configured to guide movements of the instrument during the navigation.

23. The system of alternative 22, wherein the plurality of inputs comprise robotic position data received from the robotic system, and wherein the one or more processors are configured to execute the instructions to cause the system to at least calculate the probabilistic state of the instrument using the navigation system based at least partly on the position and on the robotic position data.

24. The system of any one of alternatives 21-23, further comprising a position sensor at the distal end of an instrument, the plurality of inputs comprise data received from the position sensor, and wherein the one or more processors are configured to execute the instructions to cause the system to at least calculate the probabilistic state of the instrument using the navigation system based at least partly on the position and on the data received from the position sensor.

25. The system of any one of alternatives 14-24, wherein the one or more processors are configured to execute the instructions to cause the system to at least determine a registration between a coordinate frame of the virtual luminal network and a coordinate frame of an electromagnetic field generated around the anatomical luminal network based at least partly on the position.

26. A non-transitory computer readable storage medium having stored thereon instructions that, when executed, cause at least one computing device to at least:
   access a virtual three-dimensional model of internal surfaces of an anatomical luminal network of a patient;
   identify a plurality of virtual locations within the virtual three-dimensional model;
   for each virtual location of the plurality of virtual locations within the virtual three-dimensional model:
      generate a virtual depth map representing virtual distances between a virtual imaging device positioned at the virtual location and a portion of the internal surfaces within a field of view of the virtual imaging device when positioned at the virtual location, and
      derive at least one virtual feature from the virtual depth map; and
   generate a database associating the plurality of virtual locations with the at least one virtual feature derived from the corresponding virtual depth map.

27. The non-transitory computer readable storage medium of alternative 26, wherein the instructions, when executed, cause the at least one computing device to at least provide the database to a navigation system configured to guide navigation of an instrument through the anatomical luminal network during a medical procedure.

28. The non-transitory computer readable storage medium of alternative 27, wherein the instructions, when executed, cause the at least one computing device to at least:
   access data representing an imaging device positioned at a distal end of the instrument;
   identify image capture parameters of the imaging device; and
   set virtual image capture parameters of the virtual imaging device to correspond to the image capture parameters of the imaging device.

29. The non-transitory computer readable storage medium of alternative 28, wherein the instructions, when executed, cause the at least one computing device to at least generate the virtual depth maps based on the virtual image capture parameters.

30. The non-transitory computer readable storage medium of any one of alternatives 28-29, wherein the image capture parameters comprise one or more of field of view, lens distortion, focal length, and brightness shading.

31. The non-transitory computer readable storage medium of any one of alternatives 26-30, wherein the instructions, when executed, cause the at least one computing device to at least:
   for each virtual location of the plurality of virtual locations:
      identify first and second depth criteria in the virtual depth map, and
      calculate a value representing a distance between the first and second depth criteria; and
   create the database by associating the plurality of virtual locations with the corresponding value.

32. The non-transitory computer readable storage medium of any one of alternatives 26-31, wherein the instructions, when executed, cause the at least one computing device to at least:
   for each virtual location of the plurality of virtual locations:
      identify three or more depth criteria in the virtual depth map, and
      determine a shape and location of a polygon connecting the three or more depth criteria; and
      create the database by associating the plurality of virtual locations with the shape and location of the corresponding polygon.

33. The non-transitory computer readable storage medium of any one of alternatives 26-32, wherein the instructions, when executed, cause the at least one computing device to at least:
   generate a three-dimensional volume of data from a series of two-dimensional images representing the anatomical luminal network of the patient; and
   form the virtual three-dimensional model of the internal surfaces of the anatomical luminal network from the three-dimensional volume of data.

34. The non-transitory computer readable storage medium of alternative 33, wherein the instructions, when executed, cause the at least one computing device to at least control a computed tomography imaging system to capture the series of two-dimensional images.

35. The non-transitory computer readable storage medium of any one of alternatives 33-34, wherein the instructions, when executed, cause the at least one computing device to at least form the virtual three-dimensional model by applying volume segmentation to the three-dimensional volume of data.

36. A method of facilitating navigation of an anatomical luminal network of a patient, the method, executed by a set of one or more computing devices, comprising:
   receiving a stereoscopic image set representing an interior of the anatomical luminal network;
   generating a depth map based on the stereoscopic image set;
   accessing a virtual feature derived from a virtual image simulated from a viewpoint of a virtual imaging device positioned at a location within a virtual luminal network;
   calculating a correspondence between a feature derived from the depth map and the virtual feature derived from the virtual image; and
   determining a pose of the distal end of the instrument within the anatomical luminal network based on the virtual location of associated with the virtual feature.

37. The method of alternative 36, wherein generating the stereoscopic image set comprises:
   positioning an imaging device at a distal end of an instrument at a first location within the anatomical luminal network;
   capturing a first image of an interior of the anatomical luminal network with the imaging device positioned at the first location;

robotically controlling the imaging device to move a known distance to a second location within the anatomical luminal network; and capturing a second image of the interior of the anatomical luminal network with the imaging device positioned at the second location.

38. The method of alternative 37, wherein robotically controlling the imaging device to move the known distance comprises one or both of retracting the imaging device and angularly rolling the imaging device.

6. Implementing Systems and Terminology

Implementations disclosed herein provide systems, methods and apparatus for improved navigation of luminal networks.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The feature correspondence calculations, position estimation, and robotic motion actuation functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A method of facilitating navigation of an anatomical luminal network of a patient, the method, executed by a set of one or more computing devices, comprising:
   receiving imaging data captured by an imaging device at a distal end of an instrument positioned within the anatomical luminal network, the anatomical luminal network including a first branch and a second branch;
   generating a depth map based at least in part on the imaging data;
   identifying:
      a first depth criterion associated with the depth map and representing a position of the first branch; and
      a second depth criterion associated with the depth map and representing a position of the second branch;
   determining a separation distance between the first depth criterion and the second depth criterion;
   accessing one or more features associated with a virtual image, the virtual image simulated from a viewpoint of a virtual imaging device positioned at a virtual location within a virtual luminal network representative of the anatomical luminal network, the virtual luminal network including a virtual first branch corresponding to the first branch and a virtual second branch corresponding to the second branch; and
   determining a value representing at least one angular degree of freedom of the distal end of the instrument within the anatomical luminal network based at least in part on the separation distance and the one or more features associated with the virtual image.

2. The method of claim 1, wherein the anatomical luminal network includes a third branch bifurcating into the first branch and the second branch, the method further comprising determining an insertion depth of the distal end of the instrument within the third branch based on the virtual location of the virtual image.

3. The method of claim 2, wherein the value representing the at least one angular degree of freedom of the distal end of the instrument represents a roll of the distal end of the instrument.

4. The method of claim 3, further comprising:
   generating an electromagnetic field around the anatomical luminal network; and
   determining a registration between a coordinate frame of the virtual luminal network and a coordinate frame of the electromagnetic field based on the insertion depth and the roll of the distal end of the instrument.

5. The method of claim 1, wherein said generating the depth map based at least in part on the imaging data involves calculating, for each pixel of a plurality of pixels of the imaging data, a depth value representing an estimated distance between the imaging device and a tissue surface within the anatomical luminal network corresponding to the pixel.

6. The method of claim 5, further comprising:
identifying a first pixel of the plurality of pixels corresponding to the first depth criterion in the depth map;
determining a first location of the first branch in the imaging data based on a position of the first pixel;
identifying a second pixel of the plurality of pixels corresponding to the second depth criterion in the depth map; and
determining a second location of the second branch in the imaging data based on a position of the second pixel.

7. The method of claim 6, further comprising:
determining that the first pixel has a greater depth value than the second pixel; and
identifying that the first location corresponds to the first branch based on said determining that the first pixel has the greater depth value.

8. The method of claim 1, wherein:
the first depth criterion represents a most distant imaged tissue within the first branch; and
the second depth criterion represents a most distant imaged tissue within the second branch.

9. The method of claim 6, wherein:
the first depth criterion corresponds to a first local maximum in a first region of depth values around the first pixel; and
the second depth criterion corresponds to a second local maximum in a second region of depth values around the second pixel.

10. The method of claim 1, further comprising determining the value representing the at least one angular degree of freedom of the distal end of the instrument based on an angular distance between a first position of the first branch in the imaging data and a second position of the virtual first branch in the virtual image.

11. A system configured to facilitate navigation of an anatomical luminal network of a patient, the system comprising:
an imaging device at a distal end of an instrument;
at least one computer-readable memory having stored thereon executable instructions; and
one or more processors in communication with the at least one computer-readable memory and configured to execute the executable instructions to cause the system to:
receive imaging data captured by the imaging device with the distal end of the instrument positioned within the anatomical luminal network, the anatomical luminal network including a first branch and a second branch;
generate a depth map representing the image data;
identify first and second pixels of the depth map representing a first positioning of the first branch and the second branch in the imaging data;
determine a quantity of separation between the first and second pixels of the depth map;
access one or more features associated with a virtual image, the virtual image simulated from a viewpoint of a virtual imaging device positioned at a virtual location within a virtual luminal network representative of the anatomical luminal network, the virtual luminal network including a virtual first branch corresponding to the first branch and a virtual second branch corresponding to the second branch, the one or more features associated with the virtual image representing a second positioning of the virtual first branch and the virtual second branch in the virtual image; and
determine a value representing at least one angular degree of freedom of the distal end of the distal end of the instrument within the anatomical luminal network based at least in part on the quantity of separation and the one or more features associated with the virtual image.

12. The system of claim 11, wherein the anatomical luminal network includes a third branch bifurcating into the first branch and the second branch, and wherein the one or more processors are configured to execute the executable instructions to cause the system to determine an insertion depth of the distal end of the instrument within the third branch based on the virtual location of the virtual image.

13. The system of claim 12, wherein the value representing the at least one angular degree of freedom of the distal end of the instrument indicates a roll of the distal end of the instrument.

14. The system of claim 13, wherein the one or more processors are further configured to execute the executable instructions to cause the system to:
generate an electromagnetic field around the anatomical luminal network; and
determine a registration between a coordinate frame of the virtual luminal network and a coordinate frame of the electromagnetic field based on the insertion depth and the roll of the distal end of the instrument.

15. The system of claim 11, wherein the one or more processors are configured to execute the executable instructions to cause the system to:
generate the depth map at least in part by calculating, for each pixel of a plurality of pixels of the imaging data, a depth value representing an estimated distance between the imaging device and a tissue surface within the anatomical luminal network corresponding to the pixel;
identify the first pixel as corresponding to a first depth criterion in the depth map;
determine a first location of the first branch in the imaging data based on a position of the first pixel;
identify the second pixel as corresponding to a second depth criterion in the depth map; and
determine a second location of the second branch in the imaging data based on a position of the second pixel.

16. The system of claim 15, wherein the one or more processors are further configured to execute the executable instructions to cause the system to:
determine that the first pixel has a greater depth value than the second pixel; and
identify that the first location corresponds to the first branch based on said determination that the first pixel has the greater depth value.

17. The system of claim 15, wherein:
the first depth criterion represents a most distant imaged tissue within the first branch; and
the second depth criterion represents a most distant imaged tissue within the second branch.

18. The system of claim 15, wherein:
the first depth criterion corresponds to a first local maximum in a first region of depth values around the first pixel; and
the second depth criterion corresponds to a second local maximum in a second region of depth values around the second pixel.

19. The system of claim 11, wherein the one or more processors are further configured to execute the executable instructions to cause the system to determine the value representing the at least one angular degree of freedom of the distal end of the instrument based on an angular distance between a first position of the first branch in the imaging data and a second position of the virtual first branch in the virtual image.

20. A non-transitory computer readable storage medium having stored thereon instructions that, when executed, cause at least one computing device to:
   receive imaging data captured by an imaging device at a distal end of an instrument positioned within an anatomical luminal network, wherein the anatomical luminal network includes a first branch and a second branch;
   generate depth map data based at least in part on the imaging data;
   identify first and second depth map features in the depth map data representing a first positioning of the first branch and the second branch in the imaging data;
   determining a first distance between the first and second depth map features;
   access a virtual image including a virtual first branch corresponding to the first branch and a virtual second branch corresponding to the second branch, the virtual first branch and the virtual second branch being separated by a second distance in the virtual image; and
   determine a value representing at least one angular degree of freedom of the distal end of the instrument within the anatomical luminal network based at least in part on the first distance and the second distance.

21. The non-transitory computer readable storage medium of claim 20, wherein:
   the anatomical luminal network includes a third branch bifurcating into the first branch and the second branch; and
   the instructions, when executed, further cause the at least one computing device to determine an insertion depth of the distal end of the instrument within the third branch based on a virtual location of the virtual image.

22. The non-transitory computer readable storage medium of claim 21, wherein the value representing the at least one angular degree of freedom of the distal end of the instrument comprises a roll of the distal end of the instrument.

23. The non-transitory computer readable storage medium of claim 22, wherein the instructions, when executed, further cause the at least one computing device to:
   generate an electromagnetic field around the anatomical luminal network; and
   determine a registration between a coordinate frame of a virtual luminal network associated with the virtual image and a coordinate frame of the electromagnetic field based on the insertion depth and the roll of the distal end of the instrument.

24. The non-transitory computer readable storage medium of claim 20, wherein the instructions, when executed, cause the at least one computing device to:
   generate the depth map data by calculating, for each pixel of a plurality of pixels of the imaging data, a depth value representing an estimated distance between the imaging device and a tissue surface within the anatomical luminal network corresponding to the pixel;
   identify a first pixel of the plurality of pixels corresponding to a first depth criterion in the depth map;
   determine a first location of the first branch in the imaging data based on a position of the first pixel;
   identify a second pixel of the plurality of pixels corresponding to a second depth criterion in the depth map; and
   determine a second location of the second branch in the imaging data based on a position of the second pixel.

25. The non-transitory computer readable storage medium of claim 24, wherein the instructions, when executed, further cause the at least one computing device to:
   determine that the first pixel has a greater depth value than the second pixel; and
   determine that the first location corresponds to the first branch based on the determination that the first pixel has the greater depth value.

26. The non-transitory computer readable storage medium of claim 24, wherein the first depth criterion represents a most distant imaged tissue within the first branch, and wherein the second depth criterion represents a most distant imaged tissue within the second branch.

27. The non-transitory computer readable storage medium of claim 24, wherein the first depth criterion corresponds to a first local maximum in a first region of depth values around the first pixel, and wherein the second depth criterion corresponds to a second local maximum in a second region of depth values around the second pixel.

28. The non-transitory computer readable storage medium of claim 20, wherein the instructions, when executed, further cause the at least one computing device to determine the value representing the at least one angular degree of freedom of the distal end of the instrument based on an angular distance between a first position of the first branch in the imaging data and a second position of the virtual first branch in the virtual image.

* * * * *